United States Patent

Abreu

[11] Patent Number: 6,120,460
[45] Date of Patent: Sep. 19, 2000

[54] METHOD AND APPARATUS FOR SIGNAL ACQUISITION, PROCESSING AND TRANSMISSION FOR EVALUATION OF BODILY FUNCTIONS

[76] Inventor: Marcio Marc Abreu, 5709 Elmer St., No. 102, Pittsburgh, Pa. 15232

[21] Appl. No.: 09/184,127
[22] Filed: Nov. 2, 1998

Related U.S. Application Data

[63] Continuation of application No. 08/707,508, Sep. 4, 1996, Pat. No. 5,830,139.

[51] Int. Cl.[7] .................................................. A61B 5/00
[52] U.S. Cl. .......................................... 600/558; 600/405
[58] Field of Search .................................. 600/558, 584, 600/405; 604/17

[56] References Cited

U.S. PATENT DOCUMENTS

| | | | |
|---|---|---|---|
| 3,545,260 | 12/1970 | Lichtenstein et al. | 73/80 |
| 3,585,849 | 6/1971 | Grolman | 73/80 |
| 3,724,263 | 4/1973 | Rose et al. | 73/80 |
| 4,305,399 | 12/1981 | Beale | 128/645 |
| 4,386,831 | 6/1983 | Grounauer | 600/558 |
| 4,485,820 | 12/1984 | Flour | 600/558 |
| 4,628,938 | 12/1986 | Lee | 128/652 |
| 4,629,424 | 12/1986 | Lauks et al. | 600/590 |
| 4,771,792 | 9/1988 | Seale | 128/774 |
| 4,860,755 | 8/1989 | Erath | 128/645 |
| 4,922,913 | 5/1990 | Wates et al. | |

(List continued on next page.)

OTHER PUBLICATIONS

RCA Technical Notes, *Contact Lens Tonometer* by Robert E. Morey, RCA TN No.: 602, dated Dec. 1964, 2 pages.

Ophthal. Physiol. Opt., 1989, vol. 9, Apr., 1989 Research Note, *Multiple Applications of the NCT: An Assessment of the Instrument's Effect on IOP* by G. E. Russell and J. P. G. Bergmanson, pp. 212–214.

Arch Ophthalmol—vol. 97, Mar. 1979, *The Pneumatonograph*—A Laboratory Study, by Robert A. Moses, M.D. and Walter J. Grodzki, Jr., D.D.S., pp. 547–552.

(List continued on next page.)

*Primary Examiner*—Max Hindenburg
*Attorney, Agent, or Firm*—Jacobson, Price, Holman & Stern, PLLC

[57] ABSTRACT

Utilization of a contact device placed on the front part of the eye in order to detect physical and chemical parameters of the body as well as the non-invasive delivery of compounds according to these physical and chemical parameters, with signals preferably being transmitted continuously as electromagnetic waves, radio waves, infrared and the like. One of the parameters to be detected includes non-invasive blood analysis utilizing chemical changes and chemical products that are found in the front part of the eye and in the tear film. A transensor mounted in the contact device laying on the cornea or the surface of the eye is capable of evaluating and measuring physical and chemical parameters in the eye including non-invasive blood analysis. The system preferably utilizes eye lid motion and/or closure of the eye lid to activate a microminiature radio frequency sensitive transensor mounted in the contact device. The signal can be communicated by cable, but is preferably actively or passively radio telemetered to an externally placed receiver. The signal can then be processed, analyzed and stored. Several parameters can be detected including a complete non-invasive analysis of blood components, measurement of systemic and ocular blood flow, measurement of heart rate and respiratory rate, tracking operations, detection of ovulation, detection of radiation and drug effects, diagnosis of ocular and systemic disorders and the like. Other advantages are somnolence awareness, activation of devices by disabled individuals, a new drug delivery system and new therapy for ocular and neurologic disorders, and treatment of cancer in the eye or other parts of the body, and an evaluation system for the overall health status of an individual. The device quantifies non-invasively the amount of the different chemical components in the blood using a contact device with suitable electrodes and membranes laying on the surface of the eye and in direct contact with the tear film or surface of the eye, with the data being preferably transmitted utilizing radio waves, but alternatively sound waves, light waves, wire, or telephone lines can be used for transmission.

22 Claims, 35 Drawing Sheets

U.S. PATENT DOCUMENTS

| | | | |
|---|---|---|---|
| 4,944,303 | 7/1990 | Katsuragi | 128/648 |
| 4,947,849 | 8/1990 | Takahashi et al. | 128/648 |
| 4,951,671 | 8/1990 | Coan | 128/652 |
| 5,005,577 | 4/1991 | Frenkel | 128/645 |
| 5,076,274 | 12/1991 | Matsumoto | 128/645 |
| 5,109,852 | 5/1992 | Kaye et al. | 128/645 |
| 5,148,807 | 9/1992 | Hsu | 128/645 |
| 5,165,409 | 11/1992 | Coan | 128/652 |
| 5,179,953 | 1/1993 | Kursar | 128/645 |
| 5,183,044 | 2/1993 | Nishio et al. | 128/648 |
| 5,217,015 | 6/1993 | Kaye et al. | 128/645 |
| 5,251,627 | 10/1993 | Morris | 128/645 |
| 5,295,495 | 3/1994 | Maddess | 128/898 |
| 5,375,595 | 12/1994 | Sinha et al. | 128/645 |
| 5,636,635 | 6/1997 | Massie et al. | 128/652 |

OTHER PUBLICATIONS

IEEE Transactions on Bio–Medical Engineering, vol. BME–14, No. 2, Apr., 1967, *Miniature Passive Pressure Transensor for Implanting in the Eye*, by C. C. Collins, pp. 74–83.

Trans. Amer. Acad. of O. & O., Jan.–Feb. 1957, *Tonometer Calibration, An Attempt to Remove Discrepancies Found in the 1954 Calibration Scale for Schiotz Tonometers* by Jonas S. Friedenwald, M. D., pp. 108–123.

Investigative Ophthalmology, Feb. 1962, *The Relationship Between Pressure and Volume Changes in Living and Dead Rabbit Eyes*, by John E. Eisenlohr and Maurice E. Langham, pp. 63–77.

InvestigativeOphthalmology, Sep. 1971, vol. 10, No. 9, *Theory and Calibration of the Schiotz Tononmeter VII. Experimental Results of Tonometric Measurements: Scale Reading Versus Indentation Volume*, by Robert A. Moses and Walter J. Grodzki, pp. 716–723.

The British Journal of Ophthalmology, Jun. 1920, Communications, *Tonometry*, by H.J. Schiotz, pp. 249–261.

Ophthalmologica vol. 150, No. 5, (1965), *Rheology of the Human Sclera, Unifying Formulation of Ocular Rigidity*, by W. K. McEwen and Roger St. Helen, pp. 322–346.

A.M.A. Archives of Ophthalmology, vol. 57, Apr. 1957, *Tonometer Calibration*, by Earle H. McBain, M.D., pp. 250–531.

American Journal of Ophthalmology, vol. 20, No. 10, Oct. 1937, *Contribution to the Theory and Practice of Tonometry* by Jonas S. Friedenwald, M.D., pp. 985–1024.

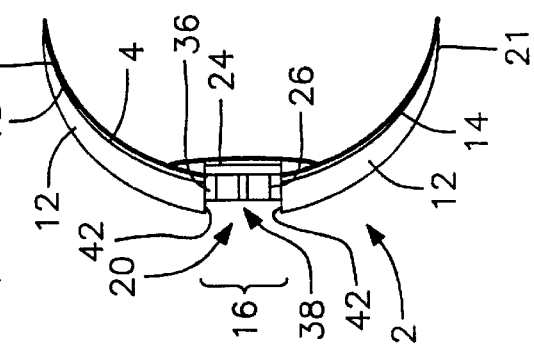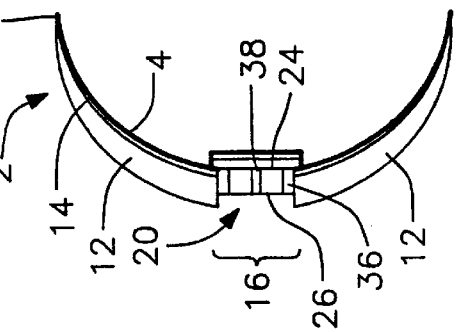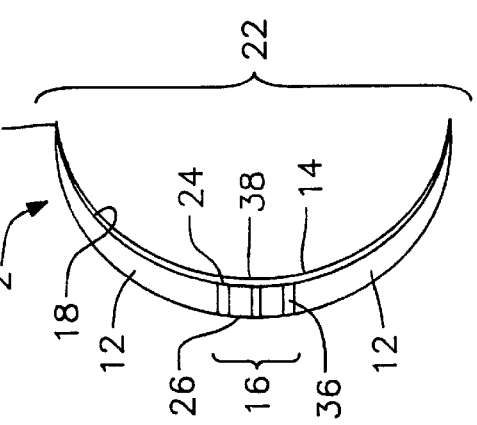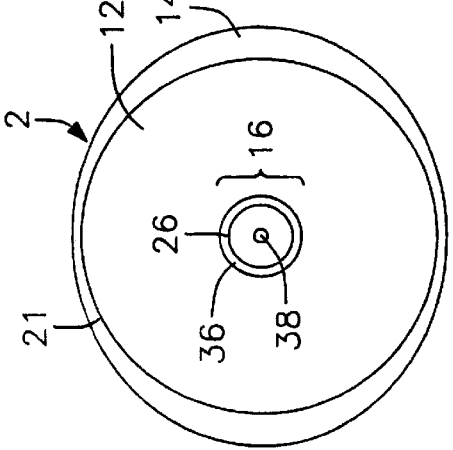

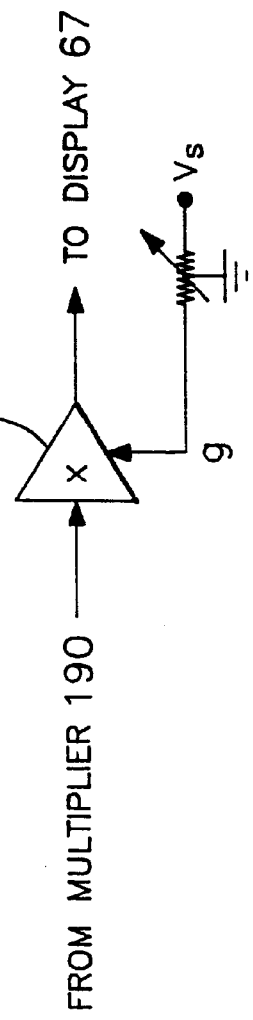
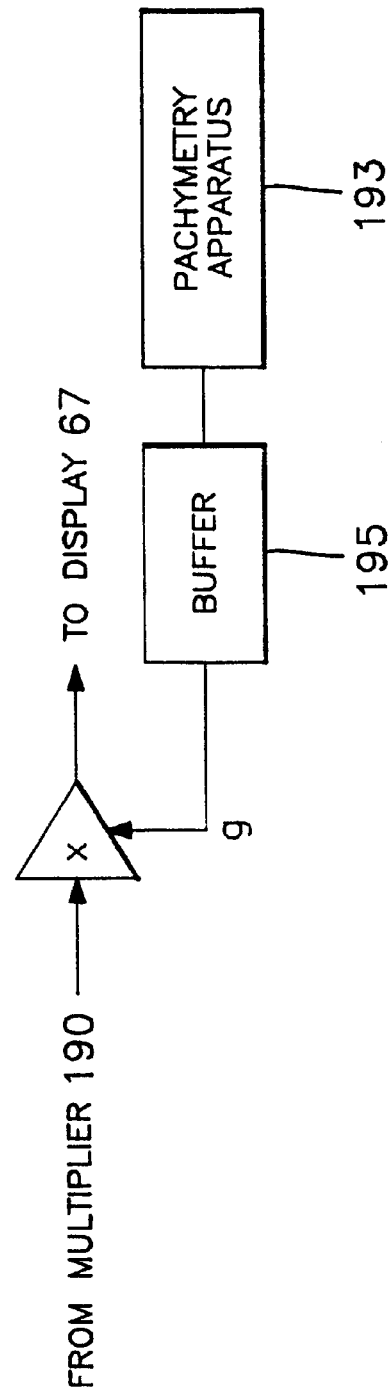

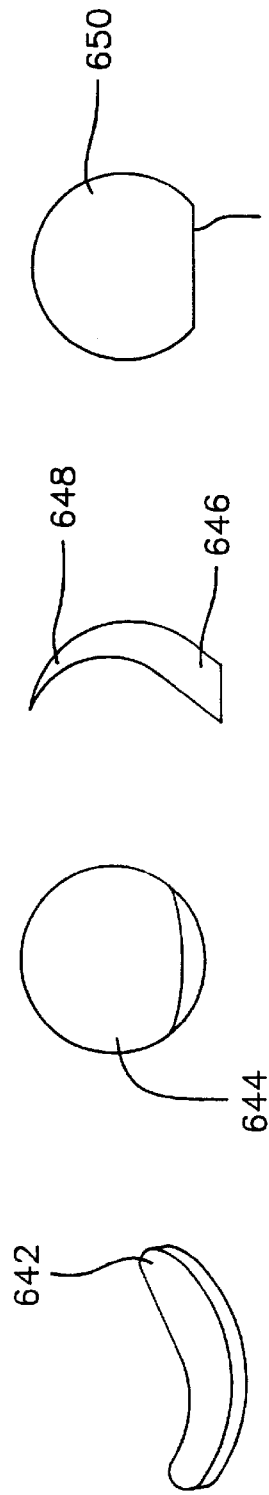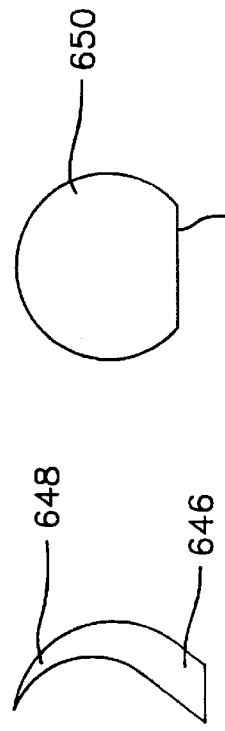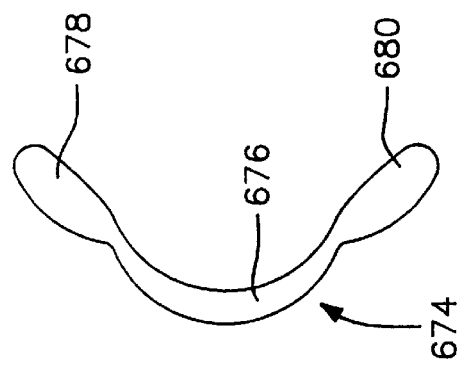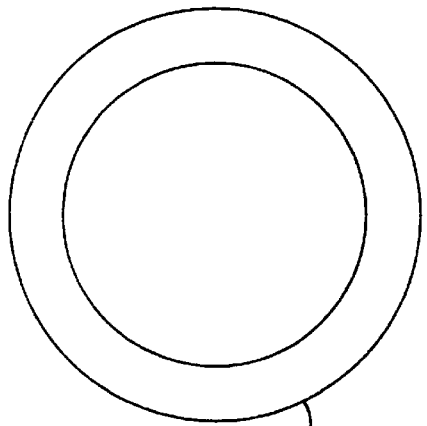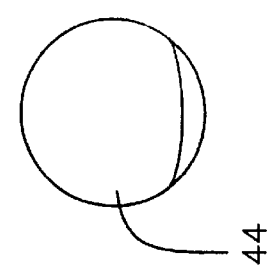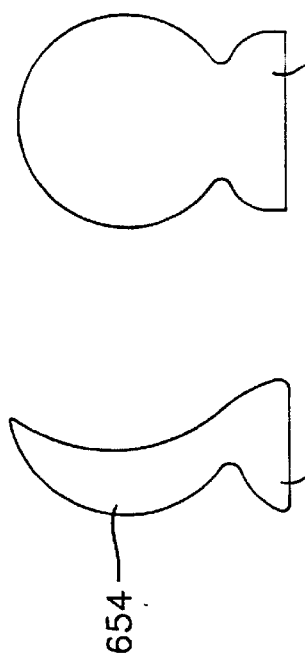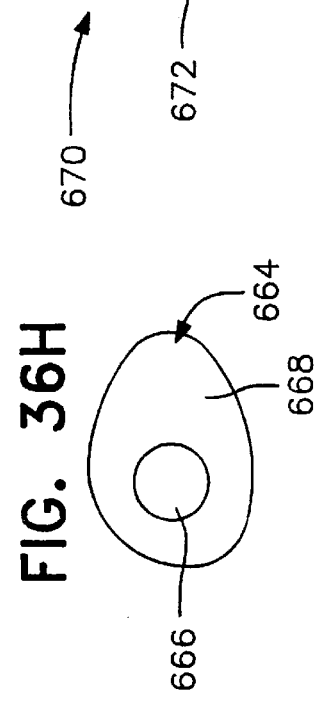

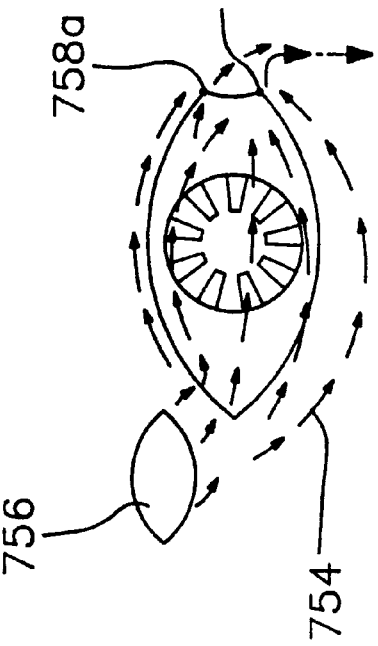
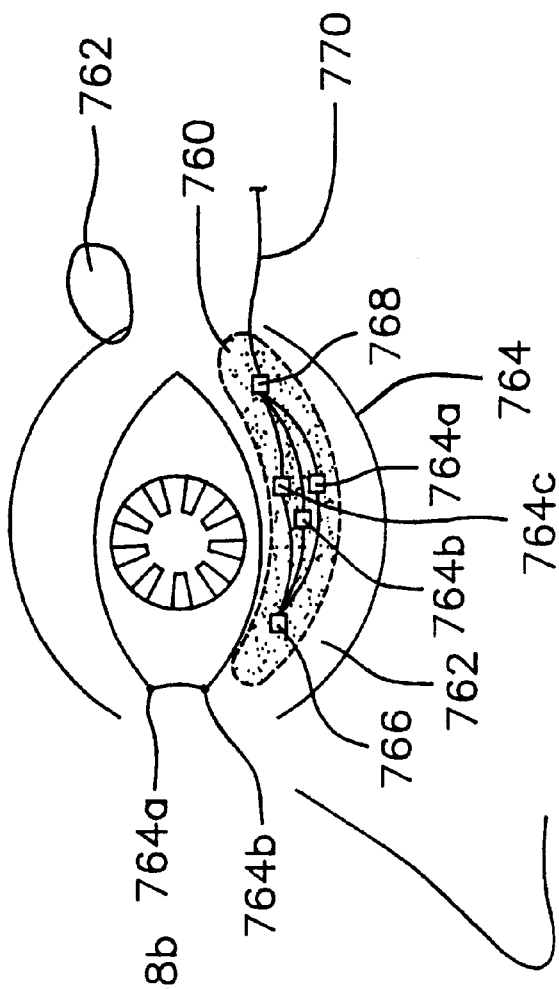
FIG. 39A
FIG. 39B

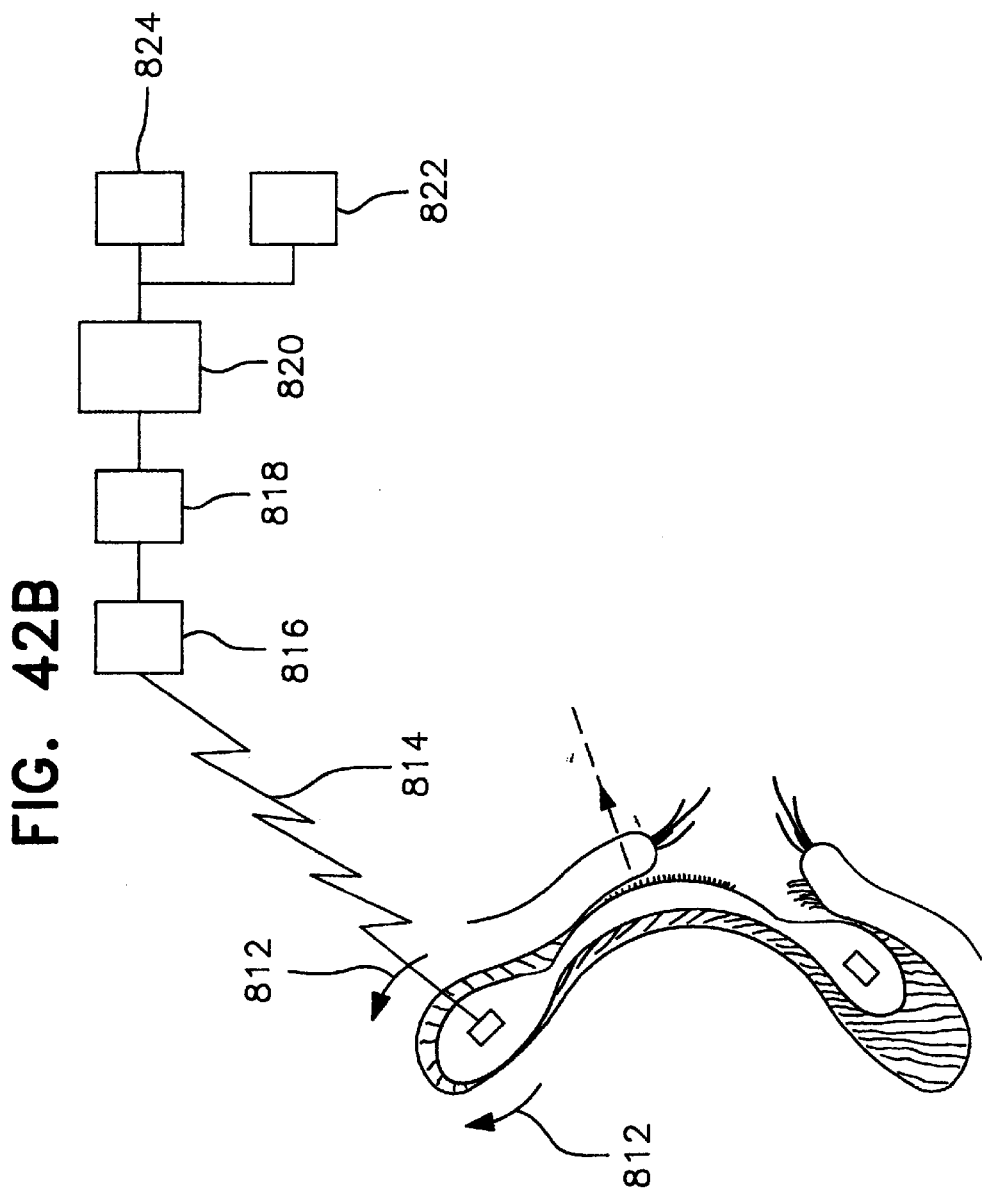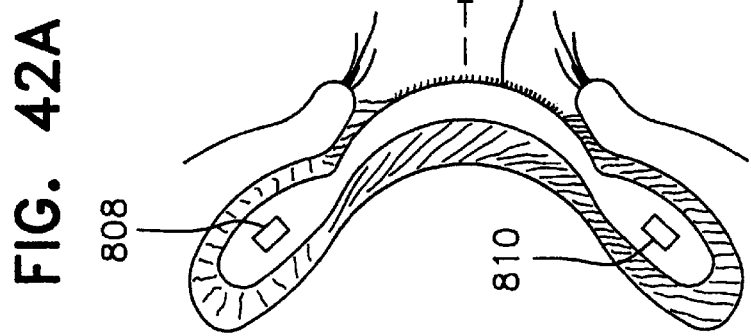

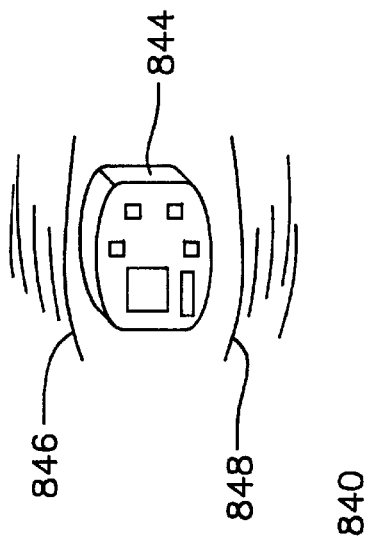
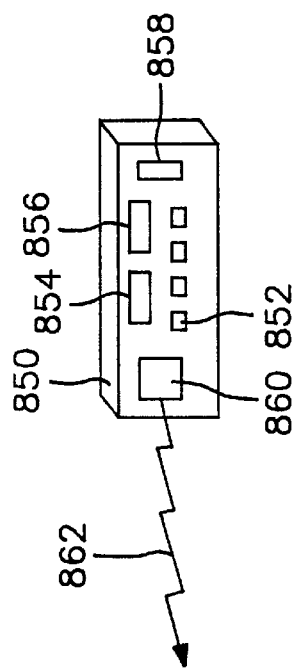
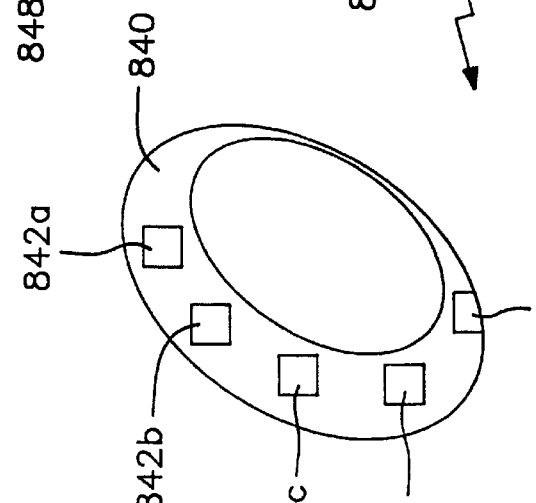
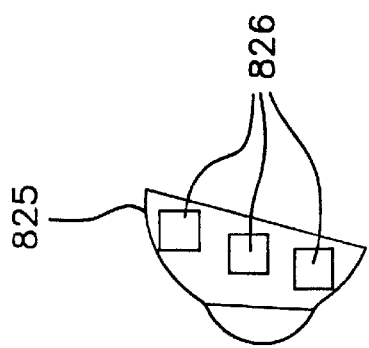
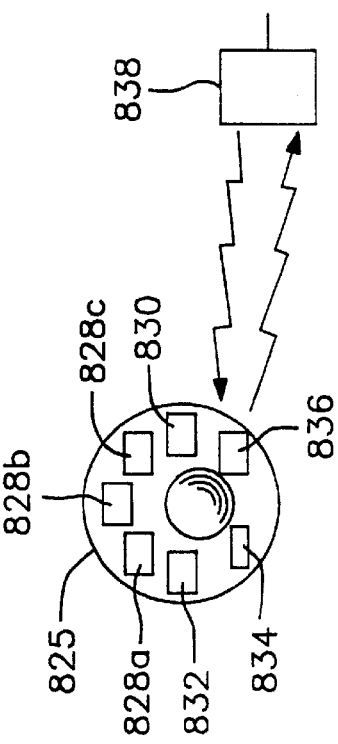

METHOD AND APPARATUS FOR SIGNAL ACQUISITION, PROCESSING AND TRANSMISSION FOR EVALUATION OF BODILY FUNCTIONS

This application is a continuing application of application Ser. No. 08/707,508, filed Sep. 4, 1996 now U.S. Pat. No. 5,830,139, incorporated herein in its entirety by references.

FIELD OF THE INVENTION

The present invention includes a contact device for mounting on a part of the body to measure bodily functions and to treat abnormal conditions indicated by the measurements.

BACKGROUND OF THE INVENTION

The present invention relates to a tonometer system for measuring intraocular pressure by accurately providing a predetermined amount of applanation to the cornea and detecting the amount of force required to achieve the predetermined amount of applanation. The system is also capable of measuring intraocular pressure by indenting the cornea using a predetermined force applied using an indenting element and detecting the distance the indenting element moves into the cornea when the predetermined force is applied, the distance being inversely proportional to intraocular pressure. The present invention also relates to a method of using the tonometer system to measure hydrodynamic characteristics of the eye, especially outflow facility.

The tonometer system of the present invention may also be used to measure hemodynamics of the eye, especially ocular blood flow and pressure in the eye's blood vessels. Additionally, the tonometer system of the present invention may be used to increase and measure the eye pressure and evaluate, at the same time, the ocular effects of the increased pressure.

Glaucoma is a leading cause of blindness worldwide and, although it is more common in adults over age 35, it can occur at any age. Glaucoma primarily arises when intraocular pressure increases to values which the eye cannot withstand.

The fluid responsible for pressure in the eye is the aqueous humor. It is a transparent fluid produced by the eye in the ciliary body and collected and drained by a series of channels (trabecular meshwork, Schlemm's canal and venous system). The basic disorder in most glaucoma patients is caused by an obstruction or interference that restricts the flow of aqueous humor out of the eye. Such an obstruction or interference prevents the aqueous humor from leaving the eye at a normal rate. This pathologic condition occurs long before there is a consequent rise in intraocular pressure. This increased resistance to outflow of aqueous humor is the major cause of increased intraocular pressure in glaucoma-stricken patients.

Increased pressure within the eye causes progressive damage to the optic nerve. As optic nerve damage occurs, characteristic defects in the visual field develop, which can lead to blindness if the disease remains undetected and untreated. Because of the insidious nature of glaucoma and the gradual and painless loss of vision associated therewith, glaucoma does not produce symptoms that would motivate an individual to seek help until relatively late in its course when irreversible damage has already occurred. As a result, millions of glaucoma victims are unaware that they have the disease and face eventual blindness. Glaucoma can be detected and evaluated by measuring the eye's fluid pressure using a tonometer and/or by measuring the eye fluid outflow facility. Currently, the most frequently used way of measuring facility of outflow is by doing indentation tonography. According to this technique, the capacity for flow is determined by placing a tonometer upon the eye. The weight of the instrument forces aqueous humor through the filtration system, and the rate at which the pressure in the eye declines with time is related to the ease with which the fluid leaves the eye.

Individuals at risk for glaucoma and individuals who will develop glaucoma generally have a decreased outflow facility. Thus, the measurement of the outflow facility provides information which can help to identify individuals who may develop glaucoma, and consequently will allow early evaluation and institution of therapy before any significant damage occurs.

The measurement of outflow facility is helpful in making therapeutic decisions and in evaluating changes that may occur with time, aging, surgery, or the use of medications to alter intraocular pressure. The determination of outflow facility is also an important research tool for the investigation of matters such as drug effects, the mechanism of action of various treatment modalities, assessment of the adequacy of antiglaucoma therapy, detection of wide diurnal swings in pressure and to study the pathophysiology of glaucoma.

There are several methods and devices available for measuring intraocular pressure, outflow facility, and/or various other glaucoma-related characteristics of the eye. The following patents disclose various examples of such conventional devices and methods:

| U.S. PAT. NO. | PATENTEE |
| --- | --- |
| 5,375,595 | Sinha et al. |
| 5,295,495 | Maddess |
| 5,251,627 | Morris |
| 5,217,015 | Kaye et al. |
| 5,183,044 | Nishio et al. |
| 5,179,953 | Kursar |
| 5,148,807 | Hsu |
| 5,109,852 | Kaye et al. |
| 5,165,409 | Coan |
| 5,076,274 | Matsumoto |
| 5,005,577 | Frenkel |
| 4,951,671 | Coan |
| 4,947,849 | Takahashi et al. |
| 4,944,303 | Katsuragi |
| 4,922,913 | Waters, Jr. et al. |
| 4,860,755 | Erath |
| 4,771,792 | Seale |
| 4,628,938 | Lee |
| 4,305,399 | Beale |
| 3,724,263 | Rose et al. |
| 3,585,849 | Grolman |
| 3,545,260 | Lichtenstein et al. |

Still other examples of conventional devices and/or methods are disclosed in Morey, Contact Lens Tonometer, RCA Technical Notes, No. 602, December 1964; Russell & Bergmanson, Multiple Applications of the NCT: An Assessment of the Instrument's Effect on IOP, Ophthal. Physiol. Opt., Vol. 9, April 1989, pp. 212–214; Moses & Grodzki, The Pneumatonograph: A Laboratory Study, Arch. Ophthalmol., Vol. 97, March 1979, pp. 547–552; and C. C. Collins, Miniature Passive Pressure Transensor for Implanting in the Eye, IEEE Transactions on Bio-medical Engineering, April 1967, pp. 74–83.

In general, eye pressure is measured by depressing or flattening the surface of the eye, and then estimating the amount of force necessary to produce the given flattening or depression. Conventional tonometry techniques using the principle of applanation may provide accurate measurements of intraocular pressure, but are subject to many errors in the way they are currently being performed. In addition, the present devices either require professional assistance for their use or are too complicated, expensive or inaccurate for individuals to use at home. As a result, individuals must visit an eye care professional in order to check their eye pressure. The frequent self-checking of intraocular pressure is useful not only for monitoring therapy and self-checking for patients with glaucoma, but also for the early detection of rises in pressure in individuals without glaucoma and for whom the elevated pressure was not detected during their office visit.

Pathogens that cause severe eye infection and visual impairment such as herpes and adenovirus as well as the virus that causes AIDS can be found on the surface of the eye and in the tear film. These microorganisms can be transmitted from one patient to another through the tonometer tip or probe. Probe covers have been designed in order to prevent transmission of diseases but are not widely used because they are not practical and provide less accurate measurements. Tonometers which prevent the transmission of diseases, such as the "air-puff" type of tonometer also have been designed, but they are expensive and provide less accurate measurements. Any conventional direct contact tonometers can potentially transmit a variety of systemic and ocular diseases.

The two main techniques for the measurement of intraocular pressure require a force that flattens or a force that indents the eye, called "applanation" and "indentation" tonometry respectively.

Applanation tonometry is based on the Imbert-Fick principle. This principle states that for an ideal dry, thin walled sphere, the pressure inside the sphere equals the force necessary to flatten its surface divided by the area of flattening. P=F/A (where P=pressure, F=force, A=area). In applanation tonometry, the cornea is flattened, and by measuring the applanating force and knowing the area flattened, the intraocular pressure is determined.

By contrast, according to indentation tonometry (Schiotz), a known weight (or force) is applied against the cornea and the intraocular pressure is estimated by measuring the linear displacement which results during deformation or indentation of the cornea. The linear displacement caused by the force is indicative of intraocular pressure. In particular, for standard forces and standard dimensions of the indenting device, there are known tables which correlate the linear displacement and intraocular pressure.

Conventional measurement techniques using applanation and indentation are subject to many errors. The most frequently used technique in the clinical setting is contact applanation using Goldman tonometers. The main sources of errors associated with this method include the addition of extraneous pressure on the cornea by the examiner, squeezing of the eyelids or excessive widening of the lid fissure by the patient due to the discomfort caused by the tonometer probe resting upon the eye, and inadequate or excessive amount of dye (fluorescein). In addition, the conventional techniques depend upon operator skill and require that the operator subjectively determine alignment, angle and amount of depression. Thus, variability and inconsistency associated with less valid measurements are problems encountered using the conventional methods and devices.

Another conventional technique involves air-puff tonometers wherein a puff of compressed air of a known volume and pressure is applied against the surface of the eye, while sensors detect the time necessary to achieve a predetermined amount of deformation in the eye's surface caused by application of the air puff. Such a device is described, for example, in U.S. Pat. No. 3,545,260 to Lichtenstein et al. Although the non-contact (air-puff) tonometer does not use dye and does not present problems such as extraneous pressure on the eye by the examiner or the transmission of diseases, there are other problems associated therewith. Such devices, for example, are expensive, require a supply of compressed gas, are considered cumbersome to operate, are difficult to maintain in proper alignment and depend on the skill and technique of the operator. In addition, the individual tested generally complains of pain associated with the air discharged toward the eye, and due to that discomfort many individuals are hesitant to undergo further measurement with this type of device. The primary advantage of the non-contact tonometer is its ability to measure pressure without transmitting diseases, but they are not accepted in general as providing accurate measurements and are primarily useful for large-scale glaucoma screening programs.

Tonometers which use gases, such as the pneumotonometer, have several disadvantages and limitations. Such device are also subject to the operator errors as with Goldman's tonometry. In addition, this device uses freon gas, which is not considered environmentally safe. Another problem with this device is that the gas is flammable and as with any other aerosol-type can, the can may explode if it gets too hot. The gas may also leak and is susceptible to changes in cold weather, thereby producing less accurate measurements. Transmission of diseases is also a problem with this type of device if probe covers are not utilized.

In conventional indentation tonometry (Schiotz), the main source of errors are related to the application of a relatively heavy tonometer (total weight at least 16.5 g) to the eye and the differences in the distensibility of the coats of the eye. Experience has shown that a heavy weight causes discomfort and raises the intraocular pressure. Moreover the test depends upon a cumbersome technique in which the examiner needs to gently place the tonometer onto the cornea without pressing the tonometer against the globe. The accuracy of conventional indentation may also be reduced by inadequate cleaning of the instrument as will be described later. The danger of transmitting infectious diseases, as with any contact tonometer, is also present with conventional indentation.

A variety of methods using a contact lens have been devised, however, such systems suffer from a number of restrictions and virtually none of these devices is being widely utilized or is accepted in the clinical setting due to their limitations and inaccurate readings. Moreover, such devices typically include instrumented contact lenses and/or cumbersome and complex contact lenses.

Several instruments in the prior art employ a contact lens placed in contact with the sclera (the white part of the eye). Such systems suffer from many disadvantages and drawbacks. The possibility of infection and inflammation is increased due to the presence of a foreign body in direct contact with a vascularized part of the eye. As a consequence, an inflammatory reaction around the device may occur, possibly impacting the accuracy of any measurement. In addition, the level of discomfort is high due to a long period of contact with a highly sensitive area of the eye. Furthermore, the device could slide and therefore lose proper alignment, and again, preventing accurate measurements to be taken. Moreover, the sclera is a thick and almost non-distensible coat of the eye which may further impair the ability to acquire accurate readings. Most of these devices utilize expensive sensors and complicated electric circuitry imbedded in the lens which are expensive, difficult to manufacture and sometimes cumbersome.

Other methods for sensing pressure using a contact lens on the cornea have been described. Some of the methods in this prior art also employ expensive and complicated electronic circuitry and/or transducers imbedded in the contact lens. In addition, some devices use piezoelectric material in the lens and the metalization of components of the lens overlying the optical axis decreases the visual acuity of patients using that type of device. Moreover, accuracy is decreased since the piezoelectric material is affected by small changes in temperature and the velocity with which the force is applied. There are also contact lens tonometers which utilize fluid in a chamber to cause the deformation of the cornea; however, such devices lack means for alignment and are less accurate, since the flexible elastic material is unstable and may bulge forward. In addition, the fluid therein has a tendency to accumulate in the lower portion of the chamber, thus failing to produce a stable flat surface which is necessary for an accurate measurement.

Another embodiment uses a coil wound about the inner surface of the contact lens and a magnet subjected to an externally created magnetic field. A membrane with a conductive coating is compressed against a contact completing a short circuit. The magnetic field forces the magnet against the eye and the force necessary to separate the magnet from the contact is considered proportional to the pressure. This device suffers from many limitations and drawbacks. For example, there is a lack of accuracy since the magnet will indent the cornea and when the magnet is pushed against the eye, the sclera and the coats of the eye distort easily to accommodate the displaced intraocular contents. This occurs because this method does not account for the ocular rigidity, which is related to the fact that the sclera of one person's eye is more easily stretched than the sciera of another. An eye with a low ocular rigidity will be measured and read as having a lower intraocular pressure than the actual eye's pressure. Conversely, an eye with a high ocular rigidity distends less easily than the average eye, resulting in a reading which is higher than the actual intraocular pressure. In addition, this design utilizes current in the lens which, in turn, is in direct contact with the body. Such contact is undesirable. Unnecessary cost and complexity of the design with circuits imbedded in the lens and a lack of an alignment system are also major drawbacks with this design.

Another disclosed contact lens arrangement utilizes a resonant circuit formed from a single coil and a single capacitor and a magnet which is movable relative to the resonant circuit. A further design from the same disclosure involves a transducer comprised of a pressure sensitive transistor and complex circuits in the lens which constitute the operating circuit for the transistor. All three of the disclosed embodiments are considered impractical and even unsafe for placement on a person's eye. Moreover, these contact lens tonometers are unnecessarily expensive, complex cumbersome to use and may potentially damage the eye. In addition none of these devices permits measurement of the applanated area, and thus are generally not very practical.

The prior art also fails to provide a sufficiently accurate technique or apparatus for measuring outflow facility. Conventional techniques and devices for measuring outflow facility are limited in practice and are more likely to produce erroneous results because both are subject to operator, patient and instrument errors.

With regard to operator errors, the conventional test for outflow facility requires a long period of time during which there can be no tilting of the tonometer. The operator therefore must position and keep the weight on the cornea without moving the weight and without pressing the globe.

With regard to patient errors, if during the test the patient blinks, squeezes, moves, holds his breath, or does not maintain fixation, the test results will not be accurate. Since conventional tonography takes about four minutes to complete and generally requires placement of a relatively heavy tonometer against the eye, the chances of patients becoming anxious and therefore reacting to the mechanical weight placed on their eyes is increased.

With regard to instrument errors, after each use, the tonometer plunger and foot plate should be rinsed with water followed by alcohol and then wiped dry with lint-free material. If any foreign material drys within the foot plate, it can detrimentally affect movement of the plunger and can produce an incorrect reading.

The conventional techniques therefore are very difficult to perform and demand trained and specialized personnel. The pneumotonograph, besides having the problems associated with the pneumotonometer itself, was considered "totally unsuited to tonography." (Report by the Committee on Standardization of Tonometers of the American Academy of Ophthalmology; Archives Ophthalmol., 97:547–552, 1979). Another type of tonometer (Non Contact "Air Puff" Tonometer-U.S. Pat. No. 3,545,260) was also considered unsuitable for tonography. (Ophthalmic & Physiological Optics, 9(2):212–214, 1989). Presently there are no truly acceptable means for self-measurement of intraocular pressure and outflow facility.

In relation to an additional embodiment of the present invention, blood is responsible not only for the transport of oxygen, nutrients, glucose, cholesterol, electrolytes, water, enzymes, white and red blood cells, and genetic markers, but also provides an enormous amount of information in regards to the overall health status of an individual. The prior art related to analysis of blood relies primarily on invasive methods such as with the use of needles to draw blood for further analysis and processing. Very few and extremely limited methods for non-invasive evaluating blood components are available.

In the prior art for example, oxygenated hemoglobin has been indirectly measured by a pulse oximeter based on traditional near infrared absorption spectroscopy and indirectly measures arterial blood oxygen carried by hemoglobin (not molecular concentration of oxygen) with sensors placed over the skin utilizing LEDs emitting at two wave lengths around 940 and 660 nanometers. As the blood oxygenation changes, the ratio of the light transmitted by the two frequencies changes indicating the amount of oxygenated hemoglobin in the arterial blood of the finger tip. The present systems are not accurate and provide only the amount of oxygenated hemoglobin in the finger tip.

SUMMARY OF THE INVENTION

In contrast to the various prior art devices, the apparatus of the present invention offers an entirely new approach for the measurement of intraocular pressure and eye hydrodynamics. The apparatus offers a simple, accurate, low-cost and safe means of detecting and measuring the earliest of abnormal changes taking place in glaucoma, and provides a method for the diagnosis of early forms of glaucoma before any irreversible damage occurs. The apparatus of this invention provides a fast, safe, virtually automatic, direct-reading, comfortable and accurate measurement utilizing an easy-to-use, gentle, dependable and low-cost device, which is suitable for home use.

Besides providing a novel method for a single measurement and self-measurement of intraocular pressure, the apparatus of the invention can also be used to measure outflow facility and ocular rigidity. In order to determine ocular rigidity it is necessary to measure intraocular pressure under two different conditions, either with different weights on the tonometer or with the indentation tonometer and an applanation tonometer. Moreover, the device can perform applanation tonography which is unaffected by ocular rigidity because the amount of deformation of the cornea is so very small that very little is displaced with very little change in pressure. Large variations in ocular rigidity, therefore, have little effect on applanation measurements.

According to the present invention, a system is provided for measuring intraocular pressure by applanation. The system includes a contact device for placement in contact with the cornea and an actuation apparatus for actuating the contact device so that a portion thereof projects inwardly against the cornea to provide a predetermined amount of applanation. The contact device is easily sterilized for multiple use, or alternatively, can be made inexpensively so as to render the contact device disposable. The present invention, therefore, avoids the danger present in many conventional devices of transmitting a variety of systemic and ocular diseases.

The system further includes a detecting arrangement for detecting when the predetermined amount of applanation of the cornea has been achieved and a calculation unit responsive to the detecting arrangement for determining intraocular pressure based on the amount of force the contact device must apply against the cornea in order to achieve the predetermined amount of applanation.

The contact device preferably includes a substantially rigid annular member, a flexible membrane and a movable central piece. The substantially rigid annular member includes an inner concave surface shaped to match an outer surface of the cornea and having a hole defined therein. The subsannular member preferably has a maximum thickness at the hole and a progressively decreasing thickness toward a periphery of the substantially rigid annular member.

The flexible membrane is preferably secured to the inner concave surface of the substantially rigid annular member. The flexible membrane is coextensive with at least the hole in the annular member and includes at least one transparent area. Preferably, the transparent area spans the entire flexible membrane, and the flexible membrane is coextensive with the entire inner concave surface of the rigid annular member.

The movable central piece is slidably disposed within the hole and includes a substantially flat inner side secured to the flexible membrane. A substantially cylindrical wall is defined circumferentially around the hole by virtue of the increased thickness of the rigid annular member at the periphery of the hole. The movable central piece is preferably slidably disposed against this wall in a piston-like manner and has a thickness which matches the height of the cylindrical wall. In use, the substantially flat inner side flattens a portion of the cornea upon actuation of the movable central piece by the actuation apparatus.

Preferably, the actuation apparatus actuates the movable central piece to cause sliding of the movable central piece in the piston-like manner toward the cornea. In doing so, the movable central piece and a central portion of the flexible membrane are caused to project inwardly against the cornea. A portion of the cornea is thereby flattened. Actuation continues until a predetermined amount of applanation is achieved.

Preferably, the movable central piece includes a magnetically responsive element arranged so as to slide along with the movable central piece in response to a magnetic field, and the actuation apparatus includes a mechanism for applying a magnetic field thereto. The mechanism for applying the magnetic field preferably includes a coil and circuitry for producing an electrical current through the coil in a progressively increasing manner. By progressively increasing the current, the magnetic field is progressively increased. The magnetic repulsion between the actuation apparatus and the movable central piece therefore increases progressively, and this, in turn, causes a progressively greater force to be applied against the cornea until the predetermined amount of applanation is achieved.

Using known principles of physics, it is understood that the electrical current passing through the coil will be proportional to the amount of force applied by the movable central piece against the cornea via the flexible membrane. Since the amount of force required to achieve the predetermined amount of applanation is proportional to intraocular pressure, the amount of current required to achieve the predetermined amount of applanation will also be proportional to the intraocular pressure.

The calculation unit therefore preferably includes a memory for storing a current value indicative of the amount of current passing through the coil when the predetermined amount of applanation is achieved and also includes a conversion unit for converting the current value into an indication of intraocular pressure.

The magnetically responsive element is circumferentially surrounded by a transparent peripheral portion. The transparent peripheral portion is aligned with the transparent area and permits light to pass through the contact device to the cornea and also permits light to reflect from the cornea back out of the contact device through the transparent peripheral portion.

The magnetically responsive element preferably comprises an annular magnet having a central sight hole through which a patient is able to see while the contact device is located on the patient's cornea. The central sight hole is aligned with the transparent area of the flexible membrane.

A display is preferably provided for numerically displaying the intraocular pressure detected by the system. Alternatively, the display can be arranged so as to give indications of whether the intraocular pressure is within certain ranges.

Preferably, since different patients may have different sensitivities or reactions to the same intraocular pressure, the ranges are calibrated for each patient by an attending physician. This way, patients who are more susceptible to consequences from increased intraocular pressure may be alerted to seek medical attention at a pressure less than the pressure at which other less-susceptible patients are alerted to take the same action.

The detecting arrangement preferably comprises an optical applanation detection system. In addition, a sighting arrangement is preferably provided for indicating when the actuation apparatus and the detecting arrangement are properly aligned with the contact device. Preferably, the sighting arrangement includes the central sight hole in the movable central piece through which a patient is able to see while the device is located on the patient's cornea. The central sight hole is aligned with the transparent area, and the patient preferably achieves a generally proper alignment by directing his vision through the central sight hole toward a target mark in the actuation apparatus.

The system also preferably includes an optical distance measuring mechanism for indicating whether the contact device is spaced at a proper axial distance from the actuation apparatus and the detecting arrangement. The optical distance measurement mechanism is preferably used in conjunction with the sighting arrangement and preferably provides a visual indication of what corrective action should be taken whenever an improper distance is detected.

The system also preferably includes an optical alignment mechanism for indicating whether the contact device is properly aligned with the actuation apparatus and the detecting arrangement. The optical alignment mechanism preferably provides a visual indication of what corrective action should be taken whenever a misalignment is detected, and is preferably used in conjunction with the sighting arrangement, so that the optical alignment mechanism merely provides indications of minor alignment corrections while the sighting arrangement provides an indication of major alignment corrections.

In order to compensate for deviations in corneal thickness, the system of the present invention may also include an arrangement for multiplying the detected intraocular pressure by a coefficient (or gain) which is equal to one for corneas of normal thickness, less than one for unusually thick corneas, and a gain greater than one for unusually thin corneas.

Similar compensations can be made for corneal curvature, eye size, ocular rigidity, and the like. For levels of corneal curvature which are higher than normal, the coefficient would be less than one. The same coefficient would be greater than one for levels of corneal curvature which are flatter than normal.

In the case of eye size compensation, larger than normal eyes would require a coefficient which is less than one, while smaller than normal eyes require a coefficient which is greater than one.

For patients with "stiffer" than normal ocular rigidities, the coefficient is less than one, but for patients with softer ocular rigidities, the coefficient is greater than one.

The coefficient (or gain) may be manually selected for each patient, or alternatively, the gain may be selected automatically by connecting the apparatus of the present invention to a known pachymetry apparatus when compensating for corneal thickness, a known keratometer when compensating for corneal curvature, and/or a known biometer when compensating for eye size.

The contact device and associated system of the present invention may also be used to detect intraocular pressure by indentation. When indentation techniques are used in measuring intraocular pressure, a predetermined force is applied against the cornea using an indentation device. Because of the force, the indentation device travels in toward the cornea, indenting the cornea as it travels. The distance traveled by the indentation device into the cornea in response to the predetermined force is known to be inversely proportional to intraocular pressure. Accordingly, there are various known tables which, for certain standard sizes of indentation devices and standard forces, correlate the distance traveled and intraocular pressure.

Preferably, the movable central piece of the contact device also functions as the indentation device. In addition, the circuit is switched to operate in an indentation mode. When switched to the indentation mode, the current producing circuit supplies a predetermined amount of current through the coil. The predetermined amount of current corresponds to the amount of current needed to produce one of the aforementioned standard forces.

In particular, the predetermined amount of current creates a magnetic field in the actuation apparatus. This magnetic field, in turn, causes the movable central piece to push inwardly against the cornea via the flexible membrane. Once the predetermined amount of current has been applied and a standard force presses against the cornea, it is necessary to determine how far the movable central piece moved into the cornea.

Accordingly, when measurement of intraocular pressure by indentation is desired, the system of the present invention further includes a distance detection arrangement for detecting a distance traveled by the movable central piece, and a computation portion in the calculation unit for determining intraocular pressure based on the distance traveled by the movable central piece in applying the predetermined amount of force.

Preferably, the computation portion is responsive to the current producing circuitry so that, once the predetermined amount of force is applied, an output voltage from the distance detection arrangement is received by the computation portion. The computation portion then, based on the displacement associated with the particular output voltage, determines intraocular pressure.

In addition, the present invention includes alternative embodiments, as will be described hereinafter, for performing indentation-related measurements of the eye. Clearly, therefore, the present invention is not limited to the aforementioned exemplary indentation device.

The aforementioned indentation device of the present invention may also be utilized to non-invasively measure hydrodynamics of an eye including outflow facility. The method of the present invention preferably comprises several steps including the following:

According to a first step, an indentation device is placed in contact with the cornea. Preferably, the indentation device comprises the contact device of the present invention.

Next, at least one movable portion of the indentation device is moved in toward the cornea using a first predetermined amount of force to achieve indentation of the cornea. An intraocular pressure is then determined based on a first distance traveled toward the cornea by the movable portion of the indentation device during application of the first predetermined amount of force. Preferably, the intraocular pressure is determined using the aforementioned system for determining intraocular pressure by indentation.

Next, the movable portion of the indentation device is rapidly reciprocated in toward the cornea and away from the cornea at a first predetermined frequency and using a second predetermined amount of force during movement toward the cornea to thereby force intraocular fluid out from the eye. The second predetermined amount of force is preferably equal to or more than the first predetermined amount of force. It is understood, however, that the second predetermined amount of force may be less than the first predetermined amount of force.

The movable portion is then moved in toward the cornea using a third predetermined amount of force to again achieve indentation of the cornea. A second intraocular pressure is then determined based on a second distance traveled toward the cornea by the movable portion of the indentation device during application of the third predetermined amount of force. Since intraocular pressure decreases as a result of forcing intraocular fluid out of the eye during the rapid reciprocation of the movable portion, it is generally understood that, unless the eye is so defective that no fluid flows out therfrom, the second intraocular pressure will be less than the first intraocular pressure. This reduction in intraocular pressure is indicative of outflow facility.

Next, the movable portion of the indentation device is again rapidly reciprocated in toward the cornea and away from the cornea, but at a second predetermined frequency and using a fourth predetermined amount of force during movement toward the cornea. The fourth predetermined amount of force is preferably equal to or greater than the second predetermined amount of force; however, it is understood that the fourth predetermined amount of force may be less than the second predetermined amount of force. Additional intraocular fluid is thereby forced out from the eye.

The movable portion is subsequently moved in toward the cornea using a fifth predetermined amount of force to again achieve indentation of the cornea. Thereafter, a third intraocular pressure is determined based on a third distance traveled toward the cornea by the movable portion of the indentation device during application of the fifth predetermined amount of force.

The differences are then preferably calculated between the first, second, and third distances, which differences are indicative of the volume of intraocular fluid which left the eye and therefore are also indicative of the outflow facility. It is understood that the difference between the first and last distances may be used, and in this regard, it is not necessary to use the differences between all three distances. In fact, the difference between any two of the distances will suffice.

Although the relationship between the outflow facility and the detected differences varies when the various parameters of the method and the dimensions of the indentation device change, the relationship for given parameters and dimensions can be easily determined by known experimental techniques and/or using known Friedenwald Tables.

Preferably, the method further comprises the steps of plotting the differences between the first, second, and third distance to a create a graph of the differences and comparing the resulting graph of differences to that of a normal eye to determine if any irregularities in outflow facility are present.

Additionally, the present invention relates to the utilization of a contact device placed on the front part of the eye in order to detect physical and chemical parameters of the body as well as the non-invasive delivery of compounds according to these physical and chemical parameters, with signals preferably being transmitted continuously as electromagnetic waves, radio waves, infrared and the like. One of the parameters to be detected includes non-invasive blood analysis utilizing chemical changes and chemical products that are found in the front part of the eye and in the tear film. The non-invasive blood analysis and other measurements are done using the system of my co-pending prior application, characterized as an intelligent contact lens system.

The word lens is used here to define an eyepiece which fits inside the eye regardless of the presence of optical properties for correction of imperfect vision. The word intelligent used here defines a lens capable of signal-detection and/or signal-transmission and/or signal-reception and/or signal-emission and/or signal-processing and analysis as well as the ability to alter physical, chemical, and or biological variables. When the device is placed in other parts of the body other than the eye, it is referred to as a contact device or intelligent contact device (ICD).

An alternative embodiment of the present invention will now be described. The apparatus and method is based on a different and novel concept originated by the inventor in which a transensor mounted in the contact device laying on the cornea or the surface of the eye is capable of evaluating and measuring physical and chemical parameters in the eye including non-invasive blood analysis. The alternative embodiment preferably utilizes a transensor mounted in the contact device which is preferably laying in contact with the surface of the eye and is preferably activated by the process of eye lid motion and/or closure of the eye lid. The system preferably utilizes eye lid motion and/or closure of the eye lid to activate a microminiature radio frequency sensitive transensor mounted in the contact device. The signal can be communicated by cable, but is preferably actively or passively radio telemetered to an externally placed receiver. The signal can then be processed, analyzed and stored.

This eye lid force and motion toward the surface of the eye is also capable to create the deformation of any transensor/electrodes mounted on the contact device. During blinking, the eye lids are in full contact with the contact device and the transensor's surface is in contact with the cornea/tear film and/or inner surface of the eye lid and/or blood vessels on the surface of the conjunctiva. It is understood that the transensor used for non-invasive blood analysis is continuously activated when placed on the eye and do not need closure of the eyelid for activation. It is understood that after a certain amount of time the contact device will adhere to tissues in the conjunctiva optimizing flow of tissue fluid to sensors for measurement of blood components.

The present invention includes apparatus and methods that utilizes a contact device laying on the surface of the eye called intelligent contact lens (ICL) which provides means for transmitting physiologic, physical, and chemical information from one location as for instance living tissue on the surface of the eye to another remote location accurately and faithfully reproducing the event at the receiver. In my prior copending application, the whole mechanism by which the eye lid activate transensors is described and a microminiature passive pressure-sensitive radio frequency transducer is disclosed to continuously measure intraocular pressure and eye fluid outflow facility with both open and closed eyes.

The present invention provides a new method and apparatus to detect physical and chemical parameters of the body and the eye utilizing a contact device placed on the eye with signals being transmitted continuously as electromagnetic waves, radio waves, sound waves, infrared and the like. Several parameters can be detected with the invention including a complete non-invasive analysis of blood components, measurement of systemic and ocular blood flow, measurement of heart rate and respiratory rate, tracking operations, detection of ovulation, detection of radiation and drug effects, diagnosis of ocular and systemic disorders and the like. The invention also provides a new method and apparatus for somnolence awareness, activation of devices by disabled individuals, a new drug delivery system and new therapy for ocular and neurologic disorders, and treatment of cancer in the eye or other parts of the body, and an evaluation system for the overall health status of an individual. The device of the present invention quantifies non-invasively the amount of the different chemical components in the blood using a contact device with suitable electrodes and membranes laying on the surface of the eye and in direct contact with the tear film or surface of the eye, with the data being preferably transmitted utilizing radio waves, but alternatively sound waves, light waves, wire, or telephone lines can be used for transmission.

The system comprises a contact device in which a microminiature radio frequency transensor, actively or passively activated, such as endoradiosondes, are mounted in the contact device which in turn is preferably placed on the surface of the eye. A preferred method involves small passive radio telemetric transducers capable of detecting chemical compounds, electrolytes, glucose, cholesterol, and the like on the surface of the eye. Besides using passive radio transmission or communication by cable, active radio transmission with active transmitters contained a microminiature battery mounted in the contact device can also be used.

Several means and transensors can be mounted in the contact device and used to acquire the signal. Active radio transmitters using transensors which are energized by batteries or using cells that can be recharged in the eye by an external oscillator, and active transmitters which can be powered from a biologic source can also be used and mounted in the contact device. The preferred method to acquire the signal involves passive radio frequency transensors, which contain no power source. They act from energy supplied to it from an external source. The transensor transmits signals to remote locations using different frequencies indicative of the levels of chemical and physical parameters. These intraocular recordings can then be transmitted to remote extra ocular radio frequency monitor stations with the signal sent to a receiver for amplification and analysis. Ultrasonic micro-circuits can also be mounted in the contact device and modulated by sensors which are capable of detecting chemical and physical changes in the eye. The signal may be transmitted using modulated sound signals particularly under water because sound is less attenuated by water than are radio waves. The sonic resonators can be made responsive to changes in temperature and voltage which correlate to the presence and level of molecules such as glucose and ions in the tear film.

Ocular and systemic disorders may cause a change in the pH, osmolarity, and temperature of the tear film or surface of the eye as well as change in the tear film concentration of substances such as acid-lactic, glucose, lipids, hormones, gases, enzymes, inflammatory mediators, plasmin, albumin, lactoferrin, creatinin, proteins and so on. Besides pressure, outflow facility, and other physical characteristics of the eye, the apparatus of the invention is also capable of measuring the above physiologic parameters in the eye and tear film using transensor/electrodes mounted in the contact device. These changes in pressure, temperature, pH, oxygen level, osmolality, concentration of chemicals, and so on can be monitored with the eyes opened or closed or during blinking. In some instance such as with the evaluation of pH, metabolites, and oxygen concentration, the device does not need necessarily eye lid motion because just the contact with the transensor mounted in the contact device is enough to activate the transensor/electrodes.

The presence of various chemical elements, gases, electrolytes, and pH of the tear film and the surface of the eye can be determined by the use of suitable electrodes and a suitable permeable membrane. These electrodes, preferably microelectrodes, can be sensitized by several reacting chemicals which are in the tear film or the surface of the eye, in the surface of the cornea or preferably the vascularized areas in the surface of the eye. The different chemicals and substances diffuse through suitable permeable membranes sensitizing suitable sensors. Electrodes and sensors to measure the above compounds are available from several manufacturers.

The level of oxygen can be measured in the eye with the contact device, and in this case just the placement of the contact device would be enough to activate the system and eye lid motion and/or closure of the eye lid may not be necessary for its operation. Reversible mechanical expansion methods, photometric, or electrochemical methods and electrodes can be mounted in the device and used to detect acidity and gases concentration. Oxygen gas can also be evaluated according to its magnetic properties or be analyzed by micro-polarographic sensors mounted in the contact device. Moreover, the same sensor can measure different gases by changing the cathode potential. Carbon dioxide, carbon monoxide, and other gases can also be detected in a similar fashion.

Microminiature glass electrodes mounted in the contact device can be used to detect divalent cations such as calcium, as well as sodium and potassium ion and pH. Chloride-ion detector can be used to detect the salt concentration in the tear film and the surface of the eye. The signal can be radio transmitted to a receiver and then to a screen for continuous recording and monitoring. This allows for the continuous non-invasive measurement of electrolytes, chemicals and pH in the body and can be very useful in the intensive care unit setting.

A similar transensor can also be placed not in the eye, but in contact with other mucosas and secretions in the body, such as the oral mucosa, and the concentration of chemicals measured in the saliva or even sweat or any other body secretion with signals being transmitted to a remote location via ultrasonic or radio waves and the like. However, due to the high concentration of enzymes in the saliva and in other secretion, the electrodes and electronics could be detrimentally affected which would impact accuracy. Furthermore, there is a weak correlation between concentration of chemicals in body secretions and blood.

The tear fluid proves to be the most reliable location and indicator of the concentration of chemicals, both organic and inorganic, but other areas of the eye can be utilized to measure the concentration of chemicals. The tear fluid and surface of the eye are the preferred location for these measurements because the tear film and aqueous humor (which can be transmitted through the intact cornea) can be considered an ultrafiltrate of the plasma.

The apparatus and method of the present invention allows the least traumatic way of measuring chemicals in the body without the need of needle stick and the manipulation of blood. For instance, this may be particularly important as compared to drawing blood from infants because the results provided by the drawn blood sample may not be accurate. There is a dramatic change in oxygen and carbon dioxide levels because of crying, breath holding and even apnea spells that occur during the process of restraining the baby and drawing blood. Naturally, the ability to painlessly measure blood components without puncturing the vessel is beneficial also to any adult who needs a blood work-up, patients with diabetes who need to check their glucose level on a daily basis, and health care workers who would be less exposed to severe diseases such as AIDS and hepatitis when manipulating blood. Patients in intensive care units would benefit by having a continuous painless monitoring of electrolytes, gases, and so on by non-invasive means using the intelligent contact lens system. Moreover, there is no time wasted transporting the blood sample to the laboratory, the data is available immediately and continuously.

The different amounts of eye fluid encountered in the eye can be easily quantified and the concentration of substances calibrated according to the amount of fluid in the eye. The relationship between the concentration of chemical substances and molecules in the blood and the amount of said chemical substances in the tear fluid can be described mathematically and programmed in a computer since the tear film can be considered an ultrafiltrate of the plasma and diffusion of chemicals from capillaries on the surface of the eye have a direct correspondence to the concentration in the blood stream.

Furthermore, when the eyes are closed there is an equilibrium between the aqueous humor and the tear fluid allowing measurement of glucose in a steady state and since the device can send signals through the intervening eyelid, the glucose can be continuously monitored in this steady state condition. Optical sensors mounted in the contact device can evaluate oxygen and other gases in tissues and can be used to detect the concentration of compounds in the surface of the eye and thus not necessarily have to use the tear film to measure the concentration of said substances. In all instances, the signals can be preferably radio transmitted to a monitoring station. Optical, acoustic, electromagnetic, micro-electromechanical systems and the like can be mounted in the contact device and allow the measurement of blood components in the tear film, surface of the eye, conjunctival vessels, aqueous humor, vitreous, and other intraocular and extraocular structures.

Any substance present in the blood can be analyzed in this way since as mentioned the fluid measured is a filtrate of the blood. Rapidly responding microelectrodes with very thin membranes can be used to measure these substances providing a continuous evaluation. For example, inhaled anesthetics become blood gases and during an experiment the concentration of anesthetics present in the blood could be evaluated in the eye fluid. Anesthetics such as nitrous oxide and halothane can be reduced electrochemically at noble metal electrodes and the electrodes can be mounted in the contact device. Oxygen sensors can also be used to measure the oxygen of the sample tear film. Measurement of oxygen and anesthetics in the blood has been performed and correlated well with the amount of the substances in the eye fluid with levels in the tear fluid within 85–95% of blood levels. As can be seen, any substances not only the ones naturally present, but also artificially inserted in the blood can be potentially measured in the eye fluid. A correction factor may be used to account for the differences between eye fluid and blood. In addition, the non-invasive measurement and detection by the ICL of exogenous substances is a useful tool to law enforcement agents for rapidly testing and detecting drugs and alcohol.

The evaluation of systemic and ocular hemodynamics can be performed with suitable sensors mounted in the contact device. The measurements of blood pulsations in the eye can be done through electrical means by evaluating changes in impedance. Blood flow rate can be evaluated by several techniques including but not limited to ultrasonic and electromagnetic meters and the signals then radio transmitted to an externally placed device. For the measurement of blood flow, the contact device is preferably placed in contact with the conjunctiva, either bulbar or palpebral, due to the fact that the cornea is normally an avascular structure. Changing in the viscosity of blood can also be evaluated from a change in damping on a vibrating quartz micro-crystal mounted in the contact device.

The apparatus of the invention may also measure dimension such as the thickness of the retina, the amount of cupping in the optic nerve head, and so on by having a microminiature ultrasound device mounted in the contact device and placed on the surface of the eye. Ultra sonic timer/exciter integrated circuits used in both continuous wave and pulsed bidirectional Doppler blood flowmeters are in the order few millimeters in length and can be mounted in the apparatus of the invention.

For the measurement of hemodynamics, the contact device should preferably be placed in contact with the conjunctiva and on top of a blood vessel. Doppler blood microflowmeters are available and continuous wave (CW) and pulsed Doppler instruments can be mounted in the contact device to evaluate blood flow and the signal radio transmitted to an external receiver. The Doppler flowmeters may also use ultrasonic transducers and these systems can be fabricated in miniature electronic packages and mounted in the contact device with signals transmitted to a remote receiver.

Illumination of vessels, through the pupil, in the back of the eye can be used to evaluate blood flow velocity and volume or amount of cupping (recess) in the optic nerve head. For this use the contact device has one or more light sources located near the center and positioned in a way to reach the vessels that exit the optic nerve head, which are the vessels of largest diameter on the surface of the retina. A precise alignment of beam is possible because the optic nerve head is situated at a constant angle from the visual axis. Sensors can be also positioned on the opposite side of the illumination source and the reflected beam reaching the sensor. Multioptical filters can be housed in the contact device with the light signal converted to voltage according to the angle of incidence of reflected light. Moreover, the intracranial pressure could be indirectly estimated by the evaluation of changes and swelling in the retina and optic nerve head that occurs in these structures due to the increased intracerebral pressure.

Fiber optics from an external light source or light sources built in the contact device can emit a beam of plane-polarized light from one side at three o'clock position with the beam entering through the cornea and passing through the aqueous humor and exiting at the nine o'clock position to reach a photodetector. Since glucose can rotate the plane of polarization, the amount of optical rotation would be compared to a second reference beam projected in the same manner but with a wavelength that it is insensitive to glucose with the difference being indicative of the amount of glucose present in the aqueous humor which can be correlated to plasma glucose by using a correction factor.

A dielectric constant of several thousand can be seen in blood and a microminiature detector placed in the contact device can identify the presence of blood in the surface of the cornea. Moreover, blood causes the decomposition of hydrogen peroxide which promotes an exothermic reaction that can be sensed with a temperature-sensitive transensor. Small lamps energized by an external radio-frequency field can be mounted in the contact device and photometric blood detectors can be used to evaluate the presence of blood and early detection of neovascularization in different parts of the eye and the body.

A microminiature microphone can be mounted in the contact device and sounds from the heart, respiration, flow, vocal and the environment can be sensed and transmitted to a receiver. In cases of abnormal heart rhythm, the receiver would be carried by the individual and will have means to alert the individual through an alarm circuit either by light or sound signals of the abnormality present. Changes in heart beat can be detected and the patient alerted to take appropriate action.

The contact device can also have elements which produce and radiate recognizable signals and this procedure could be used to locate and track individuals, particularly in military operations. A permanent magnet can also be mounted in the contact device and used for tracking as described above.

Life threatening injuries causing change in heart rhythm and respiration can be detected since the cornea pulsates according to heartbeat. Motion sensitive microminiature radio frequency transensors can be mounted in the contact device and signals indicative of injuries can be radio transmitted to a remote station particularly for monitoring during combat in military operations.

In rocket or military operations or in variable g situations, the parameters above can be measured and monitored by utilizing materials in the transensor such as light aluminum which are less sensitive to gravitational and magnetic fields. Infrared emitters can be mounted in the contact device and used to activate distinct photodetectors by ocular commands such as in military operations where fast action is needed without utilizing hand movement.

Spinal cord injuries have lead thousands of individuals to complete confinement in a wheel chair. The most unfortunate situation occurs with quadriplegic individuals who virtually only have useful movement of their mouth and eyes. The apparatus of the invention allows these individuals to use their remaining movement ability to become more independent and capable of indirect manipulation of a variety of hardware. In this embodiment, the ICL uses blinking or closure of the eyes to activate remotely placed receptor photodiodes through the activation of an LED drive coupled with a pressure sensor.

The quadriplegic patient focuses on a receptor photo diode and closes their eyes for 5 seconds, for example. The pressure exerted by the eyelid is sensed by the pressure sensor which is coupled with a timing chip. If the ICL is calibrated for 5 sec, after this amount of time elapses with eyes closed, the LED drive activates the LED which emits infrared light though the intervening eyelid tissue reaching suitable receptor photodiodes or suitable optical receivers connected to a power on or off circuit. This allows quadriplegics to turn on, turn off, or manipulate a variety of devices using eye motion. It is understood that an alternative embodiment can use more complex integrated circuits connected by fine wires to the ICL placed on the eye in order to perform more advanced functions such as using LED's of different wavelengths.

Another embodiment according to the present invention includes a somnolence alert device using eye motion to detect premonitory signs of somnolence related to a physiologic condition called Bell phenomena in which the eye ball moves up and slightly outwards when the eyes are closed. Whenever an individual starts to fall asleep, the eye lid comes down and the eyes will move up.

A motion or pressure sensor mounted in the superior edge of the ICL will cause, with the Bell phenomena, a movement of the contact device upwards. This movement of the eye would position the pressure sensitive sensor mounted in the contact device against the superior cul-de-sac and the pressure created will activate the sensor which modulates a radio transmitter. The increase in pressure can be timed and if the pressure remains increased for a certain length of time indicating closed eyes, an alarm circuit is activated. The signal would then be transmitted to a receiver coupled with an alarm circuit and speaker creating a sound signal to alert the individual at the initial indication of falling asleep. Alternatively, the pressure sensor can be positioned on the inferior edge of the ICL and the lack of pressure in the inferiorly placed sensor would activate the circuit as described above.

It is also understood that other means to activate a circuit in the contact device such as closing an electric circuit due to motion or pressure shift in the contact device which remotely activate an alarm can be used as a somnolence awareness device. It is also understood that any contact device with sensing elements capable of sensing Bell phenomena can be used as a somnolence awareness device. This system, device and method are an important tool in diminishing car accidents and machinery accidents by individuals who fall sleep while operating machinery and vehicles.

If signs of injury in the eye are detected, such as increased intraocular pressure (IOP), the system can be used to release medication which is placed in the cul-de-sac in the lower eye lid as a reservoir or preferably the contact lens device acts as a reservoir for medications. A permeable membrane, small fenestrations or a valve like system with micro-gates, or micro-electronic systems housed in the contact device structure could be electrically, magnetically, electronically, or optically activated and the medication stored in the contact device released. The intelligent lenses can thus be used as non-invasive drug delivery systems. Chemical composition of the tear film, such as the level of electrolytes or glucose, so that can be sensed and signals radio transmitted to drug delivery pumps carried by the patient so that medications can be automatically delivered before symptoms occur.

A part of the contact transducer can also be released, for instance if the amount of enzymes increases. The release of part of the contact device could be a reservoir of lubricant fluid which will automatically be released covering the eye and protecting it against the insulting element. Any drugs could be automatically released in a similar fashion or through transmission of signal to the device.

An alternative embodiment includes the contact device which has a compartment filled with chemical substances or drugs connected to a thread which keeps the compartments sealed. Changes in chemicals in the tear fluid or the surface of the eye promote voltage increases which turns on a heater in the circuit which melts the thread allowing discharge of the drug housed in the compartment such as insulin if there is an increase in the levels of glucose detected by the glucose sensor.

To measure temperature, the same method and apparatus applies, but in this case the transmitter is comprised of a temperature-sensitive element. A microminiature temperature-sensitive radio frequency transensor, such as thermistor sensor, is mounted in the contact device which in turn is placed on the eye with signals preferably radio transmitted to a remote station. Changes in temperature and body heat correlate with ovulation and the thermistor can be mounted in the contact device with signals telemetered to a remote station indicating optimum time for conception.

The detection and transmission to remote stations of changes in temperature can be used on animals for breeding purposes. The intelligent contact lens can be placed on the eye of said animals and continuous monitoring of ovulation achieved. When this embodiment is used, the contact device with the thermistor is positioned so that it lodges against the palpebral conjunctiva to measure the temperature at the palpebral conjunctiva. Monitoring the conjunctiva offers the advantages of an accessible tissue free of keratin, a capillary level close to the surface, and a tissue layer vascularized by the same arterial circulation as the brain. When the lids are closed, the thermal environment of the cornea is exclusively internal with passive prevention of heat loss during a blink and a more active heat transfer during the actual blink.

In carotid artery disease due to impaired blood supply to the eye, the eye has a lower temperature than that of the fellow eye which indicates a decreased blood supply. If a temperature difference greater than normal exists between the right and left eye, then there is an asymmetry in blood supply. Thus, this embodiment can provide information related to carotid and central nervous system vascular disorders. Furthermore, this embodiment can provide information concerning intraocular tumors such as melanoma. The area over a malignant melanoma has an increase in temperature and the eye harboring the malignant melanoma would have a higher temperature than that of the fellow eye. In this embodiment the thermistor is combined with a radio transmitter emitting an audio signal frequency proportional to the temperature.

Radiation sensitive endoradiosondes are known and can be used in the contact device to measure the amount of radiation and the presence of radioactive corpuscules in the tear film or in front of the eye which correlates to its presence in the body. The amount of hydration and humidity of the eye can be sensed with an electrical discharge and variable resistance moisture sensor mounted in the contact device. Motion and deceleration can be detected by a mounted accelerometer in the contact device. Voltages accompanying the function of the eye, brain, and muscles can be detected by suitable electrodes mounted in the device and can be used to modulate the frequency of the transmitter. In the case of transmission of muscle potentials, the contact device is placed not on the cornea, but next to the extraocular muscle to be evaluated and the signals remotely transmitted. A fixed frequency transmitter can be mounted in the contact device and used as a tracking device which utilizes a satellite tracking system by noting the frequency received from the fixed frequency transmitter to a passing satellite A surface electrode mounted in the contact device may be activated by optical or electromagnetic means in order to increase the temperature of the eye. This increase in temperature causes a dilation of the capillary bed and can be used in situations in which there is hypoxia (decreased oxygenation) in the eye. The concept and apparatus called heat stimulation transmission device (HSTD) is based upon my experiments and in the fact that the eye has one of largest blood supply per gram of tissue in the body and has the unique ability to be overpefused when there is an increase in temperature. The blood flow to the eye can thus be increased with a consequent increase in the amount of oxygen. The electrode can be placed in any part of the eye, inside or outside, but is preferably placed on the most posterior part of the eye. The radio frequency activated heating elements can be externally placed or surgically implanted according to the area in need of increase in the amount of oxygen in the eye. It is understood that the same heating elements could be placed or implanted in other parts of the body. Naturally, means that promote an increase in temperature of the eye without using electrodes can be used as long as the increase in temperature is sufficient to increase blood flow without promoting any injury.

The amount of increase varies from individual to individual and according to the status of the vascular bed of the eye. The increase in temperature of blood in the eye raises its oxygen level about 6% per each one degree Celsius of increase in temperature allowing precise quantification of the increase in oxygen by using a thermistor which simultaneously indicates temperature, or alternatively an oxygen sensor can be used in association with the heating element and actual amount of increase in oxygen detected.

This increase in blood flow can be timed to occur at predetermined hours in the case of chronic hypoxia such as in diabetes, retinal degenerations, and even glaucoma. These devices can be externally placed or surgically implanted in the eye or other parts of the body according to the application needed.

Another embodiment is called over heating transmission device (OHTD) and relates to a new method and apparatus for the treatment of tumors in the eye or any other part of the body by using surgically implanted or externally placed surface electrodes next to a tumor with the electrodes being activated by optical or electromagnetic means in order to increase the temperature of the cancerous tissue until excessive localized heat destroys the tumor cells. These electrodes can be packaged with a thermistor and the increase in temperature sensed by the thermistor with the signal transmitted to a remote station in order to evaluate the degree of temperature increase. The OHTD includes means to detect normal from abnormal tissue by labeling with the increase in temperature extending only to the abnormal tissue. Furthermore, sensors sensitive to necrotic products can be used to quantify the amount of tissue degradation.

Another embodiment concerning therapy of eye and systemic disorders include a neuro-stimulation transmission device (NSTD) which relates to a system in which radio activated micro-photodiodes or/and micro-electric circuits and electrodes are surgically implanted or externally placed on the eye or other parts of the body such as the brain and used to electrically stimulate non-functioning neural or degenerated neural tissue in order to treat patients with retinal degeneration, glaucoma, stroke, and the like. Multiple electrodes can be used in the contact device, placed on the eye or in the brain for electrical stimulation of surrounding tissues with consequent regeneration of signal transmission by axonal and neural cells and regeneration of action potential with voltage signals being transmitted to a remote station.

Radio and sonic transensors to measure pressure, electrical changes, dimensions, acceleration, flow, temperature, bioelectric activity and other important physiologic parameters and power switches to externally control the system have been developed and are suitable systems to be used in the apparatus of the invention. The sensors can be automatically turned on and off with power switches externally controlling the intelligent contact lens system. The use of integrated circuits and advances occurring in transducer, power source, and signal processing technology allow for extreme miniaturization of the components which permits several sensors to be mounted in one contact device. For instance, typical resolutions of integrated circuits are in the order of a few microns and very high density circuit realization can be achieved. Radio frequency and ultrasonic microcircuits are available and can be used and mounted in the contact device. A number of different ultrasonic and pressure transducers are also available and can be used and mounted in the contact device.

Technologic advances will occur which allow full and novel applications of the apparatus of the invention such as measuring enzymatic reactions and DNA changes that occur in the tear fluid or surface of the eye, thus allowing an early diagnosis of disorders such as cancer and heart diseases. HIV virus is present in tears and AIDS could be detected with the contact device by sensors coated with antibodies against the virus which would create a photochemical reaction with appearance of colorimetric reaction and potential shift in the contact device with subsequent change in voltage or temperature that can be transmitted to a monitoring station.

A variety of other pathogens could be identified in a similar fashion. These signals can be radio transmitted to a remote station for further signal processing and analysis. In the case of the appearance of fluorescent light, the outcome could be observed on a patient's eye simply by illuminating the eye with light going through a cobalt filter and in this embodiment the intelligent contact lens does not need to necessarily have signals transmitted to a station.

The system further comprises a contact device in which a microminiature gas-sensitive, such as oxygen-sensitive, radio frequency transensor is mounted in the contact device which in turn is placed on the cornea and/or surface of the eye. The system also comprises a contact device in which a microminiature blood velocity-sensitive radio frequency transensor is mounted in the contact device which in turn is placed on the conjunctiva and is preferably activated by eye lid motion and/or closure of the eye lid. The system also comprises a contact device in which a radio frequency transensor capable of measuring the negative resistance of nerve fibers is mounted in the contact device which in turn is preferably placed on the cornea and/or surface of the eye. By measuring the electrical resistance, the effects of microorganisms, drugs, poisons and anesthetics can be evaluated. The system also comprises a contact device in which a microminiature radiation-sensitive radio frequency transensor is mounted in the contact device which in turn is preferably placed on the cornea.

The contact device preferably includes a rigid or flexible annular member in which a transensor is mounted in the device. The transensor is positioned in a way to allow passage of light trough the visual axis. The annular member preferably includes an inner concave surface shaped to match an outer surface of the eye and having one or more holes defined therein in which transensors are mounted. It is understood that the contact device conforms in general shape to the surface of the eye with its dimensions and size chosen to achieve optimal comfort level and tolerance. It is also understood that the curvature and shape of the contact device is chosen to intimately and accurately fit the contact device to the surface of the eye for optimization of sensor function. The surface of the contact device can be porous or microporous as well as with mircro-protuberances on the surface. It is also understood that fenestrations can be made in the contact device in order to allow better oxygenation of the cornea when the device is worn for a long period of time. It is also understood that the shape of the contact device may include a ring-like or band-like shape without any material covering the cornea. It is also understood that the contact device may have a base down prism or truncated edge for better centration. It is also understood that the contact device preferably has a myofiange or a minus carrier when a conventional contact lens configuration is used. It is also understood that an eliptical half moon shape or the like can be used for placement under the eyelid. It is understood that the contact device can be made with soft of hard material according to the application needed. It is also understood that an oversized corneal scleral lens covering the whole anterior surface of the eye can be used as well as hourglass shaped lenses and the like. It is understood also that the external surface of the contact device can be made with polymers which increases adherence to tissues or coating which increases friction and adherence to tissues in order to optimize fluid passage to sensors when measuring chemical components. It is understood that the different embodiments which are used under the eyelids are shaped to fit beneath the upper and/or eyelids as well as to fit the upper or lower cul-de-sac.

The transensor may consist of a passive or active radio frequency emitter, or a miniature sonic resonator, and the like which can be coupled with miniature microprocessor mounted in the contact device. The transensors mounted in the contact device can be remotely driven by ultrasonic waves or alternatively remotely powered by electromagnetic waves or by incident light. They can also be powered by microminiature low voltage batteries which are inserted into the contact device.

As mentioned, preferably the data is transmitted utilizing radio waves, sound waves, light waves, by wire, or by telephone lines. The described techniques can be easily extrapolated to other transmission systems. The transmitter mounted in the contact device can use the transmission links to interconnect to remote monitoring sites. The changes in voltage or voltage level are proportional to the values of the biological variables and this amplified physiologic data signal from the transducers may be frequency modulated and then transmitted to a remote external reception unit which demodulates and reconstitutes the transmitted frequency modulated data signal preferably followed by a low pass filter with the regeneration of an analog data signal with subsequent tracing on a strip-chart recorder.

The apparatus of the invention can also utilize a retransmitter in order to minimize electronic components and size of the circuit housed in the contact device. The signal from a weak transmitter can be retransmitted to a greater distance by an external booster transmitter carried by the subject or placed nearby. It is understood that a variety of noise destruction methods can be used in the apparatus of the invention.

Since the apparatus of the invention utilizes externally placed elements on the surface of the eye that can be easily retrieved, there is no tissue damage due to long term implantation and if drift occurs it is possible to recalibrate the device. There are a variety of formats that can be used in the apparatus of the invention in which biologic data can be encoded and transmitted. The type of format for a given application is done according to power requirement, circuit complexity, dimensions and the type of biologic data to be transmitted. The general layout of the apparatus preferably includes an information source with a variety of biological variables, a transducer, a multiplexer, a transmitter, a transmission path and a transmission medium through which the data is transmitted preferably as a coded and modulated signal.

The apparatus of the invention preferably includes a receiver which receives the coded and modulated signal, an amplifier and low pass filter, a demultiplexer, a data processing device, a display and recording equipment, and preferably an information receiver, a CPU, a modem, and telephone connection. A microprocessor unit containing an autodialing telephone modem which automatically transmits the data over the public telephone network to a hospital based computer system can be used. It is understood that the system may accept digitally coded information or analog data.

When a radio link is used, the contact device houses a radio frequency transmitter which sends the biosignals to a receiver located nearby with the signals being processed and digitized for storage and analysis by microcomputer systems. When the apparatus of the invention transmits data using a radio link, a frequency carrier can be modulated by a subcarrier in a variety of ways: amplitude modulation (AM), frequency modulation (FM), and code modulation (CM). The subcarriers can be modulated in a variety of ways which includes AM, FM, pulse amplitude modulation (PAM), pulse duration modulation (PDM), pulse position modulation (PPM), pulse code modulation (PCM), delta modulation (DM), and the like.

It is understood that the ICL structure and the transducer/transmitter housing are made of material preferably transparent to radio waves and the electronic components coated with materials impermeable to fluids and salts and the whole unit encased in a biocompatable material. The electronics, sensors, and battery (whenever an active system is used), are housed in the contact device and are hermetically sealed against fluid penetration. It is understood that sensors and suitable electrodes such as for sensing chemicals, pH and the like, will be in direct contact with the tear fluid or the surface of the eye. It is also understood that said sensors, electrodes and the like may be covered with suitable permeable membranes according to the application needed. The circuitry and electronics may be encased in wax such as beeswax or paraffin which is not permeable to body fluid. It is understood that other materials can be used as a moisture barrier. It is also understood that various methods and materials can be used as long as there is minimal frequency attenuation, insulation, and biocompatibility. The components are further encased by biocompatible materials as the ones used in conventional contact lenses such as Hydrogel, silicone, flexible acrylic, sylastic, or the like.

The transmitter, sensors, and other components can be mounted and/or attached to the contact device using any known attachment techniques, such as gluing, heat-bonding, and the like. The intelligent contact lens can use a modular construction in its assembly as to allow tailoring the number of components by simply adding previously constructed systems to the contact device.

It is understood that the transmission of data can be accomplished using preferably radio link but other means can also be used. The choice of which energy form to be used by the ICL depends on the transmission medium and distance, channel requirement, size of transmitter equipment and the like. It is understood that the transmission of data from the contact device by wire can be used but has the disadvantage of incomplete freedom from attached wires. However, the connection of sensors by wires to externally placed electronics, amplifiers, and the like allows housing of larger sensors in the contact device when the application requires as well as the reduction of mechanical and electrical connections in the contact device. The transmission of data by wire can be an important alternative when there is congested space due to sensors and electronics in the contact device. It is understood that the transmission of data in water from the contact device can be preferably accomplished using sound energy with a receiver preferably using a hydrophone crystal followed by conventional audio frequency FM decoding.

It is also understood that the transmission of data from the contact device can be accomplished by light energy as an alternative to radio frequency radiation. Optical transmission of signals using all sorts of light such as visible, infrared, and ultraviolet can be used as a carrier for the transmission of data preferably using infrared light as the carrier for the transmission system. An LED can be mounted in the contact device and transmit modulated signals to remotely placed receivers with the light emitted from the LED being modulated by the signal. When using this embodiment, the contact device in the receiver unit has the following components: a built in infrared light emitter (950 mn), an infrared detector, decoder, display, and CPU. Prior to transmission, the physiologic variables found on the eye or tear fluid are multiplexed and encoded by pulse interval modulation, pulse frequency modulation, or the like. The infrared transmitter then emits short duration pulses which are sensed by a remotely placed photodiode in the infrared detector which is subsequently decoded, processed, and recorded. The light transmitted from the LED is received at the optical receiver and transformed into electrical signals with subsequent regeneration of the biosignals. Infrared light is reflected quite well including surfaces that do not reflect visible light and can be used in the transmission of physiological variables and position/motion measurement. This embodiment is particularly useful when there is limitations in bandwidth as in radio transmission. Furthermore, this embodiment may be quite useful with closed eyes since the light can be transmitted through the skin of the eyelid.

It is also understood that the transmission of data from the contact device can be accomplished by the use of sound and ultrasound being the preferred way of transmission underwater since sound is less strongly attenuated by water than radio waves. The information is transmitted using modulated sound signals with the sound waves being transmitted to a remote receiver. There is a relatively high absorption of ultrasonic energy by living tissues, but since the eye even when closed has a rather thin intervening tissue the frequency of the ultrasonic energy is not restricted. However, soundwaves are not the preferred embodiment since they can take different paths from their source to a receiver with multiple reflections that can alter the final signal. Furthermore, it is difficult to transmit rapidly changing biological variables because of the relatively low velocity of sound as compared to electromagnetic radiation. It is possible though to easily mount an ultrasonic endoradiosonde in the contact device such as for transmitting pH values or temperature. An ultrasonic booster transmitter located nearby or carried by the subject can be used to transmit the signal at a higher power level. An acoustic tag with a magnetic compass sensor can be used with the information acoustically telemetered to a sector scanning sonar.

A preferred embodiment of the invention consists of electrodes, FM transmitter, and a power supply mounted in the contact device. Stainless steel micro cables are used to connect the electronics to the transducers to the battery power supply. A variety of amplifiers and FM transmitters including Colpitts oscillator, crystal oscillators and other oscillators preferably utilizing a custom integrated circuit approach with ultra density circuitry can be used in the apparatus of the invention.

Several variables can be simultaneously transmitted using different frequencies using several transmitters housed in the contact device. Alternatively, a single transmitter (3 channel transmitter) can transmit combined voltages to a receiver, with the signal being subsequently decoded, separated into three parts, filtered and regenerated as the three original voltages (different variables such as glucose level, pressure and temperature). A multiple channel system incorporating all signal processing on a single integrated circuit minimizes interconnections and can be preferably mounted in the apparatus of the invention when multiple simultaneous signal transmission is needed such as transmitting the level of glucose, temperature, bioelectrical, and pressure. A single-chip processor can be combined with a logic chip to also form a multichannel system for the apparatus of the invention allowing measurement of several parameters as well as activation of transducers.

It is understood that a variety of passive, active, and inductive power sources can be used in the apparatus of the invention. The power supply may consist of micro batteries, inductive power link, energy from biological sources, nuclear cells, micro power units, fuel cells which use glucose and oxygen as energy sources, and the like. The type of power source is chosen according to the biological or biophysical event to be transmitted.

A variety of signal receivers can be used such a frame aerial connected to a conventional FM receiver from which the signal is amplified decoded and processed. Custom integrated circuits will provide the signal processing needed to evaluate the parameters transmitted such as temperature, pressure flow dimensions, bioelectrical activity, concentration of chemical species and the like. The micro transducers, signal processing electronics, transmitters and power source can be built in the contact device.

Power for the system may be supplied from a power cell activated by a micropower control switch contained in the contact device or can be remotely activated by radio frequency means, magnetic means and the like. Inductive radio frequency powered telemetry in which the same coil system used to transfer energy is used for the transmission of data signal can be used in the apparatus of the invention. The size of the system relates primarily to the size of the batteries and the transmitter. The size of conventional telemetry systems are proportional to the size of the batteries because most of the volume is occupied by batteries. The size of the transmitter is related to the operating frequency with low frequencies requiring larger components than higher frequency circuits. Radiation at high frequencies are more attenuated than lower frequencies by body tissues. Thus a variety of systems implanted inside the body requires lower frequency devices and consequently larger size components in order for the signal to be less atenuated. Since the apparatus of the invention is placed on the surface of the eye there is little to no attenuation of signals and thus higher frequency small devices can be used. Furthermore, very small batteries can be used since the contact device can be easily retrieved and easily replaced. The large volume occupied by batteries and power sources in conventional radio telemetry implantable devices can be extremely reduced since the apparatus of the invention is placed externally on the eye and is of easy access and retrieval, and thus a very small battery can be utilized and replaced whenever needed.

A variety of system assemblies can be used but the densest system assembly is preferred such as a hybrid assembly of custom integrated circuits which permits realization of the signal processing needed for the applications. The typical resolution of such circuits are in the order of a few microns and can be easily mounted in the contact device. A variety of parameters can be measured with one integrated circuit which translates the signals preferably into a transmission bandwidth. Furthermore, a variety of additional electronics and a complementary metal oxide semiconductor (CMOS) chip can be mounted in the apparatus of the invention for further signal processing and transmission.

The micropower integrated circuits can be utilized with a variety of transmitter modalities mounted in the intelligent contact lens including radio links, ultrasonic link and the like. A variety of other integrated circuits can be mounted in the contact device such as signal processors for pressure and temperature, power switches for external control of implanted electronics and the like. Pressure transducers such as a capacitive pressure transducer with integral electronics for signal processing can be incorporated in the same silicon structure and can be mounted in the contact device. Evolving semiconductor technology and more sophisticated encoding methods as well as microminiature integrated circuits amplifiers and receivers are expected to occur and can be housed in the contact device. It is understood that a variety of transmitters, receivers, and antennas for transmitting and receiving signals in telemetry can be used in the apparatus of the invention, and housed in the contact device and/or placed remotely for receiving, processing, and analyzing the signal.

The fluid present on the front surface of the eye covering the conjunctiva and cornea is referred as the tear film or tear fluid. Close to 100% of the tear film is produced by the lacrimal gland and secreted at a rate of $2\,\mu l$/min. The volume of the tear fluid is approximately $10\,\mu l$. The layer of tear fluid covering the cornea is about 8–10 $\mu m$ in thickness and the tear fluid covering the conjunctiva is about 1 5 $\mu m$ thick. The pre-corneal tear film consists of three layers: a thin lipid layer measuring about 0.1 $\mu m$ consisting of the air tear interface, a mucin layer measuring $0.03\mu m$ which is in direct contact with the corneal epithelium, and finally the remaining layer is the thick aqueous layer which is located between the lipid and mucin layer. The aqueous layer is primarily derived from the secretions of the lacrimal gland and its chemical composition is very similar to diluted blood with a reduced protein content and slightly greater osmotic pressure. The secretion and flow of tear fluid from the lacrimal gland located in the supero-temporal quadrant with the subsequent exit through the lacrimal puncta located in the infero-medial quadrant creates a continuous flow of tear fluid providing the ideal situation by furnishing a continuous supply of substrate for one of the stoichiometric reactions which is the subject of a preferred embodiment for evaluation of glucose levels. The main component of the tear fluid is the aqueous layer which is an ultrafiltrate of blood containing electrolytes such as sodium, potassium, chloride, bicarbonate, calcium, and magnesium as well as amino acids, proteins, enzymes, DNA, lipids, cholesterol, glycoproteins, immunoglobulins, vitamins, minerals and hormones. Moreover, the aqueous layer also holds critical metabolites such as glucose, urea, catecholainines, and lactate, as well as gases such as oxygen and carbon dioxide. Furthermore, any exogenous substances found in the blood stream such as drugs, radioactive compounds and the like are present in the tear fluid. Any compound present in the blood can potentially noninvasively be evaluated with the apparatus of the invention with the data transmitted and processed at a remotely located station.

According to one preferred embodiment of the invention, the non-invasive analysis of glucose levels will be described: Glucose Detection:—The apparatus and methods for measurement of blood components and chemical species in the tear fluid and/or surface of the eye is based on electrodes associated with enzymatic reactions providing an electrical current which can be radio transmitted to a remote receiver providing continuous data on the concentration of species in the tear fluid or surface of the eye. The ICL system is preferably based on a diffusion limited sensors method that requires no reagents or mechanical/moving parts in the contact device. The preferred method and apparatus of the glucose detector using ICL uses the enzyme glucose oxidase which catalyze a reaction involving glucose and oxygen in association with electrochemical sensors mounted in the contact device that are sensitive to either the product of the reaction, an endogenous coreactant, or a coupled electron carrier molecule such as the ferrocene-mediated glucose sensors, as well as the direct electrochemical reaction of glucose at the contact device membrane-covered catalytic metal electrode.

Glucose and oxygen present in the tear fluid either derived from the lacrimal gland or diffused from vessels on the surface of the eye will diffuse into the contact device reaching an immobilized layer of enzyme glucose oxidase mounted in the contact device. Successful operation of enzyme electrodes demand constant transport of the substrate to the electrode since the substrate such as glucose and oxygen are consumed enzymatically. The ICL is the ideal device for using enzyme electrodes since the tear fluid flows continuously on the surface of the eye creating an optimal environment for providing substrate for the stoichiometric reaction. The ICL besides being a noninvasive system solves the critical problem of sensor lifetime which occurs with any sensors that are implanted inside the body. The preferred embodiment refers to amperometric glucose biosensors with the biosensors based on biocatalytic oxidation of glucose in the presence of the enzyme oxidase. This is a two step process consisting of enzymatic oxidation of glucose by glucose oxidase in which the co-factor flavin-adenine dinucleotide (FAD) is reduced to $FADH_2$ followed by oxidation of the enzyme co-factor by molecular oxygen with formation of hydrogen peroxide.

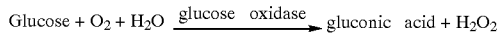

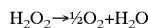

With catalase enzyme the overall reaction is

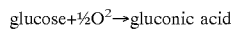

Glucose concentration can be measured either by electrochemical detection of an increase of the anodic current due to hydrogen peroxide (product of the reaction) oxidation or by detection of the decrease in the cathodic current due to oxygen (co-reactant) reduction. The ICL glucose detection system preferably has an enzyme electrode in contact with the tear fluid and/or surface of the eye capable of measuring the oxidation current of hydrogen peroxide created by the stoichiometric conversion of glucose and oxygen in a layer of glucose oxidase mounted inside the contact device. The ICL glucose sensor is preferably electrochemical in nature and based on a hydrogen peroxide electrode which is converted by immobilized glucose oxidase which generates a direct current depending on the glucose concentration of the tear fluid.

The glucose enzyme electrode of the contact device responds to changes in the concentration of both glucose and oxygen, both of which are substrates of the immobilized enzyme glucose oxidase. It is also understood that the sensor in the contact device can be made responsive to glucose only by operating in a differential mode. The enzymatic electrodes built in the contact device are placed in contact with the tear fluid or the surface of the eye and the current generated by the electrodes according to the stoichiometric conversion of glucose, are subsequently converted to a frequency audio signal and transmitted to a remote receiver, with the current being proportional to the glucose concentration according to calibration factors.

The signals can be transmitted using the various transmission systems previously described with an externally placed receiver demodulating the audio frequency signal to a voltage and the glucose concentration being calculated from the voltage and subsequently displayed on a LED display. An interface card can be used to connect the receiver with a computer for further signal processing and analysis.

During oxidation of glucose by glucose oxidase an electrochemically oxidable molecule or any other oxidable species generated such as hydrogen peroxide can be detected amperometrically as a current by the electrodes. A preferred embodiment includes a tree electrode setup consisting of a working electrode (anode) and auxiliary electrode (cathode) and a reference electrode connected to an amperometric detector. It should be noted though, that a glucose sensor could function well using two electrodes. When appropriate voltage difference is applied between the working and auxiliary electrode, hydrogen peroxide is oxidized on the surface of the working electrode which creates a measurable electric current. The intensity of the current generated by the sensor is proportional to the concentration of hydrogen peroxide which is proportional to the concentration of glucose in the tear film and the surface of the eye.

A variety of materials can be used for the electrodes such as silver/silver chloride coded cathodes. Anodes may be preferably constructed as a platinum wire coated with glucose oxidase or preferably covered by a immobilized glucose oxidase membrane. Several possible configurations for sensors using amperometric enzyme electrodes which involves detection of oxidable species can be used in the apparatus of the invention. A variety of electrodes and setups can be used in the contact device which are capable of creating a stable working potential and output current which is proportional to the concentration of blood components in the tear fluid and surface of the eye. It is understood that a variety of electrode setups for the amperometric detection of oxidable species can be accomplished with the apparatus of the invention. It is understood that solutions can be applied to the surface of the electrodes to enhance transmission.

Other methods which use organic mediators such as ferrocene which transfers electrons from glucose oxidase to a base electrode with subsequent generation of current can be utilized. It is also understood that needle-type glucose sensors can be placed in direct contact with the conjunctiva or encased in a contact device for measurement of glucose in the tear fluid. It is understood that any sensor capable of converting a biological variable to a voltage signal can be used in the contact device and placed on the surface of the eye for measurement of the biological variables. It is understood that any electrode configuration which measures hydrogen peroxide produced in the reaction catalysed by glucose oxidase can be used in the contact device for measurement of glucose levels. It is understood that the following oxygen based enzyme electrode glucose sensor can be used in the apparatus of the invention which is based on the principal that the oxygen not consumed by the enzymatic reactions by catalase enzyme is electrochemically reduced at an oxygen sensor producing a glucose modulated oxygen dependent current. This current is compared to a current from a similar oxygen sensor without enzymes.

It is understood that the sensors are positioned in a way to optimize the glucose access to the electrodes such as by creating micro traumas to increase diffusion of glucose across tissues and capillary walls, preferably positioning the sensors against vascularized areas of the eye. In the closed eye about two-thirds of oxygen and glucose comes by diffusion from the capillaries. Thus positioning the sensors against the palpebral conjunctiva during blinking can increase the delivery of substrates to the contact device biosensor allowing a useful amount of substrates to diffuse through the contact device biosensor membranes.

There are several locations on the surface of the eye in which the ICL can be used to measure glucose such as: the tear film laying on the surface of the cornea which is an ultrafiltrate of blood derived from the main lacrimal gland; the tear meniscus which is a reservoir of tears on the edge of the eye lid; the supero-temporal conjunctival fornix which allows direct measurement of tears at the origin of secretion; the limbal area which is a highly vascularized area between cornea and the sclera; and preferably the highly vascularized conjunctiva. The contact device allows the most efficient way of acquiring fluid by creating micro-damage to the epithelium with a consequent loss of the blood barrier function of said epithelium, with the subsequent increase in tissue fluid diffusion. Furthermore, mechanical irritation caused by an intentionally constructed slightly rugged surface of the contact device in order to increase the flow of substrates. Furthermore, it is understood that a heating element can be mounted in association with the sensor in order to increase transudation of fluid.

The samples utilized for noninvasive blood analysis may preferably be acquired by micro-traumas to the conjunctiva caused by the contact device which has micro projections on its surface in contact with the conjunctiva creating an increase in the diffusion rate of plasma components through the capillary walls toward the measuring sensors. Moreover, the apparatus of the invention may promote increased vascular permeability of conjunctival vessels through an increase in temperature using surface electrodes as heating elements. Furthermore, the sensors may be located next to the exit point of the lacrimal gland duct in order to collect tear fluid close to its origin. Furthermore, the sensors may be placed inferiorly in contact with the conjunctival tear meniscus which has the largest volume of tear fluid on the surface of the eye. Alternatively, the sensors may be placed in contact with the limbal area which is a substantially vascularized surface of the eye. Any means that create a micro-disruption of the integrity of the ocular surface or any other means that cause transudation of tissue fluid and consequently plasma may be used in the invention. Alternatively, the sensors may be placed against the vascularized conjunctiva in the cul-de-sac superiorly or inferiorly.

It is also understood that the sensors can be placed on any location on the surface of the eye to measure glucose and other chemical compounds. Besides the conventional circular shape of contact lenses, the shape of the contact device also includes a flat rectangular configuration, ring like or half moon like which are used for applications that require placement under the palpebral conjunctiva or cul-de-sac of the eye.

A recessed region is created in the contact device for placement of the electrodes and electronics with enzyme active membranes placed over the electrodes. A variety of membranes with different permeabilities to different chemical species are fitted over the electrodes and enzyme-active membranes. The different permeability of the membranes allows selection of different chemicals to be evaluated and to prevent contaminants from reaching the electrodes. Thus allowing several electroactive compounds to be simultaneously evaluated by mounting membranes with different permeabilities with suitable electrodes on the contact device.

It is also understood that multilayer membranes with preferential permeability to different compounds can be used. The contact device encases the microelectrodes forming a bioprotective membrane such that the electrodes are covered by the enzyme active membrane which is covered by the contact device membrane such as polyurethane which is biocompatable and permeable to the analytes A membrane between the electrodes and the enzyme membrane can be used to block interfering substances without altering transport of peroxide ion. The permeability of the membranes are used to optimize the concentration of the compounds needed for the enzymatic reaction and to protect against interfering elements.

It is understood that the diffusion of substrate to the sensor mounted in the contact device is preferably perpendicular to the plane of the electrode surface. Alternatively, it is understood that the membrane and surface of the contact device can be constructed to allow selective non-perpendicular diffusion of the substrates. It is also understood that membranes such as negatively charged perfluorinated ionomer Nafion membrane can be used in order to reduce interference by electroactive compounds such as ascorbate, urate and acetaminophen. It is also understood that new polymers and coatings under development which are capable of preferential selection of electroactive compounds and that can prevent degradation of electrodes and enzymes can be used in the apparatus of the invention.

The sensors and membranes coupled with radio transmitters can be positioned in any place in the contact device but may be placed in the cardinal positions in a pie like configuration, with each sensor transmitting its signal to a receiver. For example, if four biological variables are being detected simultaneously the four sensors signals A, B, C, and D are simultaneously transmitted to one or more receivers. Any device utilizing the tear fluid to non-invasively measure the blood components and signals transmitted to a remote station can be used in the apparatus of the invention. Preferably a small contact device, however any size or shape of contact devices can be used to acquire the data on the surface of the eye.

An infusion pump can be activated according to the level of glucose detected by the ICL system and insulin injected automatically as needed to normalize glucose levels as an artificial pancreas. An alarm circuit can also be coupled with the pump and activated when low or high levels of glucose are present thus alerting the patient. It is understood that other drugs, hormones, and chemicals can be detected and signals transmitted in the same fashion using the apparatus of the invention.

A passive transmitter carrying a resonance circuit can be mounted in the contact device with its frequency altered by a change in reactance whose magnitude changes in response to the voltage generated by the glucose sensors. As the signal from passive transmitters falls off extremely rapidly with distance, the antenna and receiver should be placed near to the contact device such as in the frame of regular glasses.

It is also understood that active transmitters with batteries housed in the contact device and suitable sensors as previously described can also be used to detect glucose levels. It is also understood that a vibrating micro-quartz crystal connected to a coil and capable of sending both sound and radio impulses can be mounted in the contact device and continuously transmit data signals related to the concentration of chemical compounds in the tear fluid.

An oxygen electrode consisting of a platinum cathode and a silver anode loaded with polarographic voltage can be used in association with the glucose sensor with the radio transmission of the two variables. It is also understood that sensors which measure oxygen consumption as indirect means of evaluating glucose levels can be used in the apparatus of the invention. The membranes can be used to increase the amount of oxygen delivered to the membrane enzyme since all glucose oxidase systems require oxygen and can potentially become oxygen limited. The membranes also can be made impermeable to other electroactive species such as acetamymophen or substances that can alter the level of hydrogen peroxide produced by the glucose oxidase enzyme membrane.

It is understood that a polarographic Clark-type oxygen detector electrode consisting of a platinum cathode in a silver-to-silver-chloride anode with signals telemetered to a remote station can be used in the apparatus of the invention. It is also understood that other gas sensors using galvanic configuration and the like can be used with the apparatus of the invention. The oxygen sensor is preferably positioned so as to lodge against the palpebral conjunctiva. The oxygen diffusing across the electrode membrane is reduced at the cathode which produces a electrical current which is converted to an audio frequency signal and transmitted to a remote station. The placement of the sensor in the conjunctiva allows intimate contact with an area vascularized by the same arterial circulation as the brain which correlates with arterial oxygen and provides an indication of peripheral tissue oxygen. This embodiment allows good correlation between arterial oxygen and cerebral blood flow by monitoring a tissue bed vascularized by the internal carotid artery, and thus, reflects intracranial oxygenation.

This embodiment can be useful during surgical procedures such as in carotid endarterectomy allowing precise detection of the side with decreased oxygenation. This same embodiment can be useful in a variety of heart and brain operations as well as in retinopathy of prematurity which allows close observation of the level of oxygen administered and thus prevention of hyperoxia with its potentially blinding effects while still delivering adequate amount of oxygen to the infant.

Cholesterol secreted in the tear fluid correlates with plasma cholesterol and a further embodiment utilizes a similar system as described by measurement of glucose. However, this ICL as designed by the inventor involves an immobilized cholesterol esterase membrane which splits cholesterol esters into free cholesterol and fatty acids. The free cholesterol passes through selectively permeable membrane to both free cholesterol and oxygen and reaches a second membrane consisting of an immobilized cholesterol oxidase. In the presence of oxygen the free cholesterol is transformed by the cholesterol oxidase into cholestenone and hydrogen peroxide with the hydrogen peroxide being oxidized on the surface of the working electrode which creates a measurable electric current with signals preferably converted into audio frequency signals and transmitted to a remote receiver with the current being proportional to the cholesterol concentration according to calibration factors. The method and apparatus described above relates to the following reaction or part of the following reaction. Cholesterol ester cholesterol esterase→Free cholesterol+fatty acids Free cholesterol+$O_2$ cholesterol oxidase→Cholestenone+$H_2O_2$ A further embodiment utilizes an antimone electrode that can be housed in the contact device and used to detect the pH and other chemical species of the tear fluid and the surface of the eye. It is also understood that a glass electrode with a transistor circuit capable of measuring pH, pH endoradiosondes, and the like can be used and mounted in the contact device and used for measurement of the pH in the tear fluid or surface of the eye with signals preferably radio transmitted to a remote station.

In another embodiment, catalytic antibodies immobilized in a membrane with associated pH sensitive electrodes can identify a variety of antigens. The antigen when interacting with the catalytic antibody can promote the formation of acetic acid with a consequent change in pH and current that is proportional to the concentration of the antigens according to calibration factors.

In a further embodiment an immobilized electrocatalytic active enzyme and associated electrode promote, in the presence of a substrate (meaning any biological variable), an electrocatalytic reaction resulting in a current that is proportional to the amount of said substrate. It is understood that a variety of enzymatic and nonenzymatic detection systems can be used in the apparatus of the invention.

It is understood that any electrochemical sensor, thermoelectric sensors, acoustic sensors, piezoelectric sensors, optical sensors, and the like can be mounted in the contact device and placed on the surface of the eye for detection and measurement of blood components and physical parameters found in the eye with signals preferably transmitted to a remote station. It is understood that electrochemical sensors using amperometric, potentiometric, conductometric, gravimetric, impedimetric, systems, and the like can be used in the apparatus of the invention for detection and measurement of blood components and physical parameters found in the eye with signals preferably transmitted to a remote station.

Some preferable ways have been described; however, any other miniature radio transmitters can be used and mounted in the contact device and any microminiature sensor that modulates a radio transmitter and send the signal to a nearby radio receiver can be used. Other microminiature devices capable of modulating an ultrasound device, or infrared and laser emitters, and the like can be mounted in the contact device and used for signal detection and transmission to a remote station. A variety of methods and techniques and devices for gaining and transmitting information from the eye to a remote receiver can be used in the apparatus of the invention.

It is an object of the present invention to provide an apparatus and method for the non-invasive measurement and evaluation of blood components.

It is also an object of the present invention to provide an intelligent contact lens system capable of receiving, processing, and transmitting signals such as electromagnetic waves, radio waves, infrared and the like being preferably transmitted to a remote station for signal processing and analysis, with transensors and biosensors mounted in the contact device.

It is a further object of the present invention to detect physical changes that occur in the eye, preferably using optical emitters and sensors.

It is a further object of the present invention to provide a novel drug delivery system and treatment of eye and systemic diseases.

The above and other objects and advantages will become more readily apparent when reference is made to the following description taken in conjunction with the accompanying drawings.

BRIEF DESCRIPTION OF THE DRAWINGS

FIGS. 2A–2D schematically illustrate a preferred embodiment of a contact device according the present invention.

FIGS. 7A and 7B are block diagrams illustrating an arrangement capable compensating for deviations in corneal thickness according to the present invention.

FIGS. 36A through 36J schematically illustrate various shapes of a contact device incorporating the principles of the present invention.

FIG. 39A illustrates the continuous flow of fluid in the eye. FIG. 39B schematically illustrates an alternative embodiment of the contact device of the present invention used under the eyelid to produce signals based upon flow of tear fluid through the eye and transmit the signals by a wire connected to an external device.

FIG. 42A illustrates open eye lids positioned over a contact device including a somnolence awareness device, whereas FIG. 42B illustrates the closing of the eyelids and the production of a signal externally transmitted to an alarm device.

FIG. 43 is a detailed view of a portion of an eyeball including a heat stimulation transmission device.

FIG. 44 is a front view of a heat stimulation transmission device mounted on a contact device and activated by a remote hardware device.

FIG. 45 illustrates a band heat stimulation transmission device for external use or surgical implantation in any part of the body.

FIG. 46 illustrates a surgically implantable heat stimulation transmission device for implantation in the eye between eye muscles.

FIG. 47 illustrates a heat stimulation device for surgical implantation in any part of the body.

DESCRIPTION OF THE PREFERRED EMBODIMENTS

APPLANATION

Figure 1:
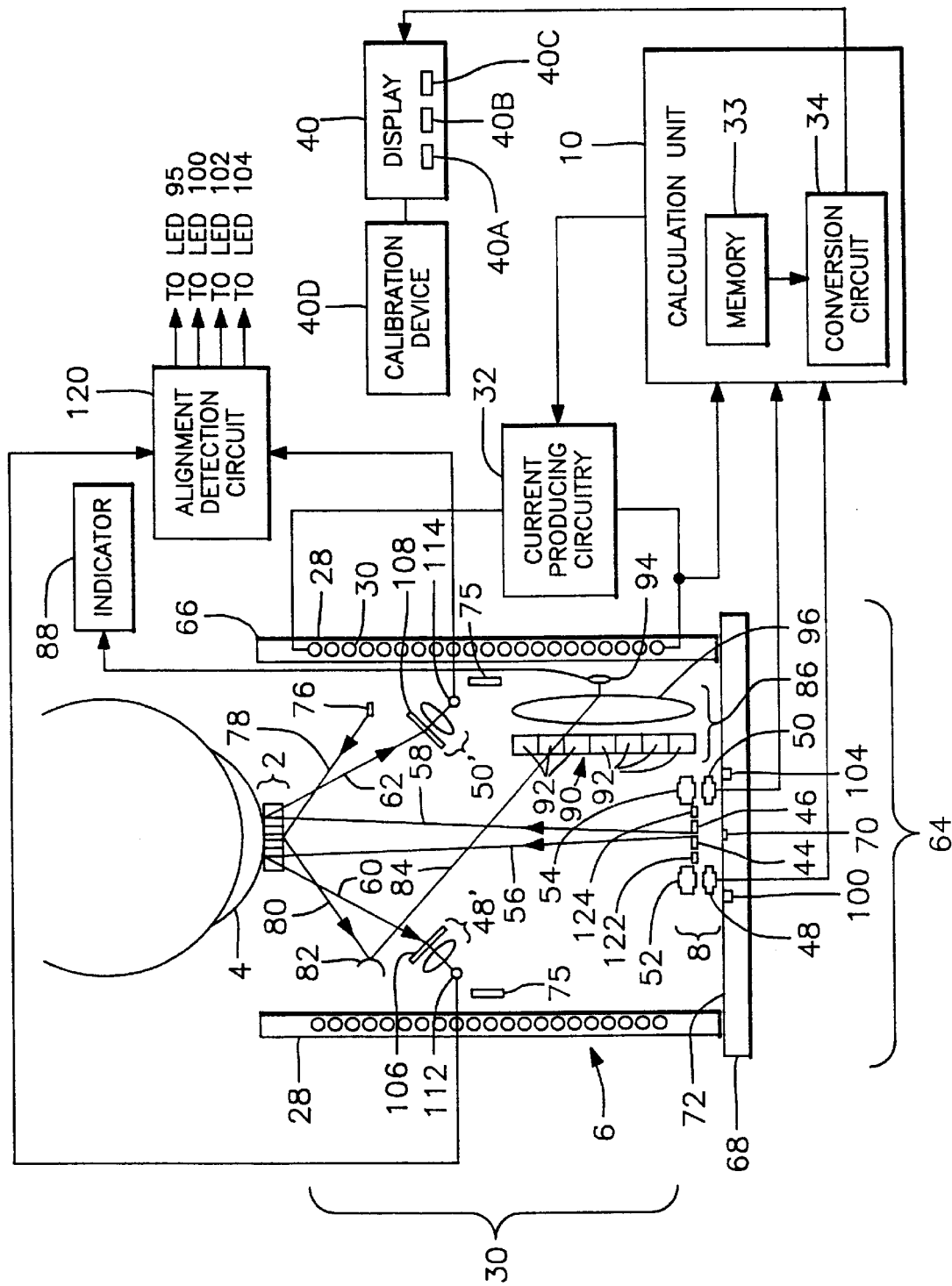
FIG. 1 is a schematic block diagram illustrating a system for measuring intraocular pressure in accordance with a preferred embodiment of the present invention.

A preferred embodiment of the present invention will now be described with reference to the drawings. According to the preferred embodiment illustrated in FIG. 1, a system is provided for measuring intraocular pressure by applanation. The system includes a contact device 2 for placement in contact with the cornea 4, and an actuation apparatus 6 for actuating the contact device 2 so that a portion thereof projects inwardly against the cornea 4 to provide a predetermined amount of applanation. The system further includes a detecting arrangement 8 for detecting when the predetermined amount of applanation of the cornea 4 has been achieved and a calculation unit 10 responsive to the detecting arrangement 8 for determining intraocular pressure based on the amount of force the contact device 2 must apply against the cornea 4 in order to achieve the predetermined amount of applanation.

The contact device 2 illustrated in FIG. 1 has an exaggerated thickness to more clearly distinguish it from the cornea 4. FIGS. 2A–2D more accurately illustrate a preferred embodiment of the contact device 2 which includes a substantially rigid annular member 12, a flexible membrane 14 and a movable central piece 16. The substantially rigid annular member 12 includes an inner concave surface 18 shaped to match an outer surface of the cornea 4 and having a hole 20 defined therein. The substantially rigid annular member 12 has a maximum thickness (preferably approximately 1 millimeter) at the hole 20 and a progressively decreasing thickness toward a periphery 21 of the substantially rigid annular member 12. The diameter of the rigid annular member is approximately 11 millimeters and the diameter of the hole 20 is approximately 5.1 millimeters according to a preferred embodiment. Preferably, the substantially rigid annular member 12 is made of transparent polymethylmethacrylate; however, it is understood that many other materials, such as glass and appropriately rigid plastics and polymers, may be used to make the annular member 12. Preferably, the materials are chosen so as not to interfere with light directed at the cornea or reflected back therefrom.

The flexible membrane 14 is preferably secured to the inner concave surface 18 of the substantially rigid annular member 12 to provide comfort for the wearer by preventing scratches or abrasions to the corneal epithelial layer. The flexible membrane 14 is coextensive with at least the hole 20 in the annular member 12 and includes at least one transparent area 22. Preferably, the transparent area 22 spans the entire flexible membrane 14, and the flexible membrane 14 is coextensive with the entire inner concave surface 18 of the rigid annular member 12. According to a preferred arrangement, only the periphery of the flexible membrane 14 and the periphery of the rigid annular member 12 are secured to one another. This tends to minimize any resistance the flexible membrane might exert against displacement of the movable central piece 16 toward the cornea 4.

According to an alternative arrangement, the flexible membrane 14 is coextensive with the rigid annular member and is heat-sealed thereto over its entire extent except for a circular region within approximately one millimeter of the hole 20.

Although the flexible membrane 14 preferably consists of a soft and thin polymer, such as transparent silicone elastic, transparent silicon rubber (used in conventional contact lens), transparent flexible acrylic (used in conventional intraocular lenses), transparent hydrogel, or the like, it is well understood that other materials may be used in manufacturing the flexible membrane 14.

The movable central piece 16 is slidably disposed within the hole 20 and includes a substantially flat inner side 24 secured to the flexible membrane 14. The engagement of the inner side 24 to the flexible membrane 14 is preferably provided by glue or thermo-contact techniques. It is understood, however, that various other techniques may be used in order to securely engage the inner side 24 to the flexible membrane 14. Preferably, the movable central piece 16 has a diameter of approximately 5.0 millimeters and a thickness of approximately 1 millimeter.

A substantially cylindrical wall 42 is defined circumferentially around the hole 20 by virtue of the increased thickness of the rigid annular member 12 at the periphery of the hole 20. The movable central piece 16 is slidably disposed against this wall 42 in a piston-like manner and preferably has a thickness which matches the height of the cylindrical wall 42. In use, the substantially flat inner side 24 flattens a portion of the cornea 4 upon actuation of the movable central piece 16 by the actuation apparatus 6.

The overall dimensions of the substantially rigid annular member 12, the flexible membrane 14 and the movable central piece 16 are determined by balancing several factors, including the desired range of forces applied to the cornea 4 during applanation, the discomfort tolerances of the patients, the minimum desired area of applanation, and the requisite stability of the contact device 2 on the cornea 4. In addition, the dimensions of the movable central piece 16 are preferably selected so that relative rotation between the movable central piece 16 and the substantially rigid annular member 12 is precluded, without hampering the aforementioned piston-like sliding.

The materials used to manufacture the contact device 2 are preferably selected so as to minimize any interference with light incident upon the cornea 4 or reflected thereby.

Preferably, the actuation apparatus 6 illustrated in FIG. 1 actuates the movable central piece 16 to cause sliding of the movable central piece 16 in the piston-like manner toward the cornea 4. In doing so, the movable central piece 16 and a central portion of the flexible membrane 14 are caused to project inwardly against the cornea 4. This is shown in FIGS. 2C and 2D. A portion of the cornea 4 is thereby flattened. Actuation continues until a predetermined amount of applanation is achieved.

Preferably, the movable central piece 16 includes a magnetically responsive element 26 arranged so as to slide along with the movable central piece 16 in response to a magnetic field, and the actuation apparatus 6 includes a mechanism 28 for applying a magnetic field thereto. Although it is understood that the mechanism 28 for applying the magnetic field may include a selectively positioned bar magnet, according to a preferred embodiment, the mechanism 28 for applying the magnetic field includes a coil 30 of long wire wound in a closely packed helix and circuitry 32 for producing an electrical current through the coil 30 in a progressively increasing manner. By progressively increasing the current, the magnetic field is progressively increased. The magnetic repulsion between the actuation apparatus 6 and the movable central piece 16 therefore increases progressively, and this, in turn, causes a progressively greater force to be applied against the cornea 4 until the predetermined amount of applanation is achieved.

Using known principles of physics, it is understood that the electrical current passing through the coil 30 will be proportional to the amount of force applied by the movable central piece 16 against the cornea 4 via the flexible membrane 14. Since the amount of force required to achieve the predetermined amount of applanation is proportional to intraocular pressure, the amount of current required to achieve the predetermined amount of applanation will also be proportional to the intraocular pressure. Thus, a conversion factor for converting a value of current to a value of intraocular pressure can easily be determined experimentally upon dimensions of the system, the magnetic responsiveness of the magnetically responsive element 26, number of coil windings, and the like.

Besides using experimentation techniques, the conversion factor may also be determined using known techniques for calibrating a tonometer. Such known techniques are based on a known relationship which exists between the inward displacement of an indentation device and the volume changes and pressure in the indented eye. Examples of such techniques are set forth in Shiotz, Communications: Tonometry, The Brit. J. of Ophthalmology, June 1920, p. 249–266; Friedenwald, Tonometer Calibration, Trans. Amer. Acad. of O. & O., January-February 1957, pp. 108–126; and Moses, Theory and Calibration of the Schiotz Tonometer VII: Experimental Results of Tonometric Measurements: Scale Reading Versus Indentation Volume, Investigative Ophthalmology, September 1971, Vol. 10, No. 9, pp. 716–723.

In light of the relationship between current and intraocular pressure, the calculation unit 10 includes a memory 33 for storing a current value indicative of the amount of current passing through the coil 30 when the predetermined amount of applanation is achieved. The calculation unit 10 also includes a conversion unit 34 for converting the current value into an indication of intraocular pressure.

Preferably, the calculation unit 10 is responsive to the detecting arrangement 8 so that when the predetermined amount of applanation is achieved, the current value (corresponding to the amount of current flowing through the coil 30) is immediately stored in the memory 33. At the same time, the calculation unit 10 produces an output signal directing the current producing circuitry 32 to terminate the flow of current. This, in turn, terminates the force against the cornea 4. In an alternative embodiment, the current producing circuitry 32 could be made directly responsive to the detecting arrangement 8 (i.e., not through the calculation unit 10) so as to automatically terminate the flow of current through the coil 30 upon achieving the predetermined amount of applanation.

The current producing circuitry 32 may constitute any appropriately arranged circuit for achieving the progressively increasing current. However, a preferred current producing circuit 32 includes a switch and a DC power supply, the combination of which is capable of producing a step function. The preferred current producing circuitry 32 further comprises an integrating amplifier which integrates the step function to produce the progressively increasing current.

The magnetically responsive element 26 is circumferentially surrounded by a transparent peripheral portion 36. The transparent peripheral portion 36 is aligned with the transparent area 22 and permits light to pass through the contact device 2 to the cornea 4 and also permits light to reflect from the cornea 4 back out of the contact device 2 through the transparent on peripheral portion 36. Although the transparent peripheral portion 36 may consist entirely of an air gap, for reasons of accuracy and to provide smoother sliding of the movable central piece 16 through the rigid annular member 12, it is preferred that a transparent solid material constitute the transparent peripheral portion 36. Exemplary transparent solid materials include polymethyl methacrylate, glass, hard acrylic, plastic polymers, and the like.

The magnetically responsive element 26 preferably comprises an annular magnet having a central sight hole 38 through which a patient is able to see while the contact device 2 is located on the patient's cornea 4. The central sight hole 38 is aligned with the transparent area 22 of the flexible membrane 14 and is preferably at least 1–2 millimeters in diameter.

Although the preferred embodiment includes an annular magnet as the magnetically responsive element 26, it is understood that various other magnetically responsive elements 26 may be used, including various ferromagnetic materials and/or suspensions of magnetically responsive particles in liquid. The magnetically responsive element 26 may also consist of a plurality of small bar magnets arranged in a circle, to thereby define an opening equivalent to the illustrated central sight hole 38. A transparent magnet may also be used.

A display 40 is preferably provided for numerically displaying the intraocular pressure detected by the system. The display 40 preferably comprises a liquid crystal display (LCD) or light emitting diode (LED) display connected and responsive to the conversion unit 34 of the calculation unit 10.

Alternatively, the display 40 can be arranged so as to give indications of whether the intraocular pressure is within certain ranges. In this regard, the display 40 may include a green LED 40A, a yellow LED 40B, and a red LED 40C. When the pressure is within a predetermined high range, the red LED 40C is illuminated to indicate that medical attention is needed. When the intraocular pressure is within a normal range, the green LED 40A is illuminated. The yellow LED 40B is illuminated when the pressure is between the normal range and the high range to indicate that the pressure is somewhat elevated and that, although medical attention is not currently needed, careful and frequent monitoring is recommended.

Preferably, since different patients may have different sensitivities or reactions to the same intraocular pressure, the ranges corresponding to each LED 40A,40B,40C are calibrated for each patient by an attending physician. This way, patients who are more susceptible to consequences from increased intraocular pressure may be alerted to seek medical attention at a pressure less than the pressure at which other less-susceptible patients are alerted to take the same action. The range calibrations may be made using any known calibration device 40D including variable gain amplifiers or voltage divider networks with variable resistances.

The detecting arrangement 8 preferably comprises an optical detection system including two primary beam emitters 44,46; two light sensors 48,50; and two converging lenses 52,54. Any of a plurality of commercially available beam emitters may be used as emitters 44,46, including low-power laser beam emitting devices and infra-red (IR) beam emitting devices. Preferably, the device 2 and the primary beam emitters 44,46 are arranged with respect to one another so that each of the primary beam emitters 44,46 emits a primary beam of light toward the cornea through the transparent area 22 of the device and so that the primary beam of light is reflected back through the device 2 by the cornea 4 to thereby produce reflected beams 60,62 of light with a direction of propagation dependent upon the amount of applanation of the cornea. The two light sensors 48,50 and two converging lenses 52,54 are preferably arranged so as to be aligned with the reflected beams 60,62 of light only when the predetermined amount of applanation of the cornea 4 has been achieved. Preferably, the primary beams 56,58 pass through the substantially transparent peripheral portion 36.

Although FIG. 1 shows the reflected beams 60,62 of light diverging away from one another and well away from the two converging lenses 52,54 and light sensors 48,50, it is understood that as the cornea 4 becomes applanated the reflected beams 60,62 will approach the two light sensors 48,50 and the two converging lenses 52,54. When the predetermined amount of applanation is achieved, the reflected beams 60,62 will be directly aligned with the converging lenses 52,54 and the sensors 48,50. The sensors 48,50 are therefore able to detect when the predetermined amount of applanation is achieved by merely detecting the presence of the reflected beams 60,62. Preferably, the predetermined amount of applanation is deemed to exist when all of the sensors 48,50 receive a respective one of the reflected beams 60,62.

Although the illustrated arrangement is generally effective using two primary beam emitters 44,46 and two light sensors 48,50, better accuracy can be achieved in patients with astigmatisms by providing four beam emitters and four light sensors arranged orthogonally with respect to one another about the longitudinal axis of the actuation apparatus 6. As in the case with two beam emitters 44,46 and light sensors 48,50, the predetermined amount of applanation is preferably deemed to exist when all of the sensors receive a respective one of the reflected beams.

A sighting arrangement is preferably provided for indicating when the actuation apparatus 6 and the detecting arrangement 8 are properly aligned with the device 2. Preferably, the sighting arrangement includes the central sight hole 38 in the movable central piece 16 through which a patient is able to see while the device 2 is located on the patient's cornea 4. The central sight hole 38 is aligned with the transparent area 22. In addition, the actuation apparatus 6 includes a tubular housing 64 having a first end 66 for placement over an eye equipped with the device 2 and a second opposite end 68 having at least one mark 70 arranged such that, when the patient looks through the central sight hole 38 at the mark 70, the device 2 is properly aligned with the actuation apparatus 6 and detecting arrangement 8.

Figure 3:
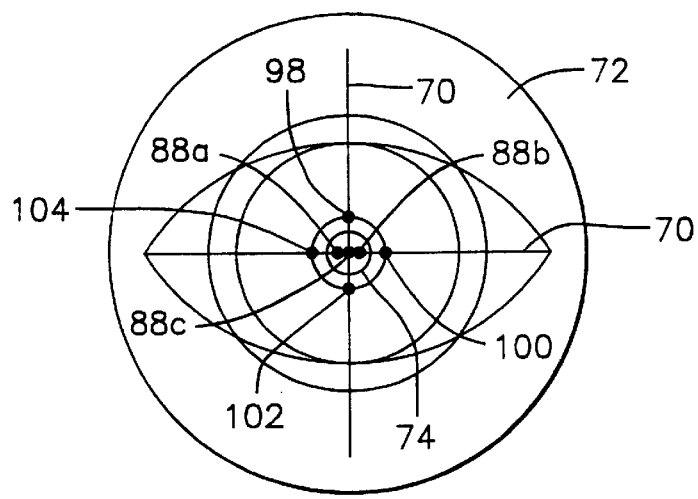
FIG. 3 schematically illustrates a view seen by a patient when utilizing the system illustrated in FIG. 1.

Preferably, the second end 68 includes an internal mirror surface 72 and the mark 70 generally comprises a set of cross-hairs. FIG. 3 illustrates the view seen by a patient through the central sight hole 38 when the device 2 is properly aligned with the actuation apparatus 6 and detecting arrangement 8. When proper alignment is achieved, the reflected image 74 of the central sight hole 38 appears in the mirror surface 72 at the intersection of the two cross-hairs which constitute the mark 70. (The size of the image 74 is exaggerated in FIG. 3 to more clearly distinguish it from other elements in the drawing).

Preferably, at least one light 75 is provided inside the tubular housing 64 to illuminate the inside of the housing 64 and facilitate visualation of the cross-hairs and the reflected image 74. Preferably, the internal mirror surface 72 acts as a mirror only when the light 75 is on, and becomes mostly transparent upon deactivation of the light 75 due to darkness inside the tubular housing 64. To that end, the second end 68 of the tubular housing 68 may be manufactured using "one-way glass" which is often found in security and surveillance equipment.

Alternatively, if the device is to be used primarily by physicians, optometrists, or the like, the second end 68 may be merely transparent. If, on the other hand, the device is to be used by patients for self-monitoring, it is understood that the second end 68 may merely include a mirror.

The system also preferably includes an optical distance measuring mechanism for indicating whether the device 2 is spaced at a proper axial distance from the actuation apparatus 6 and the detecting arrangement 8. The optical distance measurement mechanism is preferably used in conjunction with the sighting arrangement.

Preferably, the optical distance measuring mechanism includes a distance measurement beam emitter 76 for emitting an optical distance measurement beam 78 toward the device 2. The device 2 is capable of reflecting the distance measurement beam 78 to produce a first reflected distance measurement beam 80. Arranged in the path of the first reflected distance measurement beam 80 is a preferably convex mirror 82. The convex mirror 82 reflects the first reflected distance measurement beam 80 to create a second reflected distance measurement beam 84 and serves to amplify any variations in the first reflected beam's direction of propagation. The second reflected distance measurement beam 84 is directed generally toward a distance measurement beam detector 86. The distance measurement beam detector 86 is arranged so that the second reflected distance measurement beam 84 strikes a predetermined portion of the distance measurement beam detector 86 only when the device 2 is located at the proper axial distance from the actuation apparatus 6 and the detecting arrangement 8. When the proper axial distance is lacking, the second reflected distance measurement beam strikes another portion of the beam detector 86.

An indicator 88, such as an LCD or LED display, is preferably connected and responsive to the beam detector 86 for indicating that the proper axial distance has been achieved only when the reflected distance measurement beam strikes the predetermined portion of the distance measurement beam detector.

Preferably, as illustrated in FIG. 1, the distance measurement beam detector 86 includes a multi-filter optical element 90 arranged so as to receive the second reflected distance measurement beam 84. The multi-filter optical element 90 contains a plurality of optical filters 92. Each of the optical filters 92 filters out a different percentage of light, with the predetermined portion of the detector 86 being defined by a particular one of the optical filters 92 and a filtering percentage associated therewith.

The distance measurement beam detector 86 further includes a beam intensity detection sensor 94 for detecting the intensity of the second reflected distance measurement beam 84 after the beam 84 passes through the multi-filter optical element 90. Since the multi-filter optical element causes this intensity to vary with axial distance, the intensity is indicative of whether the device 2 is at the proper distance from the actuation apparatus 6 and the detecting arrangement 8.

A converging lens 96 is preferably located between the multi-filter optical element 90 and the beam intensity detection sensor 94, for focussing the second reflected distance measurement beam 84 on the beam intensity detection sensor 94 after the beam 84 passes through the multi-filter optical element 90.

Preferably, the indicator 88 is responsive to the beam intensity detection sensor 94 so as to indicate what corrective action should be taken, when the device 2 is not at the proper axial distance from the actuation apparatus 6 and the detecting arrangement 8, in order to achieve the proper distance. The indication given by the indicator 88 is based on the intensity and which of the plurality of optical filters 92 achieves the particular intensity by virtue of a filtering percentage associated therewith.

For example, when the device 2 is excessively far from the actuation apparatus 6, the second reflected distance measurement beam 84 passes through a dark one of the filters 92. There is consequently a reduction in beam intensity which causes the beam intensity detection sensor 94 to drive the indicator 88 with a signal indicative of the need to bring the device 2 closer to the actuation apparatus. The indicator 88 responds to this signal by communicating the need to a user of the system.

Alternatively, the signal indicative of the need to bring the device 2 closer to the actuation apparatus can be applied to a computer which performs corrections automatically.

In like manner, when the device 2 is excessively close to the actuation apparatus 6, the second reflected distance measurement beam 84 passes through a lighter one of the filters 92. There is consequently an increase in beam intensity which causes the beam intensity detection sensor 94 to drive the indicator 88 with a signal indicative of the need to move the device 2 farther from the actuation apparatus. The indicator 88 responds to this signal by communicating the need to a user of the system.

In addition, computer-controlled movement of the actuation apparatus farther away from the device 2 may be achieved automatically by providing an appropriate computer-controlled moving mechanism responsive to the signal indicative of the need to move the device 2 farther from the actuation apparatus.

With reference to FIG. 3, the indicator 88 preferably comprises three LEDs arranged in a horizontal line across the second end 68 of the housing 64. When illuminated, the left LED 88a, which is preferably yellow, indicates that the contact device 2 is too far from the actuation apparatus 6 and the detecting arrangement 8. Similarly, when illuminated, the right LED 88b, which is preferably red, indicates that the contact device 2 is too close to the actuation apparatus 6 and the detecting arrangement 8. When the proper distance is achieved, the central LED 88c is illuminated. Preferably, the central LED 88c is green. The LEDs 88a–88c are selectively illuminated by the beam intensity detection sensor 94 in response to the beam's intensity.

Although FIG. 1 illustrates an arrangement of filters 92 wherein a reduction in intensity signifies a need to move the device closer, it is understood that the present invention is not limited to such an arrangement. The multi-filter optical element 90, for example, may be reversed so that the darkest of the filters 92 is positioned adjacent the end 68 of the tubular housing 64. When such an arrangement is used, an increase in beam intensity would signify a need to move the device 2 farther away from the actuation apparatus 6.

Preferably, the actuation apparatus 6 (or at least the coil 30 thereof) is slidably mounted within the housing 64 and a knob and gearing (e.g., rack and pinion) mechanism are provided for selectively moving the actuation apparatus 6 (or coil 30 thereof) axially through the housing 64 in a perfectly linear manner until the appropriate axial distance from the contact device 2 is achieved. When such an arrangement is provided, the first end 66 of the housing 64 serves as a positioning mechanism for the contact device 2 against which the patient presses the facial area surrounding eye to be examined. once the facial area rests against the first end 66, the knob and gearing mechanism are manipulated to place the actuation apparatus 6 (or coil 30 thereof) at the proper axial distance from the contact device 2.

Although facial contact with the first end 66 enhances stability, it is understood that facial contact is not an essential step in utilizing the present invention.

The system also preferably includes an optical alignment mechanism for indicating whether the device 2 is properly aligned with the actuation apparatus 6 and the detecting arrangement 8. The optical alignment mechanism includes two alignment beam detectors 48',50' for respectively detecting the reflected beams 60,62 of light prior to any applanation. The alignment beam detectors 48',50' are arranged so that the reflected beams 60,62 of light respectively strike a predetermined portion of the alignment beam detectors 48',50' prior to applanation only when the device 2 is properly aligned with respect to the actuation apparatus 6 and the detecting arrangement 8. When the device 2 is not properly aligned, the reflected beams 60,62 strike another portion of the alignment beam detectors 48',50', as will be described hereinafter.

The optical alignment mechanism further includes an indicator arrangement responsive to the alignment beam detectors 48',50'. The indicator arrangement preferably includes a set of LEDs 98,100,102,104 which indicate that the proper alignment has been achieved only when the reflected beams 60,62 of light respectively strike the predetermined portion of the alignment beam detectors 48',50' prior to applanation.

Figure 4:
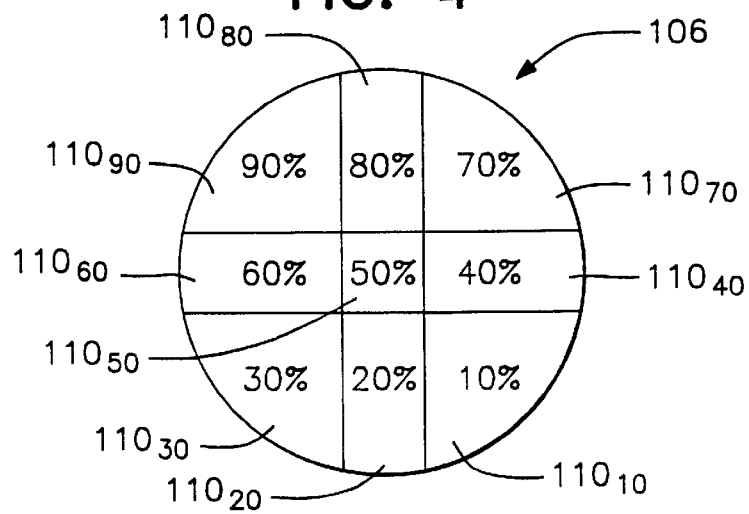
FIGS. 4 and 5 schematically depict multi-filter optical elements in accordance with a preferred embodiment of the present invention.
Figure 5:
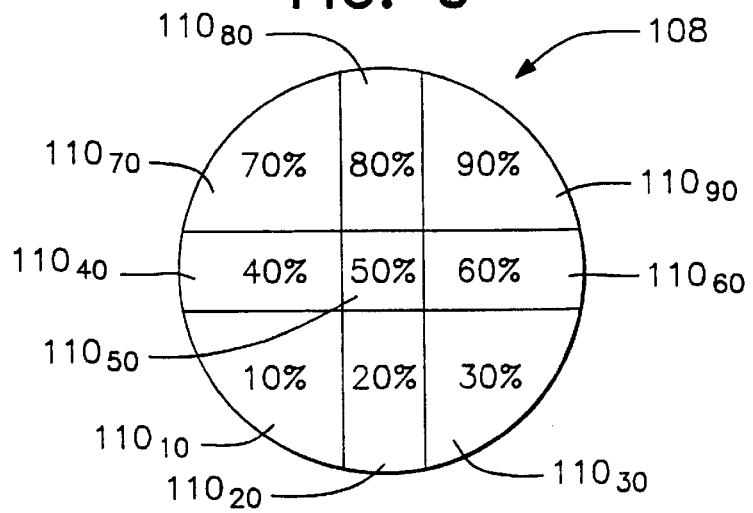
Figure 5A:
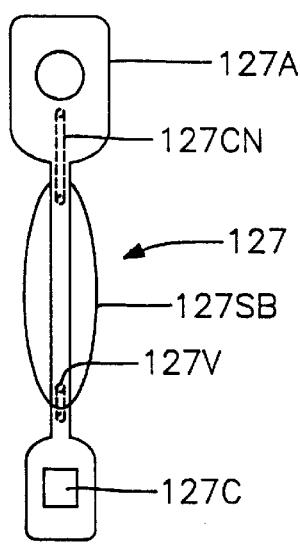
FIGS. 5A–5F illustrate a preferred embodiment of an applicator for gently applying the contact device to the cornea in accordance with the present invention.
Figure 5B:
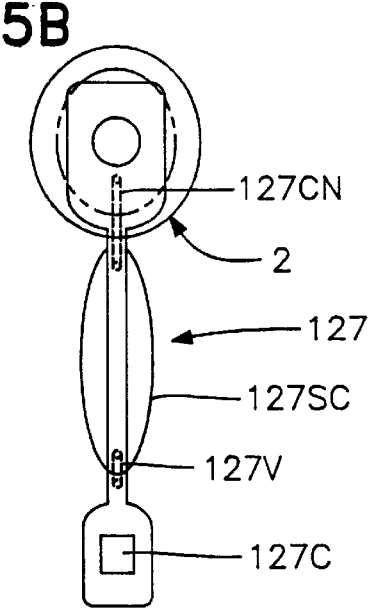
Figure 5C:
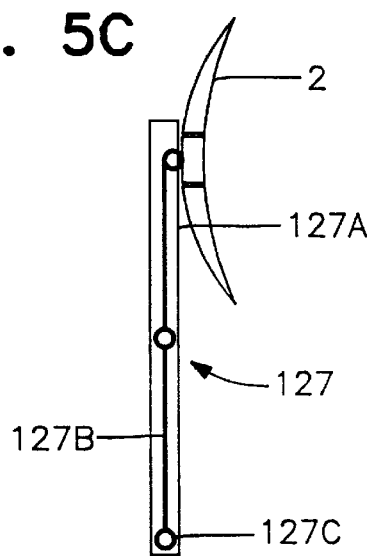
Figure 5D:
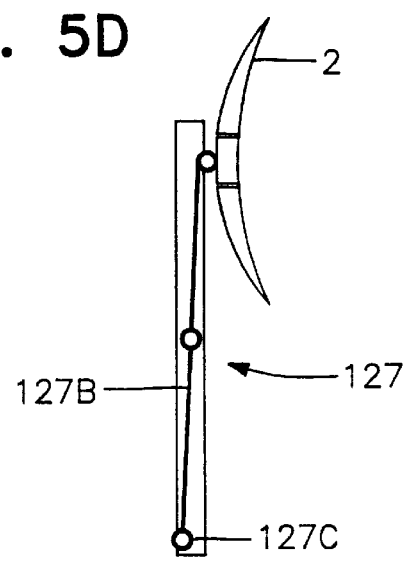
Figure 5E:
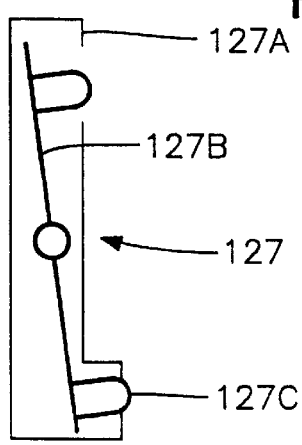
Figure 5F:
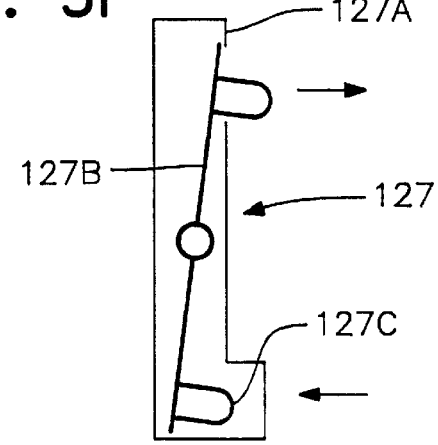

Preferably, each of the alignment beam detectors 48',50' includes a respective multi-filter optical element 106,108. The multi-filter optical elements 106,108 are arranged so as to receive the reflected beams 60,62 of light. Each multi-filter optical element 106,108 contains a plurality of optical filters $110_{10}$–$110_{90}$ (FIGS. 4 and 5), each of which filters out a different percentage of light. In FIGS. 4 and 5, the different percentages are labeled between 10 and 90 percent in increments of ten percent. It is understood, however, that many other arrangements and increments will suffice.

For the illustrated arrangement, it is preferred that the centrally located filters $110_{50}$ which filter out 50% of the light represent the predetermined portion of each alignment beam detector 48',50'. Proper alignment is therefore deemed to exist when the reflected beams 60,62 of light pass through the filters $110_{50}$ and the intensity of the beams 60,62 is reduced by 50%.

Each of the alignment beam detectors 48',50' also preferably includes a beam intensity detector 112,114 for respectively detecting the intensity of the reflected beams 60,62 of light after the reflected beams 60,62 of light pass through the multi-filter optical elements 106,108. The intensity of each beam is indicative of whether the device 2 is properly aligned with respect to the actuation apparatus 6 and the detecting arrangement.

A converging lens 116,118 is preferably located between each multi-filter optical element 106,108 and its respective beam intensity detector 112,114. The converging lens 116, 118 focusses the reflected beams 60,62 of light onto the beam intensity detectors 112,114 after the reflected beams 60,62 pass through the multi-filter optical elements 106,108.

Each of the beam intensity detectors 112,114 has its output connected to an alignment beam detection circuit which, based on the respective outputs from the beam intensity detectors 112,114, determines whether there is proper alignment, and if not, drives the appropriate one or ones of the LEDs 98,100,102,104 to indicate the corrective action which should be taken.

As illustrated in FIG. 3, the LEDs 98,100,102,104 are respectively arranged above, to the right of, below, and to the left of the intersection of the cross-hairs 70. No LEDs 98,100,102,104 are illuminated unless there is a misalignment. Therefore, a lack of illumination indicates that the device 2 is properly aligned with the actuation apparatus 6 and the detecting arrangement 8.

When the device 2 on the cornea 4 is too high, the beams 56,58 of light strike a lower portion of the cornea 4 and because of the cornea's curvature, are reflected in a more downwardly direction. The reflected beams 60,62 therefore impinge on the lower half of the multi-filter elements 106,108, and the intensity of each reflected beam 60,62 is reduced by no more than 30%. The respective intensity reductions are then communicated to the alignment detection circuit 120 by the beam intensity detectors 112,114. The alignment detection circuit 120 interprets this reduction of intensity to result from a misalignment wherein the device 2 is too high. The alignment detection circuit 120 therefore causes the upper LED 98 to illuminate. Such illumination indicates to the user that the device 2 is too high and must be lowered with respect to the actuation apparatus 6 and the detecting arrangement 8.

Similarly, when the device 2 on the cornea 4 is too low, the beams 56,58 of light strike an upper portion of the cornea 4 and because of the cornea's curvature, are reflected in a more upwardly direction. The reflected beams 60,62 therefore impinge on the upper half of the multi-filter elements 106,108, and the intensity of each reflected beam 60,62 is reduced by at least 70%. The respective intensity reductions are then communicated to the alignment detection circuit 120 by the beam intensity detectors 112,114. The alignment detection circuit 120 interprets this particular reduction of intensity to result from a misalignment wherein the device 2 is too low. The alignment detection circuit 120 therefore causes the lower LED 102 to illuminate. Such illumination indicates to the user that the device 2 is too low and must be raised with respect to the actuation apparatus 6 and the detecting arrangement 8.

With reference to FIG. 1, when the device 2 is too far to the right, the beams 56,58 strike a more leftward side of the cornea 4 and because of the cornea's curvature, are reflected in a more leftward direction. The reflected beams 60,62 therefore impinge on the left halves of the multi-filter elements 106,108. Since the filtering percentages decrease from left to right in multi-filter element 106 and increase from left to right in multifilter element 108, there will be a difference in the intensities detected by the beam intensity detectors 112,114. In particular, the beam intensity detector 112 will detect less intensity than the beam intensity detector 114. The different intensities are then communicated to the alignment detection circuit 120 by the beam intensity detectors 112,114. The alignment detection circuit 120 interprets the intensity difference wherein the intensity at the beam intensity detector 114 is higher than that at the beam intensity detector 112, to result from a misalignment wherein the device 2 is too far to the right in FIG. 1 (too far to the left in FIG. 3). The alignment detection circuit 120 therefore causes the left LED 104 to illuminate. Such illumination indicates to the user that the device 2 is too far to the left (in FIG. 3) and must be moved to the right (left in FIG. 1) with respect to the actuation apparatus 6 and the detecting arrangement 8.

Similarly, when the device 2 in FIG. 1 is too far to the left, the beams 56,58 strike a more rightward side of the cornea 4 and because of the cornea's curvature, are reflected in a more rightwardly direction. The reflected beams 60,62 therefore impinge on the right halves of the multi-filter elements 106,108. Since the filtering percentages decrease from left to right in multi-filter element 106 and increase from left to right in multifilter element 108, there will be a difference in the intensities detected by the beam intensity detectors 112,114. In particular, the beam intensity detector 112 will detect more intensity than the beam intensity detector 114. The different intensities are then communicated to the alignment detection circuit 120 by the beam intensity detectors 112,114. The alignment detection circuit 120 interprets the intensity difference wherein the intensity at the beam intensity detector 114 is lower than that at the beam intensity detector 112, to result from a misalignment wherein the device 2 is too far to the left in FIG. 1 (too far to the right in FIG. 3). The alignment detection circuit 120 therefore causes the right LED 100 to illuminate. Such illumination indicates to the user that the device 2 is too far to the right (in FIG. 3) and must be moved to the left (right in FIG. 1) with respect to the actuation apparatus 6 and the detecting arrangement 8.

The combination of LEDs 98,100,102,104 and the alignment detection circuit 120 therefore constitutes a display arrangement which is responsive to the beam intensity detectors 112,114 and which indicates what corrective action should be taken, when the device 2 is not properly aligned, in order to achieve proper alignment. Preferably, the substantially transparent peripheral portion 36 of the movable central piece 16 is wide enough to permit passage of the beams 56,58 to the cornea 4 even during misalignment.

It is understood that automatic alignment correction may be provided via computer-controlled movement of the actuation apparatus upwardly, downwardly, to the right, and/or to the left, which computer-controlled movement may be generated by an appropriate computer-controlled moving mechanism responsive to the optical alignment mechanism.

The optical alignment mechanism is preferably used in conjunction with the sighting arrangement, so that the optical alignment mechanism merely provides indications of minor alignment corrections while the sighting arrangement provides an indication of major alignment corrections. It is understood, however, that the optical alignment mechanism can be used in lieu of the sighting mechanism if the substantially transparent peripheral portion 36 is made wide enough.

Although the foregoing alignment mechanism uses the same reflected beams 60,62 used by the detecting arrangement 8, it is understood that separate alignment beam emitters may be used in order to provide separate and distinct alignment beams. The foregoing arrangement is preferred because it saves the need to provide additional emitters and thus is less expensive to manufacture.

Nevertheless, optional alignment beam emitters 122,124 are illustrated in FIG. 1. The alignment mechanism using these optional alignment beam emitters 122,124 would operate in essentially the same manner as its counterpart which uses the reflected beams 60,62.

In particular, each of the alignment beam emitters 122,124 emits an optical alignment beam toward the device 2. The alignment beam is reflected by the cornea 4 to produce a reflected alignment beam. The alignment beam detectors 48',50' are arranged so as to receive, not the reflected beams 60,62 of light, but rather the reflected alignment beams when the alignment beam emitters 122,124 are present. More specifically, the reflected alignment beams strike a predetermined portion of each alignment beam detector 48',50' prior to applanation only when the device 2 is properly aligned with respect to the actuation apparatus 6 and the detecting arrangement 8. The rest of the system preferably includes the same components and operates in the same manner as the system which does not use the optional. alignment beam emitters 122, 124.

The system may further include an applicator for gently placing the contact device 2 on the cornea 4. As illustrated in FIGS. 5A–5F, a preferred embodiment of the applicator 127 includes an annular piece 127A at the tip of the applicator 127. The annular piece 127A matches the shape of the movable central piece 16. Preferably, the applicator 127 also includes a conduit 127CN having an open end which opens toward the annular piece 127A. An opposite end of the conduit 127CN is connected to a squeeze bulb 127SB. The squeeze bulb 127SB includes a one-way valve 127V which permits the flow of air into the squeeze bulb 127SB, but prevents the flow of air out of the squeeze bulb 127SB through the valve 127V. When the squeeze bulb 127SB is squeezed and then released, a suction effect is created at the open end of the conduit 127CN as the squeeze bulb 127SB tries to expand to its pre-squeeze shape. This suction effect may be used to retain the contact device 2 at the tip of the applicator 127.

In addition, a pivoted lever system 127B is arranged to detach the movable central piece 16 from the annular piece 127A when a knob 127C at the base of the applicator 127 is pressed, thereby nudging the contact device 2 away from the annular piece 127A.

Alternatively, the tip of the applicator 127 may be selectively magnetized and demagnetized using electric current flowing through the annular piece 127A. This arrangement replaces the pivoted lever system 127B with a magnetization mechanism capable of providing a magnetic field which repels the movable central piece 16, thereby applying the contact device 2 to the cornea 4.

Figure 6:
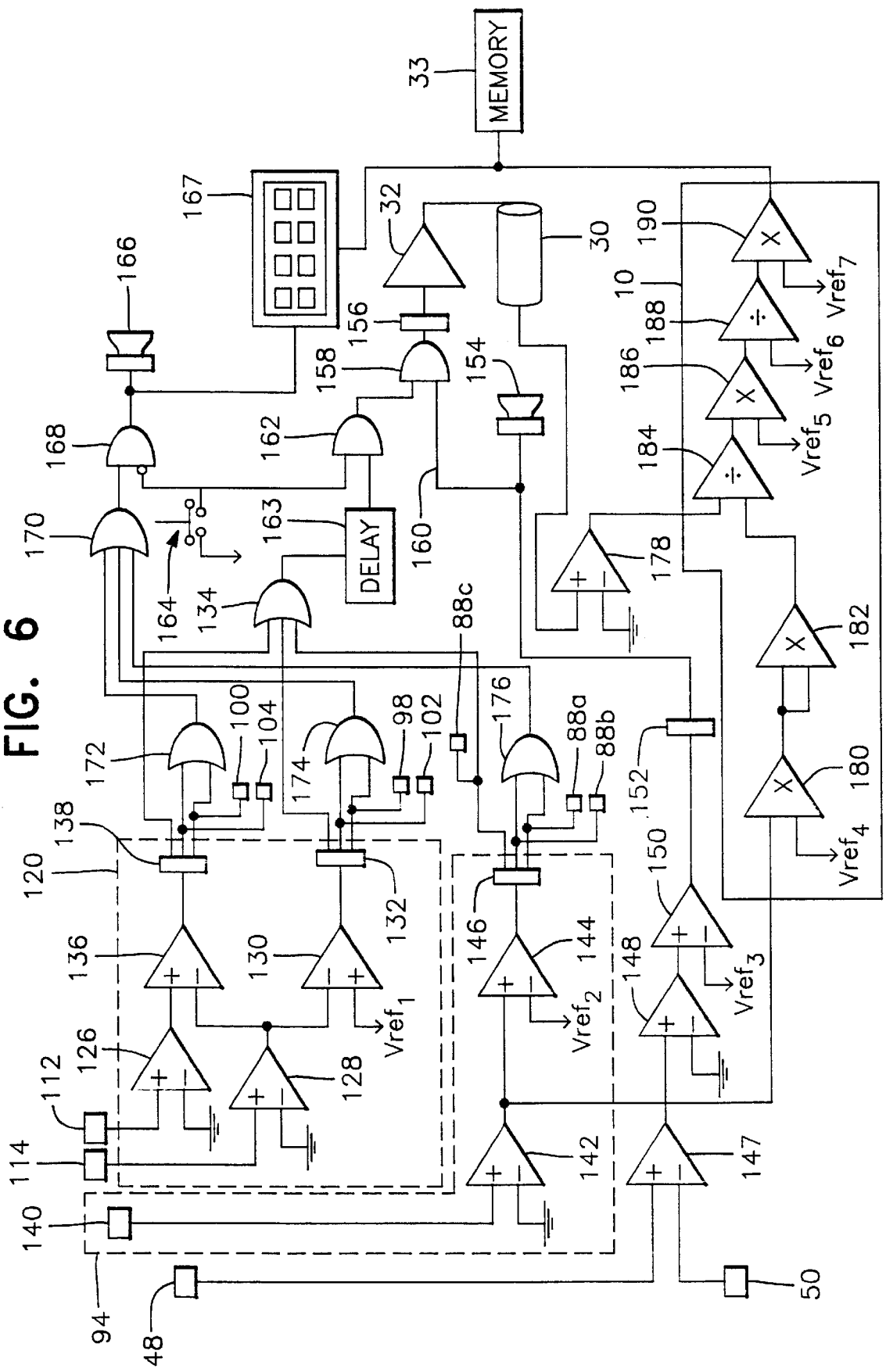
FIG. 6 illustrates an exemplary circuit for carrying out several aspects of the embodiment illustrated in FIG. 1.

A preferred circuit arrangement for implementing the above combination of elements is illustrated schematically in FIG. 6. According to the preferred circuit arrangement, the beam intensity detectors 112,114 comprise a pair of photosensors which provide a voltage output proportional to the detected beam intensity. The output from each beam intensity detector 112,114 is respectively connected to the non-inverting input terminal of a filtering amplifier 126,128. The inverting terminals of the filtering amplifiers 126,128 are connected to ground. The amplifiers 126,128 therefore provide a filtering and amplification effect.

In order to determine whether proper vertical alignment exists, the output from the filtering amplifier 128 is applied to an inverting input terminal of a vertical alignment comparator 130. The vertical alignment comparator 130 has its non-inverting input terminal connected to a reference voltage $Vref_1$. The reference voltage $Vref_1$ is selected so that it approximates the output from the filtering amplifier 128 whenever the light beam 62 strikes the central row of filters $110_{40\text{-}60}$ of the multi-filter optical element 108 (i.e., when the proper vertical alignment is achieved).

Consequently, the output from the comparator 130 is approximately zero when proper vertical alignment is achieved, is significantly negative when the contact device 2 is too high, and is significantly positive when the contact device 2 is too low. This output from the comparator 130 is then applied to a vertical alignment switch 132. The vertical alignment switch 132 is logically arranged to provide a positive voltage to an AND-gate 134 only when the output from the comparator 130 is approximately zero, to provide a positive voltage to the LED 98 only when the output from the comparator 130 is negative, and to provide a positive voltage to the LED 102 only when the output from the comparator 130 is positive. The LEDs 98,102 are thereby illuminated only when there is a vertical misalignment and each illumination clearly indicates what corrective action should to be taken.

In order to determine whether proper horizontal alignment exists, the output from the filtering amplifier 126 is applied to a non-inverting input terminal of a horizontal alignment comparator 136, while the inverting input terminal of the horizontal alignment comparator 136 is connected to the output from the filtering amplifier 128. The comparator 136 therefore produces an output which is proportional to the difference between the intensities detected by the beam intensity detectors 112,114. This difference is zero whenever the light beams 60,62 strike the central column of filters 110$_{20}$, 110$_{50}$, 110$_{80}$ of the multi-filter optical elements 106,108 (i.e., when the proper horizontal alignment is achieved).

The output from the comparator 136 is therefore zero when the proper horizontal alignment is achieved, is negative when the contact device 2 is too far to the right (in FIG. 1), and is positive when the contact device 2 is too far to the left (in FIG. 1). This output from the comparator 130 is then applied to a horizontal alignment switch 138. The horizontal alignment switch 138 is logically arranged to provide a positive voltage to the AND-gate 134 only when the output from the comparator 136 is zero, to provide a positive voltage to the LED 104 only when the output from the comparator 136 is negative, and to provide a positive voltage to the LED 100 only when the output from the comparator 136 is positive. The LEDs 100, 104 are thereby illuminated only when there is a horizontal misalignment and each illumination clearly indicates what corrective action should be taken.

In accordance with the preferred circuit arrangement illustrated in FIG. 6, the beam intensity detection sensor 94 of the distance measurement beam detector 86 includes a photosensor 140 which produces a voltage output proportional to the detected beam intensity. This voltage output is applied to the non-inverting input terminal of a filtering amplifier 142. The inverting terminal of the filtering amplifier 142 is connected to ground. Accordingly, the filtering amplifier 142 filters and amplifies the voltage output from the photosensor 140. The output from the filtering amplifier 142 is applied to the non-inverting input terminal of a distance measurement comparator 144. The comparator 144 has its inverting terminal connected to a reference voltage Vref$_2$. Preferably, the reference voltage Vref$_2$ is selected so as to equal the output of the filtering amplifier 142 only when the proper axial distance separates the contact device 2 from the actuation apparatus 6 and detecting arrangement 8.

Consequently, the output from the comparator 144 is zero whenever the proper axial distance is achieved, is negative whenever the second reflected beam 84 passes through a dark portion of the multi-filter optical element 90 (i.e., whenever the axial distance is too great), and is positive whenever the second reflected beam 84 passes through a light portion of the multi-filter optical element 90 (i.e., whenever the axial distance is too short).

The output from the comparator 144 is then applied to a distance measurement switch 146. The distance measurement switch 146 drives the LED 88c with positive voltage whenever the output from the comparator 144 is zero, drives the LED 88b only when the output from the comparator 144 is positive, and drives the LED 88a only when the output from the comparator 144 is negative. The LEDs 88a,88b are thereby illuminated only when the axial distance separating the contact device 2 from the actuation apparatus 6 and the detecting arrangement 8 is improper. Each illumination clearly indicates what corrective action should be taken. Of course, when the LED 88c is illuminated, no corrective action is necessary.

With regard to the detecting arrangement 8, the preferred circuit arrangement illustrated in FIG. 6 includes the two light sensors 48,50. The outputs from the light sensors 48,50 are applied to and added by an adder 147. The output from the adder 147 is then applied to the non-inverting input terminal of a filtering amplifier 148. The inverting input terminal of the same amplifier 148 is connected to ground. As a result, the filtering amplifier 148 filters and amplifies the sum of the output voltages from the light sensor 48,50. The output from the filtering amplifier 148 is then applied to the non-inverting input terminal of an applanation comparator 150. The inverting input terminal of the applanation comparator 150 is connected to a reference voltage Vref$_3$. Preferably, the reference voltage Vref$_3$ is selected so as to equal the output from the filtering amplifier 148 only when the predetermined amount of applanation is achieved (i.e., when the reflected beams 60,62 strike the light sensors 48,50). The output from the applanation comparator 150 therefore remains negative until the predetermined amount of applanation is achieved.

The output from the applanation comparator 150 is connected to an applanation switch 152. The applanation switch 152 provides a positive output voltage when the output from the applanation comparator 150 is negative and terminates its positive output voltage whenever the output from the applanation comparator 150 becomes positive.

Preferably, the output from the applanation switch 152 is connected to an applanation speaker 154 which audibly indicates when the predetermined amount of applanation has been achieved. In particular, the speaker 154 is activated whenever the positive output voltage from the applanation, switch 152 initially disappears.

In the preferred circuit of FIG. 6, the coil 30 is electrically connected to the current producing circuitry 32 which, in turn, includes a signal generator capable of producing the progressively increasing current in the coil 30. The current producing circuitry 32 is controlled by a start/stop switch 156 which is selectively activated and deactivated by an AND-gate 158.

The AND-gate 158 has two inputs, both of which must exhibit positive voltages in order to activate the start/stop switch 156 and current producing circuitry 32. A first input 160 of the two inputs is the output from the applanation switch 152. Since the applanation switch 152 normally has a positive output voltage, the first input 160 remains positive and the AND-gate is enabled at least with respect to the first input 160. However, whenever the predetermined amount of applanation is achieved (i.e. whenever the positive output voltage is no longer present at the output from the applanation switch 152), the AND-gate 158 deactivates the current producing circuitry 32 via the start/stop switch 156.

The second input to the AND-gate 158 is the output from another AND-gate 162. The other AND-gate 162 provides a positive output voltage only when a push-action switch 164 is pressed and only when the contact device 2 is located at the proper axial distance from, and is properly aligned both vertically and horizontally with, the actuation apparatus 6 and the detecting arrangement 8. The current producing circuitry 32 therefore cannot be activated unless there is proper alignment and the proper axial distance has been achieved. In order to achieve such operation, the output from the AND-gate 134 is connected to a first input of the AND-gate 162 and the push-action switch 164 is connected to the second input of the AND-gate 162.

A delay element 163 is located electrically between the AND-gate 134 and the AND-gate 162. The delay element 163 maintains a positive voltage at the first input terminal to the AND-gate 162 for a predetermined period of time after a positive voltage first appears at the output terminal of the AND-gate 134. The primary purpose of the delay element 163 is to prevent deactivation of the current producing circuitry 32 which would otherwise occur in response to changes in the propagation direction of the reflected beams 60,62 during the initial stages of applanation. The predetermined period of time is preferably selected pursuant to the maximum amount of time that it could take to achieve the predetermined amount of applanation.

According to the preferred circuitry illustrated in FIG. 6, misalignment and improper axial separation of the contact device 2 with respect to the actuation apparatus 6 and detecting arrangement 8 is audibly announced by a speaker 166 and causes deactivation of a display 167. The display 167 and speaker 166 are connected and responsive to an AND-gate 168. The AND-gate 168 has an inverting input connected to the push-action switch 164 and another input connected to a three-input OR-gate 170.

Therefore, when the push-action switch 164 is activated, the inverting input terminal of the AND-gate 168 prevents a positive voltage from appearing at the output from the AND-gate 168. Activation of the speaker 166 is thereby precluded. However, when the push-action switch is not activated, any positive voltage at any of the three inputs to the OR-gate 170 will activate the speaker 166. The three inputs to the OR-gate 170 are respectively connected to outputs from three other OR-gates 172,174,176. The OR-gates 172,174,176, in turn, have their inputs respectively connected to the LEDs 100,104, LEDs 98,102, and LEDs 88a,88b. Therefore, whenever any one of these LEDs 88a, 88b, 98, 100, 102, 104 is activated, the OR-gate 170 produces a positive output voltage. The speaker 166, as a result, will be activated whenever any one of the LEDs 88a,88b,98,100,102,104 is activated while the push-action switch 164 remains deactivated.

Turning now to the current producing circuitry 32, the output from the current producing circuitry 32 is connected to the coil 30. The coil 30, in turn, is connected to a current-to-voltage transducer 178. The output voltage from the current-to-voltage transducer 178 is proportional to the current flowing through the coil 30 and is applied to the calculation unit 10.

The calculation unit 10 receives the output voltage from the transducer 178 and converts this output voltage indicative of current to an output voltage indicative of intraocular pressure. Initially, an output voltage from the filtering amplifier 142 indicative of the axial distance separating the contact device 2 from the actuation apparatus 6 and the detecting arrangement 8, is multiplied by a reference voltage $Vref_4$ using a multiplier 180. The reference voltage $Vref_4$ represents a distance calibration constant. The output from the multiplier 180 is then squared by a multiplier 182 to create an output voltage indicative of distance squared ($d^2$).

The output from the multiplier 182 is then supplied to an input terminal of a divider 184. The other input terminal of the divider 184 receives the output voltage indicative of current from the current-to-voltage transducer 178. The divider 184 therefore produces an output voltage indicative of the current in the coil 30 divided by the distance squared ($I/d^2$).

The output voltage from the divider 184 is then applied to a multiplier 186. The multiplier 186 multiplies the output voltage from the divider 184 by a reference voltage $Vref_5$. The reference voltage $Vref_5$ corresponds to a conversion factor for converting the value of ($I/d^2$) to a value indicative of force in Newtons being applied by the movable central piece 16 against the cornea 4. The output voltage from the multiplier 186 is therefore indicative of the force in Newtons being applied by the movable central piece 16 against the cornea.

Next, the output voltage from the multiplier 186 is applied to an input terminal of a divider 188. The other input terminal of the divider 188 receives a reference voltage $Vref_6$. The reference voltage $Vref_6$ corresponds to a calibration constant for converting force (in Newtons) to pressure (in Pascals) depending on the surface area of the movable central piece's substantially flat inner side 24. The output voltage from the divider 188 is therefore indicative of the pressure (in Pascals) being exerted by the cornea 4 against the inner side of the movable central piece 16 in response to displacement of the movable central piece 16.

Since the pressure exerted by the cornea 4 depends upon the surface area of the substantially flat inner side 24, the output voltage from the divider 188 is indicative of intraocular pressure only when the cornea 4 is being applanated by the entire surface area of the inner side 24. This, in turn, corresponds to the predetermined amount of applanation.

Preferably, the output voltage indicative of intraocular pressure is applied to an input terminal of a multiplier 190. The multiplier 190 has another input terminal connected to a reference voltage $Vref_7$. The reference voltage $Vref_7$ corresponds to a conversion factor for converting pressure in Pascals to pressure in millimeters of mercury (mmHg). The voltage output from the multiplier 190 therefore is indicative of intraocular pressure in millimeters of mercury (mmHg) whenever the predetermined amount of applanation is achieved.

The output voltage from the multiplier 190 is then applied to the display 167 which provides a visual display of intraocular pressure based on this output voltage. Preferably, the display 167 or calculation unit 10 includes a memory device 33 which stores a pressure value associated with the output voltage from the multiplier 190 whenever the predetermined amount of applanation is achieved. Since the current producing circuitry 32 is automatically and immediately deactivated upon achieving the predetermined amount of applanation, the intraocular pressure corresponds to the pressure value associated with the peak output voltage from the multiplier 190. The memory therefore can be triggered to store the highest pressure value upon detecting a drop in the output voltage from the multiplier 190. Preferably, the memory is automatically reset prior to any subsequent measurements of intraocular pressure.

Although FIG. 6 shows the display 167 in digital form, it is understood that the display 167 may have any known form. The display 167 may also include the three LEDs 40A,40B,40C illustrated in FIG. 1 which give a visual indication of pressure ranges which, in turn, are calibrated for each patient.

As indicated above, the illustrated calculation unit 10 includes separate and distinct multipliers 180,182,186,190 and dividers 184,188 for converting the output voltage indicative of current into an output voltage indicative of intraocular pressure in millimeters of mercury (mmHg). The separate and distinct multipliers and dividers are preferably provided so that variations in the system's characteristics can be compensated for by appropriately changing the reference voltages $Vref_4$, $Vref_5$, $Vref_6$ and/or $Vref_7$. It is understood, however, that when all of the system's characteristics remain the same (e.g., the surface area of the inner side 24 and the desired distance separating the contact device 2 from the actuation apparatus 6 and detecting arrangement 8) and the conversion factors do not change, that a single conversion factor derived from the combination of each of the other conversion factors can be used along with a single multiplier or divider to achieve the results provided by the various multipliers and dividers shown in FIG. 6.

Although the above combination of elements is generally effective at accurately measuring intraocular pressure in a substantial majority of patients, some patients have unusually thin or unusually thick corneas. This, in turn, may cause slight deviations in the measured intraocular pressure. In order to compensate for such deviations, the circuitry of FIG. 6 may also include a variable gain amplifier 191 (illustrated in FIG. 7A) connected to the output from the multiplier 190. For the majority of patients, the variable gain amplifier 191 is adjusted to provide a gain (g) of one. The variable gain amplifier 191 therefore would have essentially no effect on the output from the multiplier 190.

However, for patients with unusually thick corneas, the gain (g) is adjusted to a positive gain less than one. A gain (g) of less than one is used because unusually thick corneas are more resistant to applanation and consequently result in a pressure indication that exceeds, albeit by a small amount, the actual intraocular pressure. The adjustable gain amplifier 191 therefore reduces the output voltage from the multiplier 190 by a selected percentage proportional to the cornea's deviation from normal corneal thickness.

For patients with unusually thin corneas, the opposite effect would be observed. Accordingly, for those patients, the gain (g) is adjusted to a positive gain greater than one so that the adjustable gain amplifier 191 increases the output voltage from the multiplier 190 by a selected percentage proportional to the cornea's deviation from normal corneal thickness.

Preferably, the gain (g) is manually selected for each patient using any known means for controlling the gain of a variable gain amplifier, for example, a potentiometer connected to a voltage source. As indicated above, the particular gain (g) used depends on the thickness of each patient's cornea which, in turn, can be determined using known corneal pachymetry techniques. Once the corneal thickness is determined, the deviation from the normal thickness is calculated and the gain (g) is set accordingly.

Alternatively, as illustrated in FIG. 7B, the gain (g) may be selected automatically by connecting an output (indicative of corneal thickness) from a known pachymetry apparatus 193 to a buffer circuit 195. The buffer circuit 195 converts the detected corneal thickness to a gain signal associated with the detected thickness'deviation from the normal corneal thickness. In particular, the gain signal produces a gain (g) of one when the deviation is zero, produces a gain (g) greater than one when the detected corneal thickness is less than the normal thickness, and produces a gain (g) less than one when the detected corneal thickness is greater than the normal thickness.

Although FIGS. 7A and 7B illustrate a configuration which compensates only for corneal thickness, it is understood that similar configurations can be used to compensate for corneal curvature, eye size, ocular rigidity, and the like. For levels of corneal curvature which are higher than normal, the gain would be less than one. The gain would be greater than one for levels of corneal curvature which are flatter than normal. Typically, each increase in one diopter of corneal curvature is associated with a 0.34 mm Hg increase in pressure. The intraocular pressure rises 1 mm Hg for very 3 diopters. The gain therefore can be applied in accordance with this general relationship.

In the case of eye size compensation, larger than normal eyes would require a gain which is less than one, while smaller than normal eyes would require a gain which is greater than one.

For patients with "stiffer" than normal ocular rigidities, the gain is less than one, but for patients with softer ocular rigidities, the gain is greater than one.

As when compensating for corneal thickness, the gain may be manually selected for each patient, or alternatively, the gain may be selected automatically by connecting the apparatus of the present invention to a known keratometer when compensating for corneal curvature, and/or a known biometer when compensating for eye size.

Despite not being illustrated, it is understood that the system includes a power supply mechanism for selectively powering the system using either batteries or household AC current.

Operation of the preferred circuitry will now be described. Initially, the contact device 2 is mounted on the corneal surface of a patient and tends to locate itself centrally at the front of the cornea 4 in essentially the same way as conventional contact lenses. The patient then looks through the central sight hole 38 at the intersection of the cross-hairs which define the mark 70, preferably, while the light 75 provided inside the tubular housing 64 is illuminated to facilitate visualization of the cross-hairs and the reflected image 74. A rough alignment is thereby achieved.

Next, the preferred circuitry provides indications of misalignment or improper axial distance should either or both exist. The patient responds to such indications by taking the indicated corrective action.

Once proper alignment is achieved and the proper axial distance exists between the actuation apparatus 6 and the contact device 2, push-action switch 164 is activated and the AND-gate 158 and start/stop switch 156 activate the current producing circuitry 32. In response to activation, the current producing circuitry 32 generates the progressively increasing current in the coil 30. The progressively increasing current creates a progressively increasing magnetic field in the coil 30. The progressively increasing magnetic field, in turn, causes axial displacement of the movable central piece 16 toward the cornea 4 by virtue of the magnetic field's repulsive effect on the magnetically responsive element 26. Since axial displacement of the movable central piece 16 produces a progressively increasing applanation of the cornea 4, the reflected beams 60,62 begin to swing angularly toward the light sensors 48,50. Such axial displacement and increasing applanation continues until both reflected beams 60,62 reach the light sensors 48,50 and the predetermined amount of applanation is thereby deemed to exist. At that instant, the current producing circuit 32 is deactivated by the input 160 to AND-gate 158; the speaker 154 is momentarily activated to give an audible indication that applanation has been achieved; and the intraocular pressure is stored in the memory device 33 and is displayed on display 167.

Although the above-described and illustrated embodiment includes various preferred elements, it is understood that the present invention may be achieved using various other individual elements. For example, the detecting arrangement 8 may utilize various other elements, including elements which are typically utilized in the art of barcode reading.

Figure 8A:
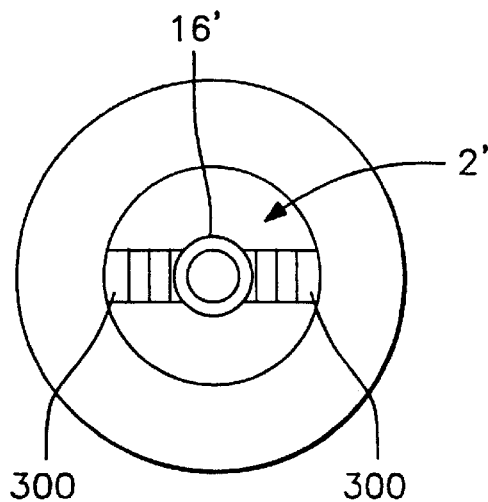
FIGS. 8A and 8B schematically illustrate a contact device utilizing barcode technology in accordance with a preferred embodiment of the present invention.
Figure 8B:
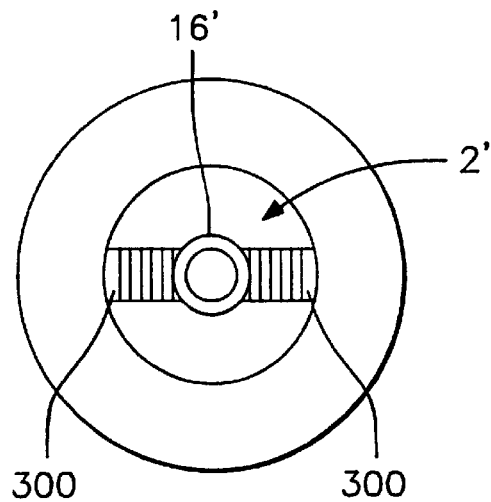

With reference to FIGS. 8A and 8B, a contact device 2' may be provided with a barcode-like pattern 300 which varies in response to displacement of the movable central piece 16'. FIG. 8A illustrates the preferred pattern 300 prior to displacement of the movable central piece 16'; and FIG.

8B shows the preferred pattern 300 when the predetermined amount of applanation is achieved. The detecting arrangement therefore would include a barcode reader directed generally toward the contact device 2' and capable of detecting the differences in the barcode pattern 300.

Figure 9A:
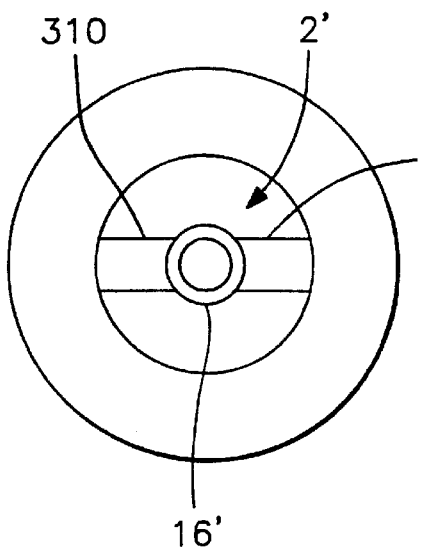
FIGS. 9A and 9B schematically illustrate a contact device utilizing color detection technology in accordance with a preferred embodiment of the present invention.
Figure 9B:
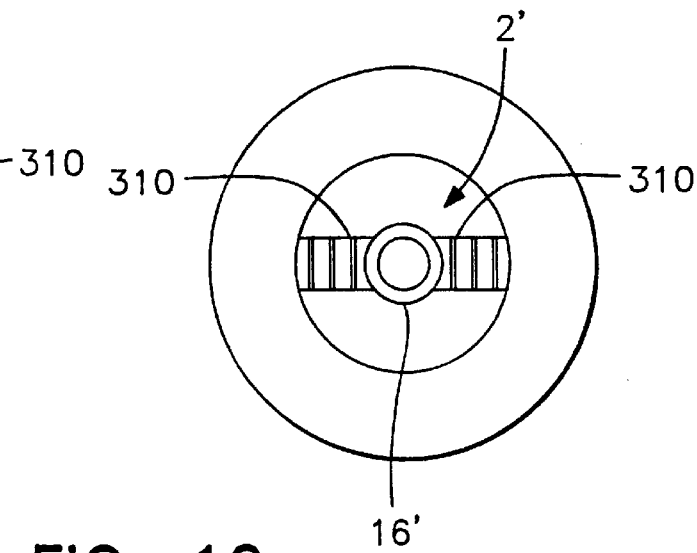

Alternatively, as illustrated in FIGS. 9A and 9E, the contact device 2' may be provided with a multi-color pattern 310 which varies in response to displacement of the movable central piece 16'. FIG. 9A schematically illustrates the preferred color pattern 310 prior to displacement of the movable central piece 16', while FIG. 9B schematically shows the preferred pattern 310 when the predetermined amount of applanation is achieved. The detecting arrangement therefore would include a beam emitter for emitting a beam of light toward the pattern 310 and a detector which receives a reflected beam from the pattern 310 and detects the reflected color to determine whether applanation has been achieved.

Yet another way to detect the displacement of the movable central piece 16 is by using a two dimensional array photosensor that senses the location of a reflected beam of light. Capacitive and electrostatic sensors, as well as changes in magnetic field can then be used to encode the position of the reflected beam and thus the displacement of the movable central piece 16.

Figure 10:
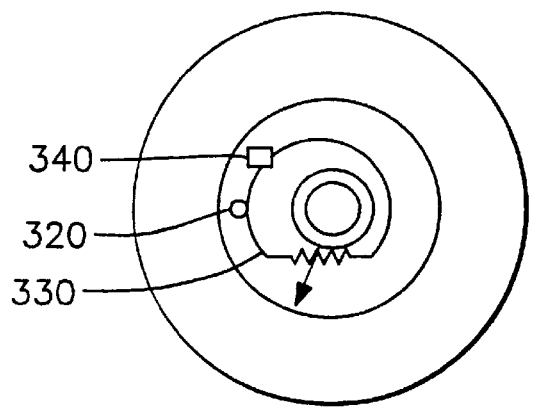
FIG. 10 illustrates an alternative contact device in accordance with yet another preferred embodiment of the present invention.

According to yet another alternative embodiment illustrated in FIG. 10, a miniature LED 320 is inserted into the contact device 2'. The piezoelectric ceramic is driven by ultrasonic waves or is alternatively powered by electromagnetic waves. The brightness of the miniature LED 320 is determined by the current flowing through the miniature LED 320 which, in turn, may be modulated by a variable resistance 330. The motion of the movable central piece 16' varies the variable resistance 330. Accordingly, the intensity of light from the miniature LED 320 indicates the magnitude of the movable central piece's displacement. A miniature, low-voltage primary battery 340 may be inserted into the contact device 2' for powering the miniature LED 320.

With regard to yet another preferred embodiment of the present invention, it is understood that a tear film typically covers the eye and that a surface tension resulting therefrom may cause underestimation of the intraocular pressure. Accordingly, the contact device of the present invention preferably has an inner surface of hydrophobic flexible material in order to decrease or eliminate this potential source of error.

It should be noted that the drawings are merely schematic representations of the preferred embodiments. Therefore, the actual dimensions of the preferred embodiments and physical arrangement of the various elements is not limited to that which is illustrated. Various arrangements and dimensions will become readily apparent to those of ordinary skill in the art. The size of the movable central piece, for example, can be modified for use in animals or experimental techniques. Likewise, the contact device can be made with smaller dimensions for use with infants and patients with eye lid abnormalities.

One preferred arrangement of the present invention includes a handle portion extending out from below the housing 64 and connected distally to a platform. The platform acts as a base for placement on a planar surface (e.g., a table), with the handle projecting up therefrom to support the actuation apparatus 6 above the planar surface.

INDENTATION

The contact device 2 and associated system illustrated in FIGS. 1–5 may also be used to detect intraocular pressure by indentation. When indentation techniques are used in measuring intraocular pressure, a predetermined force is applied against the cornea using an indentation device. Because of the force, the indentation device travels in toward the cornea, indenting the cornea as it travels. The distance travelled by the indentation device into the cornea in response to the predetermined force is known to be inversely proportional to intraocular pressure. Accordingly, there are various known tables which, for certain standard sizes of indentation devices and standard forces, correlate the distance travelled and intraocular pressure.

In utilizing the illustrated arrangement for indentation, the movable central piece 16 of the contact device 2 functions as the indentation device. In addition, the current producing circuit 32 is switched to operate in an indentation mode. When switched to the indentation mode, the current producing circuit 32 supplies a predetermined amount of current through the coil 30. The predetermined amount of current corresponds to the amount of current needed to produce one of the aforementioned standard forces.

The predetermined amount of current creates a magnetic field in the actuation apparatus 6. This magnetic field, in turn, causes the movable central piece 16 to push inwardly against the cornea 4 via the flexible membrane 14. Once the predetermined amount of current has been applied and a standard force presses against the cornea, it is necessary to determine how far the movable central piece 16 moved into the cornea 4.

Accordingly, when measurement of intraocular pressure by indentation is desired, the system illustrated in FIG. 1 further includes a distance detection arrangement for detecting a distance travelled by the movable central piece 16, and a computation portion 199 in the calculation unit 10 for determining intraocular pressure based on the distance travelled by the movable central piece 16 in applying the predetermined amount of force.

Figure 11A:
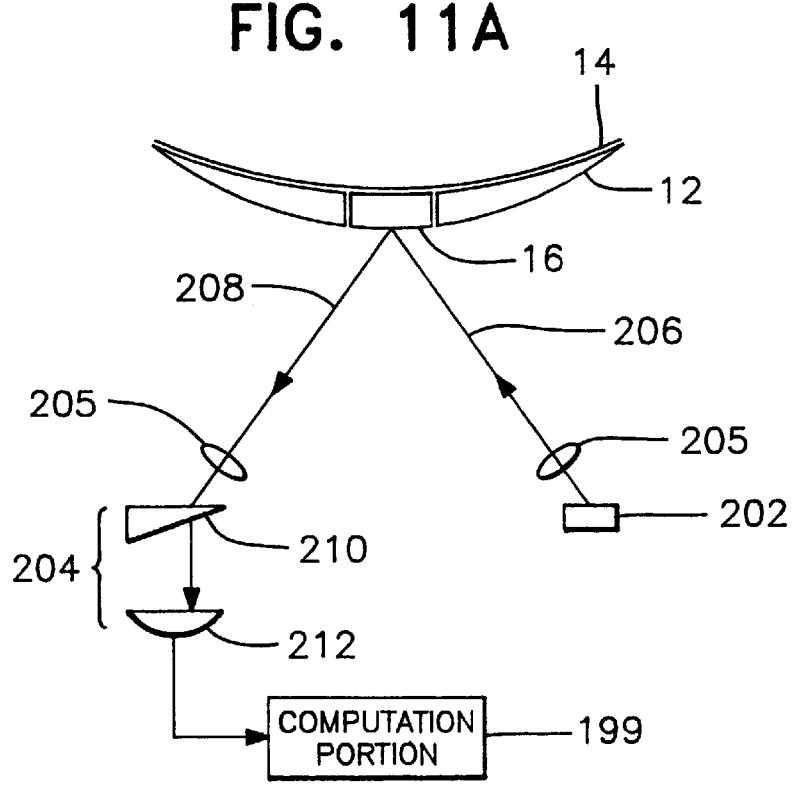
FIGS. 11A and 11B schematically illustrate an indentation distance detection arrangement in accordance with a preferred embodiment of the present invention.
Figure 11B:
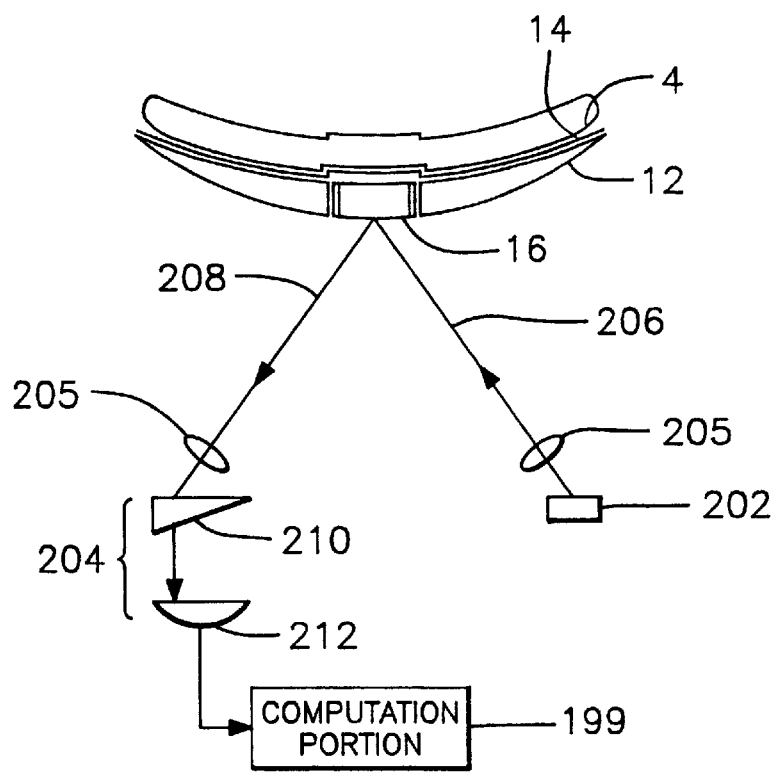

A preferred indentation distance detection arrangement 200 is illustrated in FIGS. 11A and 11B and preferably includes a beam emitter 202 and a beam sensor 204. Preferably, lenses 205 are disposed in the optical path between the beam emitter 202 and beam sensor 204. The beam emitter 202 is arranged so as to emit a beam 206 of light toward the movable central piece 16. The beam 206 of light is reflected back from the movable central piece 16 to create a reflected beam 208. The beam sensor 204 is positioned so as to receive the reflected beam 208 whenever the device 2 is located at the proper axial distance and in proper alignment with the actuation apparatus 6. Preferably, the proper distance and alignment are achieved using all or any combination of the aforementioned sighting mechanism, optical alignment mechanism and optical distance measuring mechanism.

Once proper alignment and the proper axial distance are achieved, the beam 206 strikes a first portion of the movable central piece 16, as illustrated in FIG. 11A. Upon reflection of the beam 206, the reflected beam 208 strikes a first portion of the beam sensor 204. In FIG. 11A, the first portion is located on the beam sensor 204 toward the right side of the drawing.

However, as indentation progresses, the movable central piece 16 becomes more distant from the beam emitter 202. This increase in distance is illustrated in FIG. 11A. Since the movable central piece 16 moves linearly away, the beam 206 strikes progressively more to the left on the movable central piece 16. The reflected beam 206 therefore shifts toward the left and strikes 204 at a second portion which is to the left of the first portion.

The beam sensor 204 is arranged so as to detect the shift in the reflected beam 206, which shift is proportional to the displacement of the movable central piece 16. Preferably, the beam sensor 204 includes an intensity responsive beam detector 212 which produces an output voltage proportional to the detected intensity of the reflected beam 208 and an optical filter element 210 which progressively filters more light as the light's point of incidence moves from one portion of the filter to an opposite portion.

In FIGS. 11A and 11B, the optical filter element 210 comprises a filter with a progressively increasing thickness so that light passing through a thicker portion has a more significantly reduced intensity than light passing through a thinner portion of the filter. Alternatively, the filter can have a constant thickness and progressively increasing filtering density whereby a progressively increasing filtering effect is achieved as the point of incidence moves across a longitudinal length of the filter.

When, as illustrated in FIG. 11A, the reflected beam 208 passes through a thinnest portion of the optical filter element 210 (e.g., prior to indentation), the reflected beam's intensity is reduced by only a small amount. The intensity responsive beam detector 212 therefore provides a relatively high output voltage indicating that no movement of the movable central piece 16 toward the cornea 4 has occurred.

However, as indentation progresses, the reflected beam 208 progressively shifts toward thicker portions of the optical filter element 210 which filter more light. The intensity of the reflected beam 208 therefore decreases proportionally to the displacement of the movable central piece 16 toward the cornea 4. Since the intensity responsive beam detector 212 produces an output voltage proportional to the reflected beam's intensity, this output voltage decreases progressively as the displacement of the movable central piece 16 increases. The output voltage from the intensity responsive beam detector 212 is therefore indicative of the movable central piece's displacement.

Preferably, the computation portion 199 is responsive to the current producing circuitry 32 so that, once the predetermined amount of force is applied, the output voltage from the beam detectors 212 is received by the computation portion 199. The computation portion then, based on the displacement associated with the particular output voltage, determines intraocular pressure. Preferably, the memory 33 includes a memory location for storing a value indicative of the intraocular pressure.

Also, the computation portion 199 preferably has access to an electronically or magnetically stored one of the aforementioned known tables. Since the tables indicate which intraocular pressure corresponds with certain distances traveled by the movable central piece 16, the computation portion 199 is able to determine intraocular pressure by merely determining which pressure corresponds with the distance traveled by the movable central piece 16.

The system of the present invention may also be used to calculate the rigidity of the sclera. In particular, the system is first used to determine intraocular pressure by applanation and then is used to determine intraocular pressure by indentation. The differences between the intraocular pressures detected by the two methods would then be indicative of the sclera's rigidity.

Although the foregoing description of the preferred systems generally refers to a combined system capable of detecting intraocular pressure by both applanation and indentation, it is understood that a combined system need not be created. That is, the system capable of determining intraocular pressure by applanation may be constructed independently from a separate system for determining intraocular pressure by indentation and vice versa.

MEASURING HYDRODYNAMICS OF THE EYE

The indentation device of the present invention may also be utilized to non-invasively measure hydrodynamics of an eye including outflow facility. The method of the present invention preferably comprises several steps including the following:

According to a first step, an indentation device is placed in contact with the cornea. Preferably, the indentation device comprises the contact device 2 illustrated in FIGS. 1 and 2A–2D.

Next, at least one movable portion of the indentation device is moved in toward the cornea using a first predetermined amount of force to achieve indentation of the cornea. When the indentation device is the contact device 2, the movable portion consists of the movable central piece 16.

An intraocular pressure is then determined based on a first distance traveled toward the cornea by the movable portion of the indentation device during application of the first predetermined amount of force. Preferably, the intraocular pressure is determined using the aforementioned system for determining intraocular pressure by indentation.

Next, the movable portion of the indentation device is rapidly reciprocated in toward the cornea and away from the cornea at a first predetermined frequency and using a second is predetermined amount of force during movement toward the cornea to thereby force intraocular fluid out from the eye. The second predetermined amount of force is preferably equal to or greater than the first predetermined amount of force. It is understood, however, that the second predetermined amount of force may be less than the first predetermined amount of force. The reciprocation, which preferably continues for 5 seconds, should generally not exceed 10 seconds induration.

The movable portion is then moved in toward the cornea using a third predetermined amount of force to again achieve indentation of the cornea.

A second intraocular pressure is then determined based on a second distance traveled toward the cornea by the movable portion of the indentation device during application of the third predetermined amount of force. This second intraocular pressure is also preferably determined using the aforementioned system for determining intraocular pressure by indentation. Since intraocular pressure decreases as a result of forcing intraocular fluid out of the eye during the rapid reciprocation of the movable portion, it is generally understood that, unless the eye is so defective that no fluid flows out therefrom, the second intraocular pressure will be less than the first intraocular pressure. This reduction in intraocular pressure is indicative of outflow facility.

Next, the movable portion of the indentation device is again rapidly reciprocated in toward the cornea and away from the cornea, but at a second predetermined frequency and using a fourth predetermined amount of force during movement toward the cornea. The fourth predetermined amount of force is preferably equal or greater than the second predetermined amount of force. It is understood, however, that the fourth predetermined amount of force may be less than the second predetermined amount of force. Additional intraocular fluid is thereby forced out from the eye. This reciprocation, which also preferably continues for 5 seconds, should generally not exceed 10 seconds in duration.

The movable portion is subsequently moved in toward the cornea using a fifth predetermined amount of force to again achieve indentation of the cornea.

Thereafter, a third intraocular pressure is determined based on a third distance traveled toward the cornea by the movable portion of the indentation device during application of the fifth predetermined amount of force.

The differences are then preferably calculated between the first, second, and third distances, which differences are indicative of the volume of intraocular fluid which left the eye and therefore are also indicative of the outflow facility. It is understood that the difference between the first and last distances may be used, and in this regard, it is not necessary to use the differences between all three distances. In fact, the difference between any two of the distances will suffice.

Although the relationship between the outflow facility and the detected differences varies when the various parameters of the method and the dimensions of the indentation device change, the relationship for given parameters and dimensions can be easily determined by known experimental techniques and/or using known Friedenwald Tables.

The method of the present invention is preferably carried out using an indenting surface which is three millimeters in diameter and a computer equipped with a data acquisition board. In particular, the computer generates the predetermined forces via a digital-to-analog (D/A) converter connected to the current generating circuitry 32. The computer then receives signals indicative of the first, second, and third predetermined distances via an analog-to-digital (A/D) converter. These signals are analyzed by the computer using the aforementioned relationship between the differences in distance and the outflow facility. Based on this analysis, the computer creates an output signal indicative of outflow facility. The output signal is preferably applied to a display screen which, in turn, provides a visual indication of outflow facility.

Preferably, the method further comprises the steps of plotting the differences between the first, second, and third distances to a create a graph of the differences and comparing the resulting graph of differences to that of a normal eye to determine if any irregularities in outflow facility are present. As indicated above, however, it is understood that the difference between the first and last distances may be used, and in this regard, it is not necessary to use the differences between all three distances. In fact, the difference between any two of the distances will suffice.

Preferably, the first predetermined frequency and second predetermined frequency are substantially equal and are approximately 20 Hertz. Generally, any frequencies up to 35 Hertz can be used, though frequencies below 1 Hertz are generally less desirable because the stress relaxation of the eye's outer coats would contribute to changes in pressure and volume.

The fourth predetermined amount of force is preferably at least twice the second predetermined amount of force, and the third predetermined amount of force is preferably approximately half of the first predetermined amount of force. It is understood, however, that other relationships will suffice and that the present method is not limited to the foregoing preferred relationships.

According to a preferred use of the method, the first predetermined amount of force is between 0.01 Newton and 0.015 Newton; the second predetermined amount of force is between 0.005 Newton and 0.0075 Newton the third predetermined amount of force is between 0.005 Newton and 0.0075 Newton; the fourth predetermined amount of force is between 0.0075 Newton and 0.0125 Newton; the fifth predetermined amount of force is between 0.0125 Newton and 0.025 Newton; the first predetermined frequency is between 1 Hertz and 35 Hertz; and the second predetermined frequency is also between 1 Hertz and 35 Hertz. The present method, however, is not limited to the foregoing preferred ranges.

Although the method of the present invention is preferably carried out using the aforementioned device, it is understood that various other tonometers may be used. The method of the present invention therefore is not limited in scope to its use in conjunction with the claimed system and illustrated contact device.

ALTERNATIVE EMBODIMENTS OF THE CONTACT DEVICE

Although the foregoing description utilizes an embodiment of the contact device 2 which includes a flexible membrane 14 on the inside surface of the contact device 2, it is readily understood that the present invention is not limited to such an arrangement. Indeed, there are many variations of the contact device which fall well within the scope of the present invention.

The contact device 2, for example, may be manufactured with no flexible membrane, with the flexible membrane on the outside surface of the contact device 2 (i.e., the side away from the cornea), with the flexible membrane on the inside surface of the contact device 2, or with the flexible membrane on both sides of the contact device 2.

Also, the flexible membrane (s) 14 can be made to have an annular shape, thus permitting light to pass undistorted directly to the movable central piece 16 and the cornea for reflection thereby.

Figure 12:
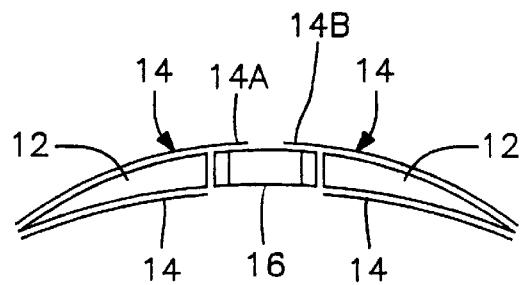
FIG. 12 is a cross-sectional view of an alternative contact device in accordance with another preferred embodiment of the present invention.

In addition, as illustrated in FIG. 12, the movable central piece 16 may be formed with a similar annular shape so that a transparent central portion thereof merely contains air. This way, light passing through the entire contact device 2 impinges directly on the cornea without undergoing any distortion due to the contact device 2.

Alternatively, the transparent central portion can be filled with a transparent solid material. Examples of such transparent solid materials include polymethyl methacrylate, glass, hard acrylic, plastic polymers, and the like. According to a preferred arrangement, glass having an index of refraction substantially greater than that of the cornea is utilized to enhance reflection of light by the cornea when the light passes through the contact device 2. Preferably, the index of refraction for the glass is greater than 1.7, compared to the typical index of refraction of 1.37 associated with the cornea.

It is understood that the outer surface of the movable central piece 16 may be coated with an anti-reflection layer in order to eliminate extraneous reflections from that surface which might otherwise interfere with operation of the alignment mechanism and the applanation detecting arrangement.

The interconnections of the various components of the contact device 2 are also subject to modification without departing from the scope and spirit of the present invention. It is understood therefore that many ways exist for interconnecting or otherwise maintaining the working relationship between the movable central piece 16, the rigid annular member 12, and the membranes 14.

When one or two flexible membranes 14 are used, for example, the substantially rigid annular member 12 can be attached to any one or both of the flexible membrane(s) 14 using any known attachment techniques, such as gluing, heat-bonding, and the like. Alternatively, when two flexible membranes 14 are used, the components may be interconnected or otherwise maintained in a working relationship, without having to directly attach the flexible membrane 14 to the substantially rigid annular member 12. Instead, the substantially rigid annular member 12 may be retained between the two flexible membranes 14 by bonding the membranes to one another about their peripheries while the rigid annular member 12 is sandwiched between the membranes 14.

Although the movable central piece 16 may be attached to the flexible membrane(s) 14 by gluing, heat-bonding, and the like, it is understood that such attachment is not necessary. Instead, one or both of the flexible membranes 14 can be arranged so as to completely or partially block the movable central piece 16 and prevent it from falling out of the hole in the substantially rigid annular member 12. When the aforementioned annular version of the flexible membranes 14 is used, as illustrated by way of example in FIG. 12, the diameter of the hole in at least one of the annular flexible membranes 14 is preferably smaller than that of the hole in the substantially rigid annular member 12 so that a radially inner portion 14A of the annular flexible membrane 14 overlaps with the movable central piece 16 and thereby prevents the movable central piece 16 from falling out of the hole in the substantially rigid annular member 21.

Figure 13A:
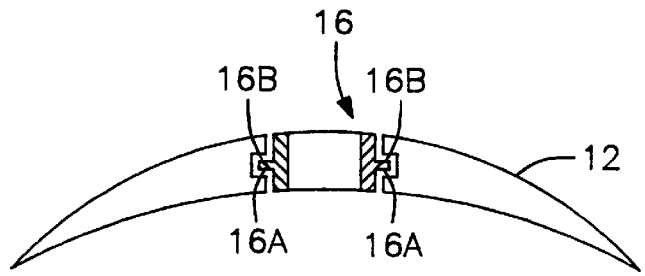
FIG. 13A is a cross-sectional view of an alternative contact device.

As illustrated in FIG. 13A, another way of keeping the movable central piece 16 from failing out of the hole in the substantially rigid annular member 12 is to provide arms 16A which extend radially out from the movable central piece 16 and are slidably received in respective grooves 16B. The grooves 16B are formed in the rigid annular member 12. Each groove 16B has a longitudinal dimension (vertical in FIG. 13) which is selectively chosen to restrict the range of movement of the movable central piece 16 to within predetermined limits. Although FIG. 13 shows an embodiment wherein the grooves are in the substantially rigid annular member 12 and the arms extend out from the movable central piece 16, it is understood that an equally effective arrangement can be created by reversing the configuration such that the grooves are located in the movable central piece 16 and the arms extend radially in from the substantially rigid annular member 12.

Preferably, the grooves 16B include resilient elements, such as miniature springs, which bias the position of the movable central piece 16 toward a desired starting position. In addition, the arms 16A may include distally located miniature wheels which significantly reduce the friction between the arms 16A and the walls of the grooves 16B.

Figure 13B:
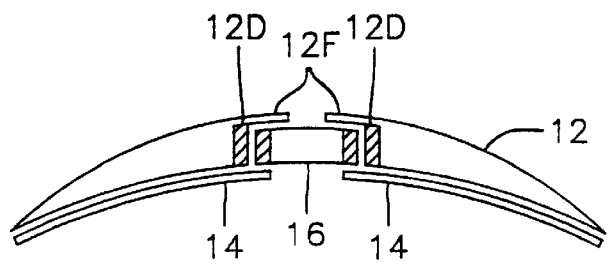
FIG. 13B is a cross-sectional view of an alternative contact device.

FIG. 13B illustrates another way of keeping the movable central piece 16 from falling out of the hole in the substantially rigid annular member 12. In FIG. 13B, the substantially rigid annular member 12 is provided with radially inwardly extending flaps 12F at the outer surface of the annular member 12. One of the aforementioned annular membranes 14 is preferably disposed on the inner side of the substantially rigid annular member 12. Preferably, a portion of the membrane 14 extends radially inwardly past the walls of the rigid annular member's hole. The combination of the annular membrane 14 and the flaps 12F keeps the movable central piece 16 from falling out of the hole in the substantially rigid annular member 12.

The flaps 12F may also be used to achieve or facilitate actuation of the movable central piece 16. In a magnetically actuated embodiment, for example, the flaps 12F may be magnetized so that the flaps 12F move inwardly in response to an externally applied magnetic field.

Figure 14:
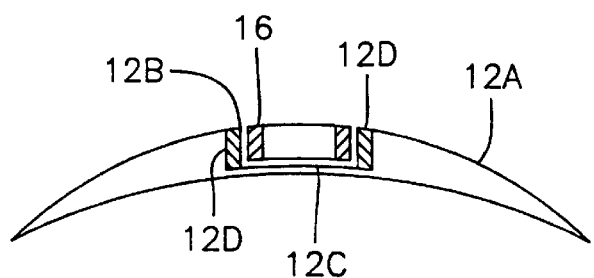
FIG. 14 is a cross-sectional view of an alternative contact device.

With reference to FIG. 14, an alternative embodiment of the contact device 2 is made using a soft contact lens material 12A having a progressively decreasing thickness toward its outer circumference. A cylindrical hole 12B is formed in the soft contact lens material 12A. The hole 12B, however, does not extend entirely through the soft contact lens material 12A. Instead, the hole has a closed bottom defined by a thin portion 12C of the soft contact lens material 12A. The movable central piece 16 is disposed slidably within the hole 12B, and preferably, the thin portion 12C is no more than 0.2 millimeters thick, thereby allowing the movable central piece 16 to achieve applanation or indentation when moved against the closed bottom of the hole toward the cornea with very little interference from the thin portion 12C.

Preferably, a substantially rigid annular member 12D is inserted and secured to the soft contact material 12A to define a more stable wall structure circumferentially around the hole 12B. This, in turn, provides more stability when the movable central piece 16 moves in the hole 12B.

Although the soft lens material 12A preferably comprises Hydrogel, silicone, flexible acrylic, or the like, it is understood that any other suitable materials may be used. In addition, as indicated above, any combination of flexible membranes may be added to the embodiment of FIG. 14. Although the movable central piece 16 in FIG. 14 is illustrated as being annular, it is understood that any other shape may be utilized. For example, any of the previously described movable central pieces 16 would suffice.

Similarly, the annular version of the movable central piece 16 may be modified by adding a transparent bottom plate (not illustrated) which defines a flat transparent bottom surface of the movable central piece 16. When modified in this manner, the movable central piece 16 would have a generally cup-shaped appearance. Preferably, the flat transparent bottom surface is positioned toward the cornea to enhance the flattening effect of the movable central piece 16; however, it is understood that the transparent plate can be located on the outside surface of the movable central piece 16 if desired.

Although the movable central piece 16 and the hole in the substantially rigid annular member 12 (or the hole in the soft contact lens material 12A) are illustrated as having complementary cylindrical shapes, it is understood that the complementary shapes are not limited to a cylinder, but rather can include any shape which permits sliding of the movable central piece 16 with respect to its surrounding structure.

It is also understood that the movable central piece 16 may be mounted directly onto the surface of a flexible membrane 14 without using a substantially rigid annular member 12. Although such an arrangement defines a working embodiment of the contact device 2, its stability, accuracy, and level of comfort are significantly reduced compared to that of a similar embodiment utilizing the substantially rigid annular member 12 with a progressively tapering periphery.

Although the illustrated embodiments of the movable central piece 16 include generally flat outside surfaces with well defined lateral edges, it is understood that the present invention is not limited to such arrangements. The present invention, for example, can include a movable central piece 16 with a rounded outer surface to enhance comfort and/or to coincide with the curvature of the outer surface of the substantially rigid annular member 12. The movable central piece can also be made to have any combination of curved and flat surfaces defined at its inner and outer surfaces, the inner surface being the surface at the cornea and the outer surface being the surface directed generally away from the cornea.

Figure 15:
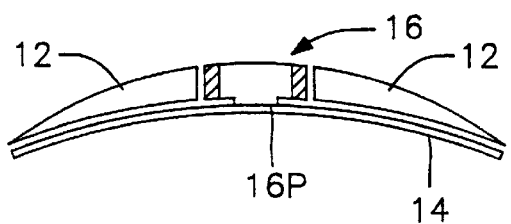
FIG. 15 is a cross-sectional view of an alternative contact device.

With reference to FIG. 15, the movable central piece 16 may also include a centrally disposed projection 16P directed toward the cornea. The projection 16P is preferably created by extending the transparent solid material in toward the cornea at the center of the movable central piece 16.

ALTERNATIVE EMBODIMENT FOR MEASURING INTRAOCULAR PRESSURE BY APPLANATION

Figure 16:
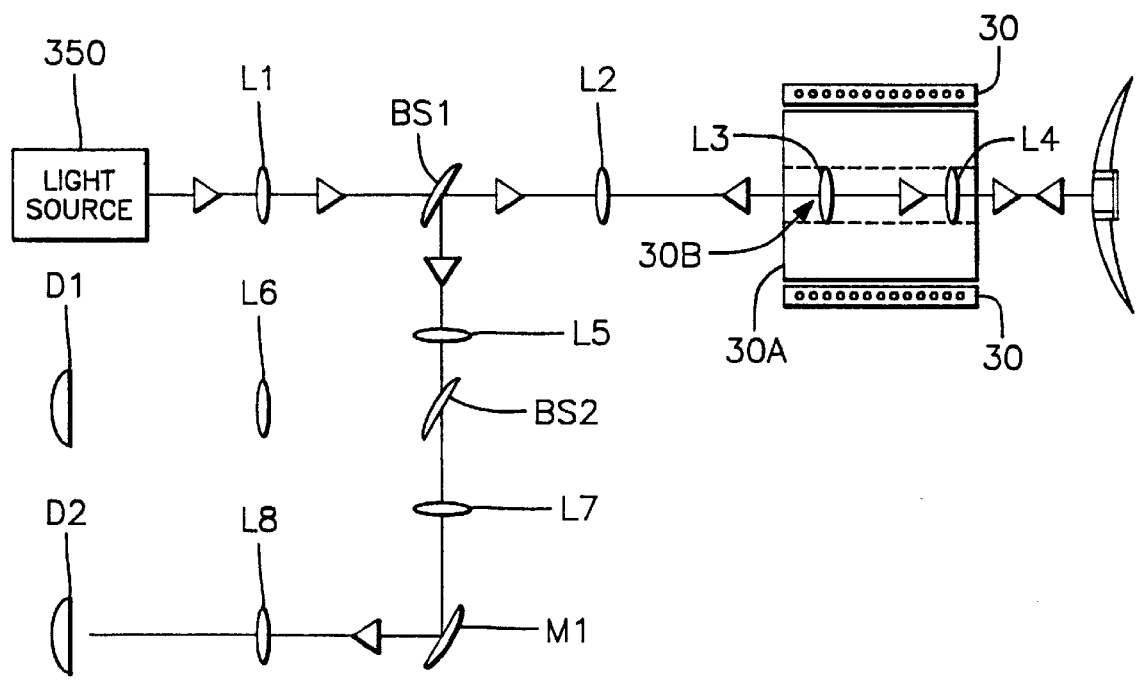
FIG. 16 schematically illustrates an alternative embodiment of the system for measuring intraocular pressure by applanation, according to the present invention.

With reference to FIG. 16, an alternative embodiment of the system for measuring intraocular pressure by applanation will now be described. The alternative embodiment preferably utilizes the version of the contact device 2 which includes a transparent central portion.

According to the alternative embodiment, the schematically illustrated coil 30 of the actuation apparatus includes an iron core 30A for enhancing the magnetic field produced by the coil 30. The iron core 30A preferably has an axially extending bore hole 30B (approximately 6 millimeters in diameter) which permits the passage of light through the iron core 30A and also permits mounting of two lenses L3 and L4 therein.

In order for the system to operate successfully, the strength of the magnetic force applied by the coil 30 on the movable central piece 16 should be sufficient to applanate patients' corneas over at least the full range of intraocular pressures encountered clinically (i.e. 5–50 mm Hg). According to the illustrated alternative embodiment, intraocular pressures ranging from 1 to over 100 mm of mercury can be evaluated using the present invention. The forces necessary to applanate against such intraocular pressures may be obtained with reasonably straightforward designs and inexpensive materials as will be demonstrated by the following calculations:

It is known that the force F exerted by an external magnetic field on a small magnet equals the magnet's magnetic dipole moment m multiplied by the gradient of the external field's magnetic induction vector "grad B" acting in the direction of the magnet's dipole moment.

$$F = m * \text{grad } B \quad (1)$$

The magnetic dipole moment m for the magnetic version of the movable central piece 16 can be determined using the following formula:

$$m = (B*V)/u_0 \quad (2)$$

where B is the magnetic induction vector just at the surface of one of the poles of the movable central piece 16, V is its volume, and $u_0$ is the magnetic permeability of free space which has a value of $12.57 * 10^{-7}$ Henry/meter.

A typical value of B for magnetized Alnico movable central pieces 16 is 0.5 Tesla. If the movable central piece 16 has a thickness of 1 mm, a diameter of 5 mm, and 50% of its initial volume is machined away, its volume V=9.8 cubic millimeters ($9.8 * 10^{-9}$ cubic meters. Substituting these values into Equation 2 yields the value for the movable central piece's magnetic dipole moment, namely, m=0.00390 Amp* (Meter)$^2$.

Using the foregoing calculations, the specifications of the actuation apparatus can be determined. The magnetic field gradient "grad B" is a function of the distance x measured from the front face of the actuation apparatus and may be calculated as follows:

$$\text{grad } B = \frac{u_0 * X * N * I * (RAD)^2 * \{[(x+L)^2 + RAD^2]^{-3/2} - [x^2 + RAD^2]^{-3/2}\}}{2*L} \quad (3)$$

where X is the magnetic susceptibility of the iron core, N is the number of turns in the coil's wire, I is the electric current carried by the wire, L is the length of the coil 30, and RAD is the radius of the coil 30.

The preferred values for these parameters in the alternative embodiment are: X=500, N=200, I=1.0 Amp, L=0.05 meters, and RAD=0.025 meters. It is understood, however, that the present invention is not limited to these preferred parameters. As usual, $u_0 = 12.57 * 10^{-7}$ Henry/meter.

The force F exerted by the magnetic actuation apparatus on the movable central piece 16 is found from Equation 1 using the aforementioned preferred values as parameters in Equation 3, and the above result for m=0.00390 Amp* (Meter)2. A plot of F as a function of the distance x separating the movable central piece 16 from the pole of the magnetic actuation apparatus appears as FIG. 16A.

Figure 16A:
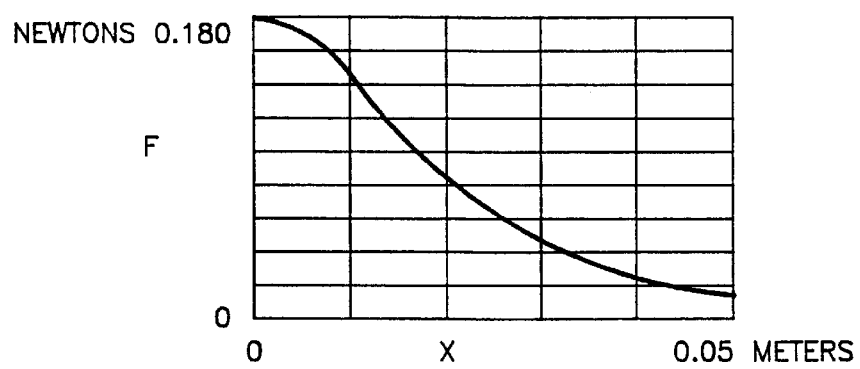
FIG. 16A is a graph depicting force (F) as a function of the distance (x) separating a movable central piece from the pole of a magnetic actuation apparatus in accordance with the present invention.

Since a patient's cornea 4, when covered by the contact device 2 which holds the movable central piece 16, can be placed conveniently at a distance x32 2.5 cm (0.025 m) from the actuation apparatus, it is noted from FIG. 16A that the magnetic actuation force is approximately F=0.063 Newtons.

This force is then compared to $F_{required}$ which is the force actually needed to applanate a cornea 4 over a typical applanation area when the intraocular pressure is as high as 50 mm Hg. In Goldman tonometry, the diameter of the applanated area is approximately 3.1 mm and therefore the typical applanated AREA will equal 7.55 mm$^2$. The typical maximum pressure of 50 mm Hg can be converted to metric form, yielding a pressure of 0.00666 Newtons/mm$^2$. The value of $F_{required}$ then can be determined using the following equation:

$$F_{required} = \text{PRESSURE} * \text{AREA} \quad (4)$$

After mathematical substitution, $F_{required}$=0.050 Newtons. Comparing the calculated magnetic actuation force F to the force required $F_{required}$, it becomes clear that $F_{required}$ is less than the available magnetic driving force F. Therefore, the maximum force needed to applanate the cornea 4 for intraocular pressure determinations is easily achieved using the actuation apparatus and movable central piece 16 of the present invention.

It is understood that, if a greater force becomes necessary for whatever reason (e.g, to provide more distance between the contact device 2 and the actuation apparatus), the various parameters can be manipulated and/or the current in the coil 30 can be increased to achieve a satisfactory arrangement.

In order for the actuation apparatus to properly actuate the movable central piece 16 in a practical way, the magnetic actuation force (and the associated magnetic field) should increase from zero, reach a maximum in about 0.01 sec., and then return back to zero in approximately another 0.01 sec. The power supply to the actuation apparatus therefore preferably includes circuitry and a power source capable of driving a "current pulse" of peak magnitude in the 1 ampere range through a fairly large inductor (i.e. the coil 30).

For "single-pulse" operation, a DC-voltage power supply can be used to charge a capacitor C through a charging resistor. One side of the capacitor is grounded while the other side ("high" side) may be at a 50 volt DC potential. The "high" side of the capacitor can be connected via a high current-carrying switch to a "discharge circuit" consisting of the coil 30 and a damping resistor R This arrangement yields an R-L-C series circuit similar to that which is conventionally used to generate large pulses of electrical current for such applications as obtaining large pulsed magnetic fields and operating pulsed laser power systems. By appropriately choosing the values of the electrical components and the initial voltage of the capacitor, a "current pulse" of the kind described above can be generated and supplied to the coil 30 to thereby operate the actuation apparatus.

It is understood, however, that the mere application of a current pulse of the kind described above to a large inductor, such as the coil 30, will not necessarily yield a zero magnetic field after the current pulse has ended. Instead, there is usually an undesirable residual magnetic field from the iron-core 30A even though no current is flowing in the coil 30. This residual field is caused by magnetic hysteresis and would tend to produce a magnetic force on the movable central piece 16 when such a force is not wanted.

Therefore, the alternative embodiment preferably includes means for zeroing the magnetic field outside the actuation apparatus after operation thereof Such zeroing can be provided by a demagnetizing circuit connected to the iron-core 30A.

Methods for demagnetizing an iron-core are generally known and are easy to implement. It can be done, for example, by reversing the current in the coil repeatedly while decreasing its magnitude. The easiest way to do this is by using a step-down transformer where the input is a sinusoidal voltage at 60 Hz which starts at a "line voltage" of 110 VAC and is gradually dampened to zero volts, and where the output of the transformer is connected to the coil 30.

The actuation apparatus therefore may include two power circuits, namely, a "single pulse" current source used for conducting applanation measurements and a "demagnetization circuit" for zeroing the magnetic field of the coil 30 immediately after each applanation measurement.

Figure 17:
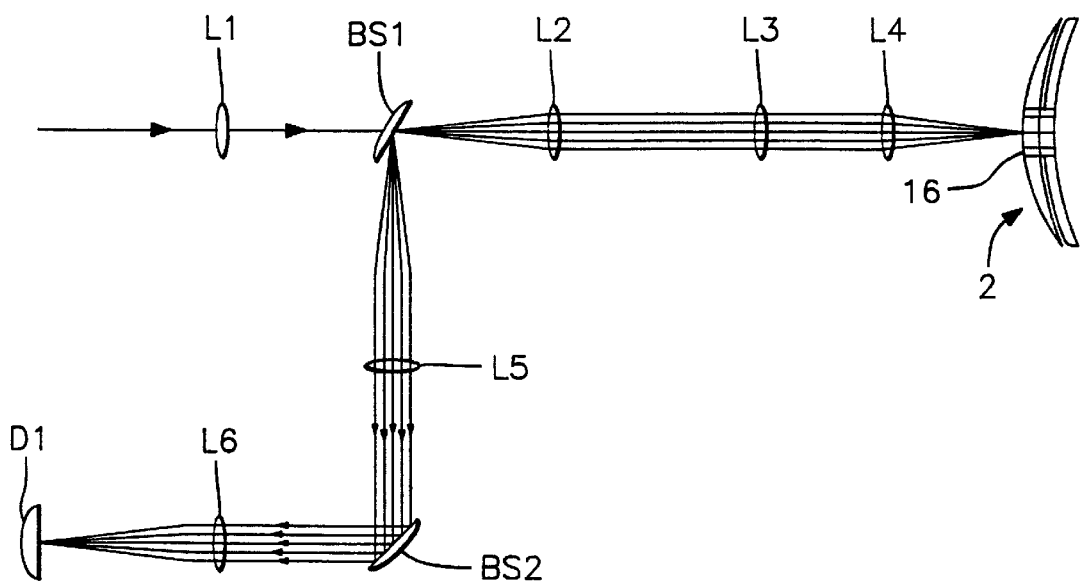
FIG. 17 schematically illustrates an alternative optical alignment system in accordance with the present invention.

As illustrated in FIGS. 16 and more specifically in FIG. 17, the alternative embodiment used for applanation also includes an alternative optical alignment system. Alignment is very important because, as indicated by the graph of FIG. 16A, the force exerted by the actuation apparatus on the movable central piece 16 depends very much on their relative positions. In addition to the movable central piece's axial location with respect to the actuation apparatus (x-direction), the magnetic force exerted on the movable central piece 16 also depends on its lateral (y-direction) and vertical (z-direction) positions, as well as on its orientation (tip and tilt) with respect to the central axis of the actuation apparatus.

Considering the variation of force F with axial distance x shown in FIG. 16A, it is clear that the movable central piece 16 should be positioned in the x-direction with an accuracy of about +/−1 mm for reliable measurements. Similarly, since the diameter of the coil 30 is preferably 50 mm, the location of the movable central piece 16 with respect to the y and z directions (i.e. perpendicular to the longitudinal axis of the coil 30) should be maintained to within +/−2 mm (a region where the magnetic field is fairly constant) of the coil's longitudinal axis.

Finally, since the force on the movable central piece 16 depends on the cosine of the angle between the coil's longitudinal axis and the tip or tilt angle of the movable central piece 16, it is important that the range of the patient's gaze with respect to the coil's longitudinal axis be maintained within about +/−2 degrees for reliable measurements.

In order to satisfy the foregoing criteria, the alternative optical alignment system facilitates precise alignment of the patient's corneal vertex (situated centrally behind the movable central piece 16) with the coil's longitudinal axis, which precise alignment can be achieved independently by a patient without the assistance of a trained medical technician or health care professional.

The alternative optical alignment system functions according to how light reflects and refracts at the corneal surface. For the sake of simplicity, the following description of the alternative optical alignment system and FIGS. 16 and 17 does not refer specifically to the effects of the movable central piece's transparent central portion on the operation of the optical system, primarily because the transparent central portion of the movable central piece 16 is preferably arranged so as not to affect the behavior of optical rays passing through the movable central piece 16.

Also, for the sake of simplicity, FIG. 17 does not show the iron core 30A and its associated bore 30B, though it is understood that the alignment beam (described hereinafter) passes through the bored hole 30B and that the lenses L3 and L4 are mounted within the bored hole 30B.

As illustrated in FIG. 16, a point-like source 350 of light such as an LED is located at the focal plane of a positive (i.e., convergent) lens L1. The positive lens L1 is arranged so as to collimate a beam of light from the source 350. The collimated beam passes through a beam splitter BS1 and a transmitted beam of the collimated beam continues through the beam splitter BS1 to a positive lens L2. The positive lens L2 focuses the transmitted beam to a point within lens L3 located at the focal plane of a lens L4. The light rays passing through L4 are collimated once again and enter the patient's eye where they are focused on the retina 5. The transmitted beam is therefore perceived by the patient as a point-like light.

Figure 18:
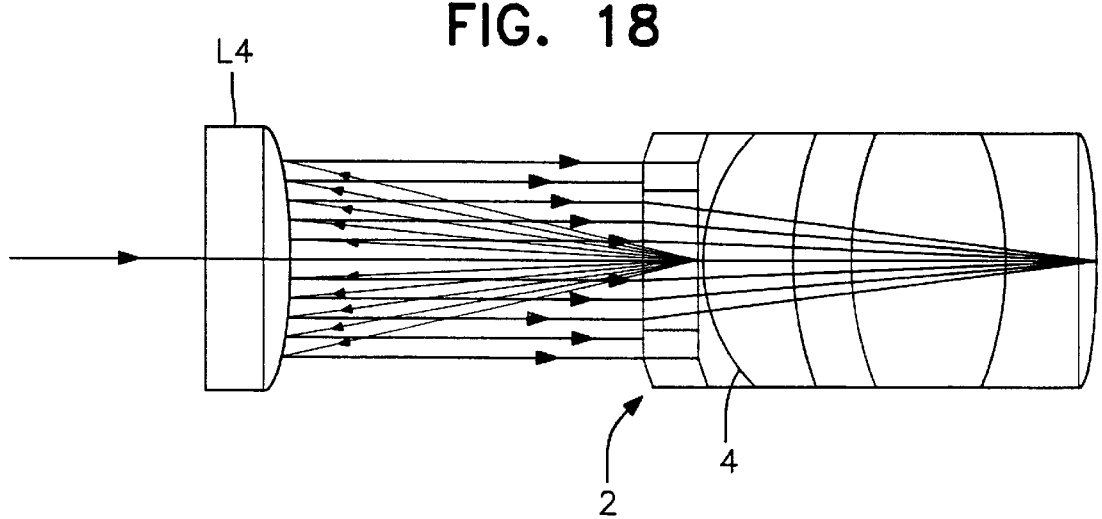
FIGS. 18 and 19 schematically illustrate arrangements for guiding the patient during alignment of his/her eye in the apparatus of the present invention.

Some of the rays which reach the eye are reflected from the corneal surface in a divergent manner due to the cornea's preapplanation curvature, as shown in FIG. 18, and are returned back to the patient's eye by a partially mirrored planar surface of the lens L4. These rays are perceived by the patient as an image of the corneal reflection which guides the patient during alignment of his/her eye in the instrument as will be described hereinafter.

Those rays which are reflected by the convex cornea 4 and pass from right-to-left through the lens L4 are made somewhat more convergent by the lens L4. From the perspective of lens L3, these rays appear to come from a virtual point object located at the focal point. Therefore, after passing through L3, the rays are once again collimated and enter the lens L2 which focuses the rays to a point on the surface of the beam splitter BS1. The beam splitter BS1 is tilted at 45 degrees and consequently deflects the rays toward a lens L5 which, in turn, collimates the rays. These rays then strike the surface of a tilted reflecting beam splitter BS2. The collimated rays reflected from the beam splitter BS2 enter lens L6 which focuses them onto the small aperture of a silicon photodiode which functions as an alignment sensor D1.

Therefore, when the curved cornea 4 is properly aligned, an electric current is produced by the alignment sensor D1. The alignment system is very sensitive because it is a confocal arrangement (i.e., the point image of the alignment light due to the corneal reflection—Purkinje image—in its fiducial position is conjugate to the small light-sensitive aperture of the silicon photodiode). In this manner, an electrical current is obtained from the alignment sensor only when the cornea 4 is properly aligned with respect to the lens L4 which, in turn, is preferably mounted at the end of the magnetic actuation apparatus. The focal lengths of all the lenses shown in FIG. 17 are preferably 50 mm except for the lens L3 which preferably has a focal length of 100 MM.

An electrical circuit capable of operating the alignment sensor D1 is straight-forward to design and build. The silicon photodiode operates without any bias voltage ("photovoltaic mode") thus minimizing inherent detector noise. In this mode, a voltage signal, which corresponds to the light level on the silicon surface, appears across a small resistor spanning the diode's terminals. Ordinarily this voltage signal is too small for display or subsequent processing; however, it can be amplified many orders of magnitude using a simple transimpedance amplifier circuit. Preferably, the alignment sensor D1 is utilized in conjunction with such an amplified photodiode circuit.

Preferably, the circuitry connected to the alignment sensor D1 is arranged so as to automatically activate the actuation apparatus immediately upon detecting via the sensor D1 the existence of proper alignment. If, however, the output from the alignment sensor D1 indicates that the eye is not properly aligned, the circuitry preferably prevents activation of the actuation apparatus. In this way, the alignment sensor D1, not the patient, determines when the actuation apparatus will be operated.

As indicated above, the optical alignment system preferably includes an arrangement for guiding the patient during alignment of his/her eye in the instrument. Such arrangements are illustrated, by way of example, in FIGS. 18 and 19.

The arrangement illustrated in FIG. 18 allows a patient to precisely position his/her eye translationally in all x-y-z directions. In particular, the lens L4 is made to include a piano surface, the plano surface being made partially reflective so that a patient is able to see a magnified image of his/her pupil with a bright point source of light located somewhere near the center of the iris. This point source image is due to the reflection of the incoming alignment beam from the curved corneal surface (called the first Purkinje image) and its subsequent reflection from the mirrored or partially reflecting piano surface of the lens L4. Preferably, the lens L4 makes the reflected rays parallel as they return to the eye which focuses them onto the retina 5.

Although FIG. 18 shows the eye well aligned so that the rays are focused at a central location on the surface of the retina 5, it is understood that movements of the eye toward or away (x-direction) from the lens L4 will blur the image of the corneal reflection, and that movements of the eye in either the y or z direction will tend to displace the corneal reflection image either to the right/left or up/down.

The patient therefore performs an alignment operation by gazing directly at the alignment light and moving his/her eye slowly in three dimensions until the point image of the corneal reflection is as sharp as possible (x-positioning) and merges with the point image of the alignment light (y & z positioning) which passes straight through the cornea 4.

Figure 19:
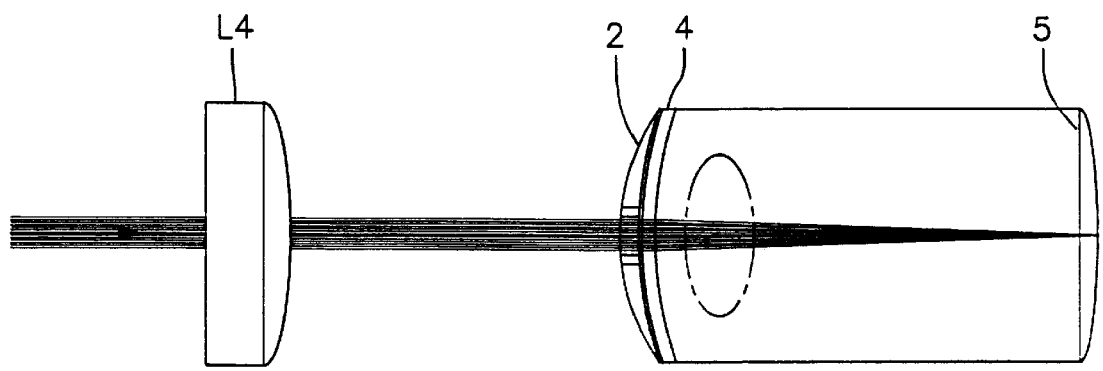

As illustrated in FIG. 19, the lens L4 need not have a partially reflective portion if the act of merely establishing a proper direction of gaze provides sufficient alignment.

Once alignment is achieved, a logic signal from the optical alignment system activates the "pulse circuit" which, in turn, powers the actuation apparatus. After the actuation apparatus is activated, the magnetic field at the patient's cornea increases steadily for a time period of about 0.01 sec. The effect of this increasing field is to apply a steadily increasing force to the movable central piece 16 resting on the cornea which, in turn, causes the cornea 4 to flatten increasingly over time. Since the size of the applanation area is proportional to the force on the movable central piece 16 (and Pressure=Force/Area), the intraocular pressure (IOP) is found by determining the ratio of the force to the area applanated by the force.

In order to detect the applanated area and provide an electrical signal indicative of the size of the applanated area, the alternative embodiment includes an applanation sensor D2. The rays that are reflected from the applanated corneal surface are reflected in a generally parallel manner by virtue of the flat surface presented by the applanated cornea 4. As the rays pass from right-to-left through the lens L4, they are focused within the lens L3 which, in turn, is in the focal plane of the lens L2. Consequently, after passing through the lens L2, the rays are once again collimated and impinge on the surface of beam splitter BS1. Since the beam splitter BS1 is tilted at 45 degrees, the beam splitter BS1 deflects these collimated rays toward the lens L5 which focuses the rays to a point at the center of beam splitter BS2. The beam splitter BS2 has a small transparent portion or hole in its center which allows the direct passage of the rays on to the lens L7 (focal length of preferably 50 mm). The lens L7 pertains to an applanation sensing arm of the alternative embodiment.

The focal spot on the beam splitter BS2 is in the focal plane of the lens L7. Consequently, the rays emerging from the lens L7 are once again collimated. These collimated rays impinge on the mirror M1, preferably at a 45 degree angle, and are deflected toward a positive lens L8 (focal length of 50 mm) which focuses the rays onto the small aperture of a silicon photodiode which defines the applanation sensor D2.

It is understood that rays which impinge upon the cornea 4 slightly off center tend to be reflected away from the lens L4 when the cornea's curvature remains undisturbed. However, as applanation progresses and the cornea becomes increasingly flat, more of these rays are reflected back into the lens L4. The intensity of light on the applanation sensor D2 therefore increases, and as a result, an electric current is generated by the applanation sensor D2, which electric current is proportional to the degree of applanation.

Preferably, the electrical circuit utilized by the applanation sensor D2 is identical or similar to that used by the alignment sensor D1

The electric signal indicative of the area of applanation can then be combined with signals indicative of the time it takes to achieve such applanation and/or the amount of current (which, in turn, corresponds to the applied force) used to achieve the applanation, and this combination of information can be used to determine the intraocular pressure using the equation Pressure=Force/Area.

The following are preferred operational steps for the actuation apparatus during a measurement cycle:

1) While the actuation apparatus is OFF, there is no magnetic field being directed toward the contact device 2.

2) When the actuation apparatus is turned ON, the magnetic field initially remains at zero.

3) Once the patient is in position, the patient starts to align his/her eye with the actuation apparatus. Until the eye is properly aligned, the magnetic field remains zero.

4) When the eye is properly aligned (as automatically sensed by the optical alignment Sensor), the magnetic field (driven by a steadily increasing electric current) starts to increase from zero.

5) During the time period of the current increase (approximately 0.01 sec.), the force on the movable central piece also increases steadily.

6) In response to the increasing force on the movable central piece, the surface area of the cornea adjacent to the movable central piece is increasingly flattened.

7) Light from the flattened surface area of the cornea is reflected toward the detecting arrangement which detects when a predetermined amount of applanation has been achieved. Since the amount of light reflected straight back from the cornea is proportional to the size of the flattened surface area, it is possible to determine exactly when the predetermined amount of applanation has been achieved, preferably a circular area of diameter 3.1 mm, of the cornea. It is understood, however, that any diameter ranging from 0.10 mm to 10 mm can be utilized.

8) The time required to achieve applanation of the particular surface area (i.e, the predetermined amount of applanation) is detected by a timing circuit which is part of the applanation detecting arrangement. Based on prior calibration and a resulting conversion table, this time is converted to an indication of intraocular pressure. The longer the time required to applanate a specific area, the higher the intraocular pressure, and vice versa.

9) After the predetermined amount of applanation is achieved, the magnetic field is turned OFF.

10) The intraocular pressure is then displayed by a readout meter, and all circuits are preferably turned completely OFF for a period of 15 seconds so that the automatic measurement cycle will not be immediately repeated if the patient's eye remains aligned. It is understood, however, that the circuits may remain ON and that a continuous measurement of intraocular pressure may be achieved by creating an automatic measurement cycle. The data provided by this automatic measurement cycle then may be used to calculate blood flow.

11) If the main power supply has not been turned OFF, all circuits are turned back ON after 15 seconds and thus become ready for the next measurement.

Although there are several methods for calibrating the various elements of the system for measuring intraocular pressure by applanation, the following are illustrative examples of how such calibration can be achieved:

Initially, after manufacturing the various components, each component is tested to ensure the component operates properly. This preferably includes verifying that there is free piston-like movement (no twisting) of the movable central piece in the contact device; verifying the structural integrity of the contact device during routine handling; evaluating the magnetic field at the surface of the movable central piece in order to determine its magnetic dipole moment (when magnetic actuation is utilized); verifying that the electrical current pulse which creates the magnetic field that actuates the magnetically responsive element of the movable central piece, has an appropriate peak magnitude and duration, and ensuring that there is no "ringing"; verifying the efficacy of the "demagnetization circuit" at removing any residual magnetization in the iron-core of the actuation apparatus after it has been pulsed; measuring the magnetic field as a function of time along and near the longitudinal axis of the coil where the movable central piece will eventually be placed; determining and plotting grad B as a function of time at several x-locations (i.e., at several distances from the coil); and positioning the magnetic central piece (contact device) at several x-locations along the coil's longitudinal axis and determining the force F acting on it as a function of time during pulsed-operation of the actuation apparatus.

Next, the optical alignment system is tested for proper operation. When the optical alignment system comprises the arrangement illustrated in FIGS. 16 and 17, for example, the following testing and calibration procedure may be used:

a) First, a convex glass surface (one face of a lens) having a radius of curvature approximately the same as that of the cornea is used to simulate the cornea and its surface reflection. Preferably, this glass surface is placed in a micrometer-adjusted mounting arrangement along the longitudinal axis of the coil. The micrometer-adjusted mounting arrangement permits rotation about two axes (tip & tilt) and translation in three-dimensional x-y-z space.

b) With the detector D1 connected to a voltage or current meter, the convex glass surface located at its design distance of 25 mm from lens L4 will be perfectly aligned (tip/tilt/x/y/z) by maximizing the output signal at the read-out meter.

c) After perfect alignment is achieved, the alignment detection arrangement is "detuned" for each of the positional degrees of freedom (tip/tilt/x/y/z) and curves are plotted for each degree of freedom to thereby define the system's sensitivity to alignment.

d) The sensitivity to alignment will be compared to the desired tolerances in the reproducibility of measurements and also can be based on the variance of the magnetic force on the movable central piece as a function of position.

e) Thereafter, the sensitivity of the alignment system can be changed as needed by such procedures as changing the size of the aperture in the silicon photodiode which functions as the alignment sensor D1. and/or changing an aperture stop at lens L4.

Next, the detection arrangement is tested for proper operation. When the detection arrangement comprises the optical detection arrangement illustrated in FIG. 16, for example, the following testing and calibration procedure may be used:

a) A flat glass surface (e.g., one face of a short polished rod) with a diameter of preferably 4–5 mm is used to simulate the applanated cornea and its surface reflection.

b) A black, opaque aperture defining mechanism (which defines clear inner apertures with diameters ranging from 0.5 to 4 mm and which has an outer diameter the same as that of the rod) is arranged so as to partially cover the face of the rod, thus simulating various stages of applanation.

c) The flat surfaced rod is placed in a mount along the longitudinal axis of the coil in a micrometer-adjusted mounting arrangement that can rotate about two axes (tip & tilt) and translate in three-dimensional x-y-z space.

d) The applanation sensor D2 is then connected to a voltage or current meter, while the rod remains located at its design distance of 25 mm from the lens L4 where it is perfectly aligned (tip/tilt/x/y/z) by maximizing the output signal from the applanation sensor D2. Alignment, in this case, is not sensitive to x-axis positioning.

e) After perfect alignment is achieved, the alignment is "detuned" for each of the positional degrees of freedom (tip/tilt/x/y/z) and curves are plotted for each degree of freedom thus defining the system's sensitivity to alignment. Data of this kind is obtained for the variously sized apertures (i.e. different degrees of applanation) at the face of the rod.

f) The sensitivity to alignment is then compared to the tolerances required for reproducing applanation measurements which depends, in part, on the results obtained in the aforementioned testing and calibration method associated with the alignment apparatus.

g) The sensitivity of the applanation detecting arrangement is then changed as needed by such procedures as changing the size of the aperture in front of the applanation sensor D2 and/or changing the aperture stop (small hole) at the beam splitter BS2.

Further calibration and in-vitro measurements can be carried out as follows: After the aforementioned calibration and testing procedures have been carried out on the individual subassemblies, all parts can be combined and the system tested as an integrated unit. For this purpose, ten enucleated animal eyes and ten enucleated human eyes are measured in two separate series. The procedures for both eye types are the same. The eyes are mounted in non-magnetic holders, each having a central opening which exposes the cornea and part of the sclera. A 23 gauge needle attached to a short piece of polyethylene tubing is then inserted behind the limbus through the sclera and ciliary body and advanced so that the tip passes between the lens and iris. Side ports are drilled in the cannulas about 2 mm from the tip to help avoid blockage of the cannula by the iris or lens. This cannula is attached to a pressure transducer with an appropriate display element. A normal saline reservoir of adjustable height is also connected to the pressure transducer tubing system. The hydrostatic pressure applied to the eye by this reservoir is adjustable between 0 and 50 mm Hg, and intraocular pressure over this range can be measured directly with the pressure transducer.

In order to verify that the foregoing equipment is properly set up for each new eye, a standard Goldman applanation tonometer can be used to independently measure the eye's intraocular pressure at a single height of the reservoir. The intraocular value measured using the Goldman system is then compared to a simultaneously determined intraocular pressure measured by the pressure transducer. Any problems encountered with the equipment can be corrected if the two measurements are significantly different.

The reservoir is used to change in 5 mm Hg sequential steps the intraocular pressure of each eye over a range of pressures from 5 to 50 mm Hg. At each of the pressures, a measurement is taken using the system of the present invention. Each measurement taken by the present invention consists of recording three separate time-varying signals over the time duration of the pulsed magnetic field. The three signals are: 1) the current flowing in the coil of the actuation apparatus as a function of time, labelled I (t), 2) the voltage signal as a function of time from the applanation detector D2, labelled APPLN (t), and 3) the voltage signal as a function of time from the alignment sensor D1, labelled ALIGN (t). The three signals, associated with each measurement, are then acquired and stored in a computer equipped with a multi-input "data acquisition and processing" board and related software.

The computer allows many things to be done with the data including: 1) recording and storing many signals for subsequent retrieval, 2) displaying graphs of the signals versus time, 3) numerical processing and analyses in any way that is desired, 4) plotting final results, 5) applying statistical analyses to groups of data, and 6) labeling the data (e.g. tagging a measurement set with its associated intraocular pressure).

The relationship between the three time-varying signals and intraocular pressure are as follows:

1. I(t) is an independent input signal which is consistently applied as current pulse from the power supply which activates the actuation apparatus. This signal I (t) is essentially constant from one measurement to another except for minor shot-to-shot variations. I (t) is a "reference" waveform against which the other waveforms, APPLN (t) and ALIGN (t) are compared as discussed further below.

2. APPLN(t) is a dependent output signal. APPLN(t) has a value of zero when I(t) is zero (i.e. at the very beginning of the current pulse in the coil of the actuation apparatus. The reason for this is that when I=0, there is no magnetic field and, consequently. no applanation force on the movable central piece. As I (t) increases, so does the extent of applanation and, correspondingly, so does APPLN(t). It is important to note that the rate at which APPLN(t) increases with increasing I(t) depends on the eye's intraocular pressure. Since eyes with low intraocular pressures applanate more easily than eyes with high intraocular pressures in response to an applanation force, it is understood that APPLN(t) increases more rapidly for an eye having a low intraocular pressure than it does for an eye having a high intraocular pressure. Thus, APPLN (t) increases from zero at a rate that is inversely proportional to the intraocular pressure until it reaches a maximum value when full applanation is achieved.

3. ALIGN(t) is also a dependent output signal. Assuming an eye is aligned in the setup, the signal ALIGN(t) starts at some maximum value when I(t) is zero (i.e. at the very beginning of the current pulse to the coil of the actuation apparatus). The reason for this is that when I=0, there is no magnetic field and, consequently, no force on the movable central piece which would otherwise tend to alter the cornea's curvature. Since corneal reflection is what gives rise to the alignment signal, as I(t) increases causing applanation (and, correspondingly, a decrease in the extent of corneal curvature), the signal ALIGN (t) decreases until it reaches zero at full applanation. It is important to note that the rate at which ALIGN (t) decreases with increasing I(t) depends on the eye's intraocular pressure. Since extraocular pressure applanate more easily than eyes with high intraocular pressure, it is understood that ALIGN (t) decreases more rapidly for an eye having a low intraocular pressure than for an eye having a high intraocular pressure. Thus, ALIGN(t) decreases from some maximum value at a rate that is inversely proportional to the intraocular pressure until it reaches zero when full applanation is achieved.

From the foregoing, it is clear that the rate of change of both output signals, APPLN and ALIGN, in relation to the input signal I is inversely proportional to the intraocular pressure. Therefore, the measurement of intraocular pressure using the present invention may depend on determining the SLOPE of the "APPLN versus I" measurement data (also, although probably with less certainty, the slope of the "ALIGN versus I" measurement data).

For the sake of brevity, the following description is limited to the "APPLN versus I" data; however, it is understood that the "ALIGN versus I" data can be processed in a similar manner.

Plots of "APPLN versus I" can be displayed on the computer monitor for the various measurements (all the different intraocular pressures for each and every eye) and regression analysis (and other data reduction algorithms) can be employed in order to obtain the "best fit" SLOPE for each measurement. Time can be spent in order to optimize this data reduction procedure. The end result of a series of pressure measurements at different intraocular pressures on an eye (determined by the aforementioned pressure transducer) will be a corresponding series of SLOPE's (determined by the system of the present invention).

Next, a single plot is prepared for each eye showing SLOPE versus intraocular pressure data points as well as a best fitting curve through the data. Ideally, all curves for the 10 pig eyes are perfectly coincident—with the same being true for the curves obtained for the 10 human eyes. If the ideal is realized, any of the curves can be utilized (since they all are the same) as a CALIBRATION for the present invention. In practice, however, the ideal is probably not realized.

Therefore, all of the SLOPE versus intraocular pressure data for the 10 pig eyes is superimposed on a single plot (likewise for the SLOPE versus intraocular pressure data for the 10 human eyes). Such superimposing generally yields an "averaged" CALIBRATION curve, and also indication of the reliability associated with the CALIBRATION.

Next, the data in the single plots can be analyzed statistically (one for pig eyes and one for human eyes) which, in turn, shows a composite of all the SLOPE versus intraocular pressure data. From the statistical analysis, it is possible to obtain: 1) an averaged CALIBRATION curve for the present invention from which one can obtain the "most likely intraocular pressure" associated with a measured SLOPE value, 2) the Standard Deviation (or Variance) associated with any intraocular pressure determination made using the present invention, essentially the present invention's expected "ability" to replicate measurements, and 3) the "reliability" or "accuracy" of the present invention's CALIBRATION curve which is found from a "standard-error-of-the mean" analysis of the data.

In addition to data obtained with the eyes aligned, it is also possible to investigate the sensitivity of intraocular pressure measurements made using the present invention, to translational and rotational misalignment.

ALTERNATIVE EMBODIMENT FOR MEASURING INTRAOCULAR PRESSURE BY INDENTATION

Figure 20A:
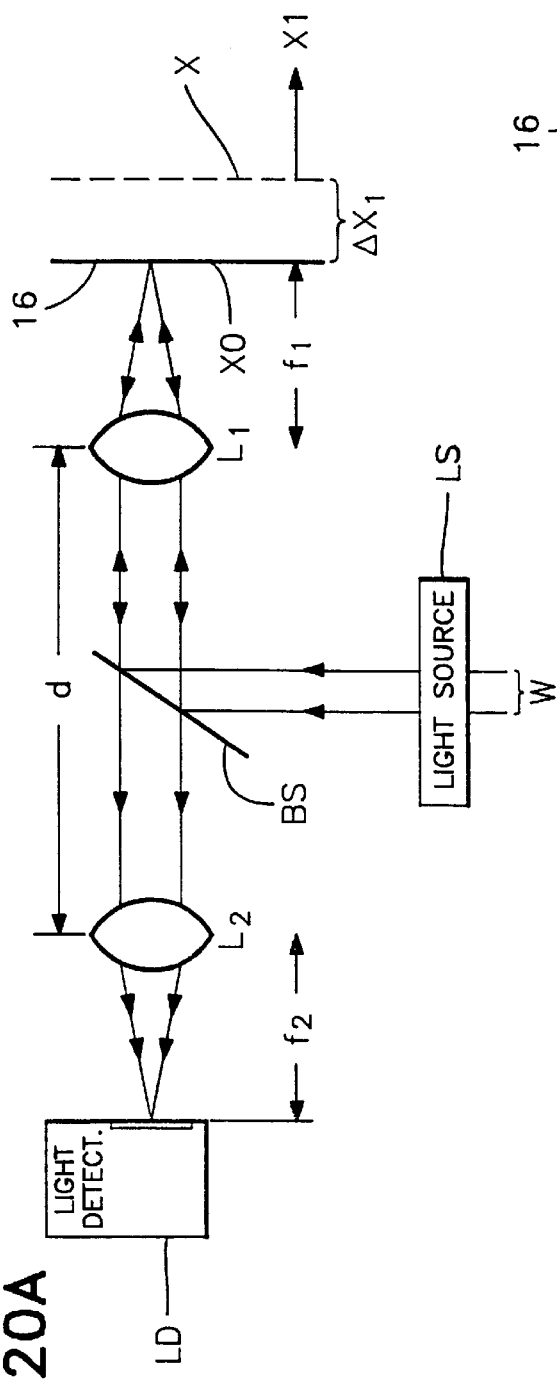
FIGS. 20A and 20B schematically illustrate an alternative embodiment for measuring intraocular pressure by indentation.
Figure 20B:
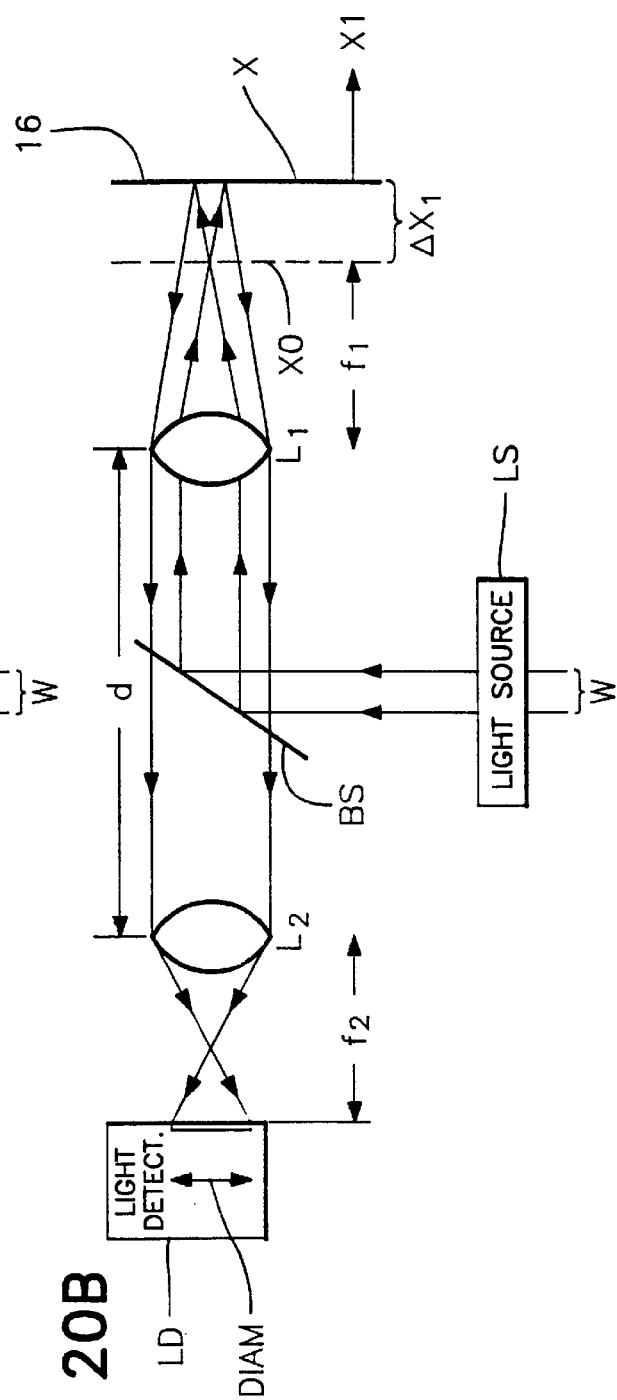

With reference to FIGS. 20A and 20B, an alternative embodiment for measuring intraocular pressure by indentation will now be described.

The alternative embodiment includes an indentation distance detection arrangement and contact device. The contact device has a movable central piece 16 of which only the outside surface is illustrated in FIGS. 20A and 20B. The outside surface of the movable central piece 16 is at least partially reflective.

The indentation distance detection arrangement includes two converging lenses L1 and L2; a beam splitter BS1; a light source LS for emitting a beam of light having a width w; and a light detector LD responsive to the diameter of a reflected beam impinging on a surface thereof.

FIG. 20A illustrates the alternative embodiment prior to actuation of the movable central piece 16. Prior to actuation, the patient is aligned with the indentation distance detection arrangement so that the outer surface of the movable central piece 16 is located at the focal point of the converging lens L2. When the movable central piece 16 is so located, the beam of light from the light source LS strikes the beam splitter BS and is deflected through the converging lens L1 to impinge as a point on the reflective outer surface of the movable central piece 16. The reflective outer surface of the movable central piece 16 then reflects this beam of light back through the converging lens L1, through the beam splitter BS, and then through the converging lens L2 to strike a surface of the light detector LD. Preferably, the light detector LD is located at the focal point of the converging lens L2 so that the reflected beam impinges on a surface of the light detector LD as a point of virtually zero diameter when the outer surface of the movable central piece remains at the focal point of the converging lens L1.

Preferably, the indentation distance detection arrangement is connected to a display device so as to generate an indication of zero displacement when the outer surface of the movable central piece 16 has yet to be displaced, as shown in FIG. 20A.

By subsequently actuating the movable central piece 16 using an actuating device (preferably, similar to the actuating devices described above), the outer surface of the movable central piece 16 moves progressively away from the focal point of the converging lens L1, as illustrated in FIG. 20B. As a result, the light beam impinging on the reflective outer surface of the movable central piece 16 has a progressively increasing diameter. This progressive increase in diameter is proportional to the displacement from the focal point of the converging lens L1. The resulting reflected beam therefore has a diameter proportional to the displacement and passes back through the converging lens L1, through the beam splitter BS, through the converging lens C2 and then strikes the surface of the light detector LD with a diameter proportional to the displacement of the movable central piece 16. Since the light detector LD is responsive, as indicated above, to the diameter of the reflected light beam, any displacement of the movable central piece 16 causes a proportional change in output from the light detector LD.

Preferably, the light detector LD is a photoelectric converter connected to the aforementioned display device and capable of providing an output voltage proportional to the diameter of the reflected light beam impinging upon the light detector LD. The display device therefore provides a visual indication of displacement based on the output voltage from the light detector LD.

Alternatively, the output from the light detector LD may be connected to an arrangement, as described above, for providing an indication of intraocular pressure based on the displacement of the movable central piece 16.

ADDITIONAL CAPABILITIES

Generally, the present apparatus and method makes it possible to evaluate intraocular pressure, as indicated above, as well as ocular rigidity, eye hydrodynamics such as outflow facility and inflow rate of eye fluid, eye hemodynamics such as the pressure in the episcleral veins and the pulsatile ocular blood flow, and has also the ability to artificially increase intraocular pressure, as well as the continuous recording of intraocular pressure.

With regard to the measurement of intraocular pressure by applanation, the foregoing description sets forth several techniques for accomplishing such measurement, including a variable force technique wherein the force applied against the cornea varies with time. It is understood, however, that a variable area method can also be implemented.

The apparatus can evaluate the amount of area applanated by a known force. The pressure is calculated by dividing the force by the amount of area that is applanated. The amount of area applanated is determined using the optical means and/or filters previously described.

A force equivalent to placing 5 gram of weight on the cornea, for example, will applanate a first area if the pressure is 30 mmHg, a second area if the pressure is 20 mmHg, a third area if the pressure is 15 mmHg and so on. The area applanated is therefore indicative of intraocular pressure.

Alternatively, intraocular pressure can be measured using a non-rigid interface and general applanation techniques. In this embodiment, a flexible central piece enclosed by the magnet of the movable central piece is used and the transparent part of the movable central piece acts like a microballoon. This method is based on the principle that the interface between two spherical balloons of unequal radius will be flat if the pressures in the two balloons are equal. The central piece with the balloon is pressed against the eye until the eye/central piece interface is planar as determined by the aforementioned optical means.

Also, with regard to the previously described arrangement which measures intraocular pressure by indentation, an alternative method can be implemented with such an embodiment wherein the apparatus measures the force required to indent the cornea by a predetermined amount. This amount of indentation is determined by optical means as previously described. The movable central piece is pressed against the cornea to indent the cornea, for example, 0.5 mm (though it is understood that virtually any other depth can be used). Achievement of the predetermined depth is detected by the previously described optical means and filters. According to tables, the intraocular pressure can be determined thereafter from the force.

Yet another technique which the present invention facilitates use of is the ballistic principle. According to the ballistic principle, a parameter of a collision between the known mass of the movable central piece and the cornea is measured. This measured parameter is then related theoretically or experimentally to the intraocular pressure. The following are exemplary parameters:

Impact Acceleration

The movable central piece is directed at the cornea at a well defined velocity. It collides with the cornea and, after a certain time of contact, bounces back. The time-velocity relationships during and after impact can be studied. The applanating central piece may have a spring connecting to the rigid annular member of the contact device. If the corneal surface is hard, the impact time will be short. Likewise, if the corneal surface is soft the impact time will be longer. Optical sensors can detect optically the duration of impact and how long it takes for the movable central piece to return to its original position.

Impact Duration

Intraocular pressure may also be estimated by measuring the duration of contact of a spring driven movable central piece with the eye. The amount of time that the cornea remains flattened can be evaluated by the previously described optical means.

Rebound Velocity

The distance traveled per unit of time after bouncing is also indicative of the rebound energy and this energy is proportional to intraocular pressure.

Vibration Principle

The intraocular pressure also can be estimated by measuring the frequency of a vibrating element in contact with the contact device and the resulting changes in light reflection are related to the pressure in the eye.

Time

The apparatus of the present invention can also be used, as indicated above, to measure the time that it takes to applanate the cornea. The harder the cornea, the higher the intraocular pressure and thus the longer it takes to deform the cornea. On the other hand, the softer the cornea, the lower the intraocular pressure and thus the shorter it takes to deform the cornea. Thus, the amount of time that it takes to deform the cornea is proportional to the intraocular pressure.

Additional uses and capabilities of the present invention relate to alternative methods of measuring outflow facility (tonography). These alternative methods include the use of conventional indentation techniques, constant depth indentation techniques, constant pressure indentation techniques, constant pressure applanation techniques, constant area applanation techniques, and constant force applanation techniques.

1. Conventional Indentation

When conventional indentation techniques are utilized, the movable central piece of the present invention is used to indent the cornea and thereby artificially increase the intraocular pressure. This artificial increase in intraocular pressure forces fluid out of the eye more rapidly than normal. As fluid leaves the eye, the pressure gradually returns to its original level. The rate at which the intraocular pressure falls depends on how well the eye's drainage system is functioning. The drop in pressure as a function of time is used to calculated the C value or coefficient of outflow facility. The C value is indicative of the degree to which a change in intraocular pressure will cause a change in the rate of fluid outflow. This, in turn, is indicative of the resistance to outflow provided by the eye's drainage system. The various procedures for determining outflow facility are generally known as tonography and the C value is typically expressed in terms of microliters per minute per millimeter of mercury. The C value is determined by raising the intraocular pressure using the movable central piece of the contact device and observing the subsequent decay in intraocular pressure with respect to time. The elevated intraocular pressure increases the rate of aqueous outflow which, in turn, provides a change in volume. This change in volume can be calculated from the Friedenwald tables which correlate volume change to pressure changes. The rate of volume decrease equals the rate of outflow. The change in intraocular pressure during the tonographic procedure can be computed as an arithmetical average of pressure increments for successive ½ minute intervals. The C value is derived then from the following equation: $C=\Delta V/t^* $ (Pave-Po), in which t is the duration of the procedure, Pave is the average pressure elevation during the test and can be measured, Po is the initial pressure and it is also measured, and $\Delta V$ is difference between the initial and final volumes and can be obtained from known tables. The Flow ("F") of fluid is then calculated using the formula: $F=C^*$ (Po-Pv), in which Pv is the pressure in the episcleral veins which can be measured and generally has a constant value of 10.

2. Constant Depth Indentation

When constant depth indentation techniques are utilized, the method involves the use of a variable force which is necessary to cause a certain predetermined amount of indentation in the eye. The apparatus of the present invention is therefore configured so as to measure the force required to indent the cornea by a predetermined amount. This amount of indentation may be detected using optical means as previously described. The movable central piece is pressed against the cornea to indent the eye, for example, by approximately 0.5 mm. The amount of indentation is detected by the optical means and filters previously described. With the central piece indenting the cornea using a force equivalent to a weight of 10 grams, a 0.5 mm indentation will be achieved under normal pressure conditions (e.g., intraocular pressure of 15 mm Hg) and assuming there is an average corneal curvature. With that amount of indentation and using standard dimensions for the central piece, 2.5 mm$^3$ of fluid will be displaced. The force recorded by the present invention undergoes a slow decline and it levels off at a more or less steady state value after 2 to 4 minutes. The decay in pressure is measured based on the difference between the value of the first indentation of the central piece and the final level achieved after a certain amount of time. The pressure drop is due to the return of pressure to its normal value, after it has been artificially raised by the indentation caused by the movable central piece. A known normal value of decay is used as a reference and is compared to the values obtained. Since the foregoing provides a continuous recording of pressure over time, this method can be an important tool for physiological research by showing, for example, an increase in pressure during forced expiration. The pulse wave and pulse amplitude can also be evaluated and the pulsatile blood flow calculated.

3. Constant Pressure Indentation

When constant pressure indentation techniques are utilized, the intraocular pressure is kept constant by increasing the magnetic field and thereby increasing the force against the cornea as fluid leaks out of the eye. At any constant pressure, the force and rate of outflow are linearly related according to the Friedenwald tonometry tables. The intraocular pressure is calculated using the same method as described for conventional indentation tonometry. The volume displacement is calculated using the tonometry tables. The facility of outflow (C) may be computed using two different techniques. According to the first technique, C can be calculated from two constant pressure tonograms at different pressures according to the equation, $C=\{[(\Delta V_1/t_1)-(\Delta V_2/t_2)]/(P_1-P_2)\}$, in which 1 corresponds to a measurement at a first pressure and 2 corresponds to a measurement at a second pressure (which is higher than the first pressure). The second way to calculate C is from one constant pressure tonogram and an independent measure of intraocular pressure using applanation tonometry ($P_a$) in $C=[(\Delta V/t)/(P-P_a-\Delta P_e)]$, where $\Delta P_e$ is a correction factor for rise in episcleral venous pressure with indentation tonometry and P is the intraocular pressure obtained using indentation tonometry.

4. Constant Pressure Applanation

When constant pressure applanation techniques are utilized, the intraocular pressure is kept constant by increasing the magnetic field and thus the force as fluid leaks out of the eye. If the cornea is considered to be a portion of a sphere, a mathematical formula relates the volume of a spherical segment to the radius of curvature of the sphere and the radius of the base of the segment. The volume displaced is calculated based on the formula $V=A^2/(4*\pi*R)$, in which V is volume, A is the area of the segment base, and R is the radius of curvature of the sphere (this is the radius of curvature of the cornea). Since A=weight/pressure, then $V=W^2/(4*\pi*R*P^2)$. The weight is constituted by the force in the electromagnetic field, R is the curvature of the cornea and can be measured with a keratometer, P is the pressure in the eye and can be measured using the same method as described for conventional applanation tonometry. It is therefore possible to calculate the volume displaced and the C value or outflow facility. The volume displaced, for example, can be calculated at 15 second intervals and is plotted as a function of time.

5. Constant Area Applanation

When constant area applanation techniques are utilized, the method consists primarily of evaluating the pressure decay curve while the flattened area remains constant. The aforementioned optical applanation detecting arrangements can be used in order to keep constant the area flattened by the movable central piece. The amount of force necessary to keep the flattened area constant decreases and this decrease is registered. The amount of volume displaced according to the different areas of applanation is known. For instance, a 5 mm applanating central piece displaces 4.07 mm$^3$ of volume for the average corneal radius of 7.8 mm. Using the formula $\Delta V/\Delta t=1/(R*\Delta P)$, it is possible to calculate R which is the reciprocal of C. Since a continuous recording of pressure over time is provided, this method can be an important tool for research and evaluation of blood flow.

6. Constant Force Applanation

When constant force applanation techniques are utilized, the same force is constantly applied and the applanated area is measured using any of the aforementioned optical applanation detection arrangements. Once the area flattened by a known force is measured, the pressure can be calculated by dividing the force by the amount of area that is applanated. As fluid leaves the eye the amount of area applanated increases with time. This method consists primarily of evaluating a resulting area augmentation curve while the constant force is applied. The amount of volume displaced according to the different areas of applanation is known. Using the formula $\Delta V/\Delta t=1/(R*\Delta P)$, it is possible to calculate R which is the reciprocal of C.

Still additional uses of the present invention relate to detecting the frequency response of the eye, using indentation tonometry. In particular, if an oscillating force is applied using the movable central piece 16, the velocity of the movable central piece 16 is indicative of the eye's frequency response. The system oscillates at the resonant frequency determined primarily by the mass of the movable central piece 16. By varying the frequency of the force and by measuring the response, the intraocular pressure can be evaluated. The evaluation can be made by measuring the resonant frequency and a significant variation in resonant frequency can be obtained as a function of the intraocular pressure.

The present invention may also be used with the foregoing conventional indentation techniques, but where the intraocular pressure used for calculation is measured using applanation principles. Since applanation virtually does not disturb the hydrodynamic equilibrium because it displaces a very small volume, this method can be considered more accurate than intraocular pressure measurements made using traditional indentation techniques.

Another use of the present invention involves a time related way of measuring the resistance to outflow. In particular, the resistance to outflow is detected by measuring the amount of time necessary to transfigure the cornea with either applanation or indentation. The time necessary to displace, for example, 5 microliters of eye fluid would be 1 second for normal patients and above 2 seconds for glaucoma-stricken individuals.

Yet another use of the present invention involves measuring the inflow of eye fluid. In particular, this measurement is made by applying the formula $F=\Delta P/R$, in which $\Delta P$ is $P-P_v$, and P is the steady state intraocular pressure and $P_v$ is the episcleral venous pressure which, for purposes of calculation, is considered constant at 10. R is the resistance to outflow, which is the reciprocal of C that can be calculated. F, in units of volume/min, can then be calculated.

The present invention is also useful at measuring ocular rigidity, or the distensibility of the eye in response to an increased intraocular pressure. The coefficient of ocular rigidity can be calculated using a nomogram which is based on two tonometric readings with different weights. A series of conversion tables to calculate the coefficient of ocular rigidity was developed by Friedenwald. The technique for determining ocular rigidity is based on the concept of differential tonometry, using two indentation tonometric readings with different weights or more accurately, using one indentation reading and one applanation reading and plotting these readings on the nomogram. Since the present invention can be used to measure intraocular pressure using both applanation and indentation techniques, a more accurate evaluation of the ocular rigidity can be achieved.

Measurements of intraocular pressure using the apparatus of the present invention can also be used to evaluate hemodynamics, in particular, eye hemodynamics and pulsatile ocular blood flow. The pulsatile ocular blood flow is the component of the total ocular arterial inflow that causes a rhythmic fluctuation of the intraocular pressure. The intraocular pressure varies with each pulse due to the pulsatile influx of a bolus of arterial blood into the eye with each heartbeat. This bolus of blood enters the intraocular arteries with each heartbeat causing a temporary increase in the intraocular pressure. The period of inflow causes a stretching of the eye walls with a concomitant increase in pressure followed by a relaxation to the previous volume and a return to the previous pressure as the blood drains from the eye. If this process of expansion during systole (contraction of the heart) and contraction during diastole (relaxation of the heart) occurs at a certain pulse rate, then the blood flow rate would be the incremental change in eye volume times the pulse rate.

The fact that intraocular pressure varies with time according to the cardiac cycle is the basis for measuring pulsatile ocular blood flow. The cardiac cycle is approximately in the order of 0.8 Hz. The present invention can measure the time variations of intraocular pressure with a frequency that is above the fundamental human heart beat frequency allowing the evaluation and recording of intraocular pulse. In the normal human eye, the intraocular pulse has a magnitude of approximately 3 mm Hg and is practically synchronous with the cardiac cycle.

As described, measurements of intraocular pressure show a time variation that is associated with the pulsatile component of arterial pressure. Experimental results provide means of transforming ocular pressure changes into eye volume changes. Each bolus of blood entering the eye increases the ocular volume and the intraocular pressure. The observed changes in pressure reflect the fact that the eye volume must change to accommodate changes in the intraocular blood volume induced by the arterial blood pulse. This pulse volume is small relative to the ocular volume, but because the walls of the eye are stiff, the pressure increase required to accommodate the pulse volume is significant and can be measured. Therefore, provided that the relationship between the increased intraocular pressure and increased ocular volume is known, the volume of the bolus of fluid can be determined. Since this relationship between pressure change and volume change has been well established (Friedenwald 1937, McBain 1957, Ytteborg 1960, Eisenlohr 1962, McEwen 1965), the pressure measurements can be used to obtain the volume of a bolus of blood and thereby determine the blood flow.

The output of the tonometer for the instantaneous pressure can be converted into instantaneous change in eye volume as a function of time. The time derivative of the change in ocular volume is the net instantaneous pulsatile component of the ocular blood flow. Under these conditions, the rate of pulsatile blood flow through the eye can be. evaluated from the instantaneous measurement of intraocular pressure. In order to rapidly quantify and analyze the intraocular pulse, the signal from the tonometer may be digitalized and fed into a computer.

Moreover, measurements of intraocular pressure can be used to obtain the intraocular volume through the use of an independently determined pressure-volume relationship such as with the Friedenwald equation (Friedenwald, 1937). A mathematical model based on experimental data from the pressure volume relationship (Friedenwald 1937, McBain 1957, Eisenlohr 1962, McEwen 1965) can also be used to convert a change in ocular pressure into a change in ocular volume.

In addition, a model can also be constructed to estimate the ocular blood flow from the appearance of the intraocular pressure waveform. The flow curve is related to parameters that come from the volume change curve. This curve is indirectly measured since the intraocular pressure is the actual measured quantity which is transformed into volume change through the use of the measured pressure-volume relation. The flow is then computed by taking the change in volume Vmax-Vmin multiplied by a constant that is related to the length of the time interval of the inflow and the total pulse length. Known mathematical calculations can be used to evaluate the pulsatile component of the ocular blood flow. Since the present invention can also be used to measure the ocular rigidity, this parameter of coefficient of ocular rigidity can be used in order to more precisely calculate individual differences in pulsatile blood flow.

Moreover, since the actuation apparatus 6 and contact device 2 of the present invention preferably include transparent portions, the pulsatile blood flow can be directly evaluated optically to quantify the change in size of the vessels with each heart beat. A more precise evaluation of blood flow therefore can be achieved by combining the changes in intraocular pulse with changes in vessel diameter which can be automatically measured optically.

A vast amount of data about the vascular system of the eye and central nervous system can be obtained after knowing the changes in intraocular pressure over time and the amount of pulsatile ocular blood flow. The intraocular pressure and intraocular pulse are normally symmetrical in pairs of eyes. Consequently, a loss of symmetry may serve as an early sign of ocular or cerebrovascular disease. Patients afflicted with diabetes, macular degeneration, and other vascular disorders may also have a decreased ocular blood flow and benefit from evaluation of eye hemodynamics using the apparatus of the present invention.

The present invention may also be used to artificially elevate intraocular pressure. The artificial elevation of intraocular pressure is an important tool in the diagnosis and prognosis of eye and brain disorders as well as an important tool for research.

Figure 21:
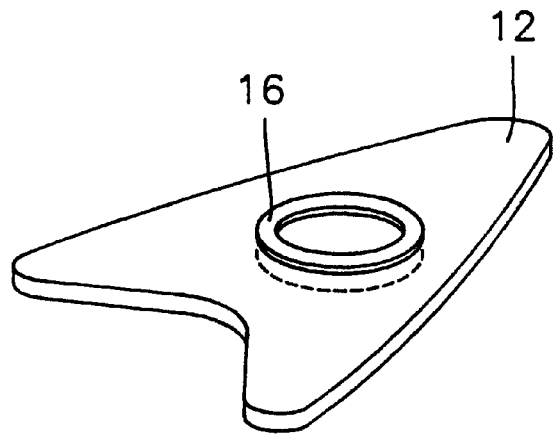
FIGS. 21 and 22 schematically illustrate embodiments of the present invention which facilitate placement of the contact device on the sclera of the eye.
Figure 22:
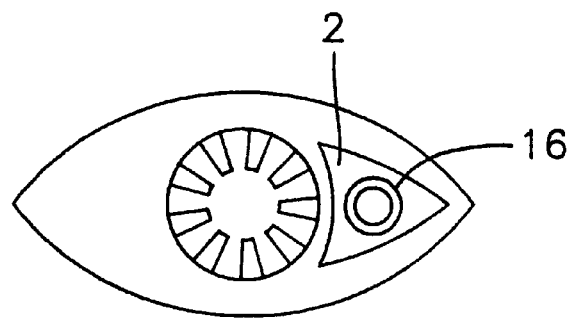

Artificial elevation of intraocular pressure using the present invention can be accomplished in different ways. According to one way, the contact device of the present invention is modified in shape for placement on the sclera (white of the eye). This arrangement, which will be described hereinafter, is illustrated in FIGS. 21–22, wherein the movable central piece 16 may be larger in size and is preferably actuated against the sclera in order to elevate the intraocular pressure. The amount of indentation can be detected by the optical detection system previously described.

Another way of artificially increasing the intraocular pressure is by placing the contact device of the present invention on the cornea in the same way as previously described, but using the movable central piece to apply a greater amount of force to achieve deeper indentation. This technique advantageously allows visualization of the eye while exerting the force, since the movable central portion of the contact device is preferably transparent. According to this technique, the size of the movable central piece can also be increased to indent a larger area and thus create a higher artificial increase of intraocular pressure. Preferably, the actuation apparatus also has a transparent central portion, as indicated above, to facilitate direct visualization of the eye and retina while the intraocular pressure is being increased. When the intraocular pressure exceeds the ophthalmic arterial diastolic pressure, the pulse amplitude and blood flow decreases rapidly. Blood flow becomes zero when the intraocular pressure is equal or higher than the ophthalmic systolic pressure. Thus, by allowing direct visualization of the retinal vessels, one is able to determine the exact moment that the pulse disappears and measure the pressure necessary to promote the cessation of the pulse which, in turn, is the equivalent of the pulse pressure in the ophthalmic artery. The present invention thus allows the measurement of the pressure in the arteries of the eye.

Also, by placing a fixation light in a back portion of the actuation apparatus and asking the patient to indicate when he/she can no longer see the light, one can also record the pressure at which a patient's vision ceases. This also would correspond to the cessation of the pulse in the artery of the eye. The pressure in which vessels open can also be determined by increasing intraocular pressure until the pulse disappears and then gradually decreasing the intraocular pressure until the pulse reappears. Thus, the intraocular pressure necessary for vessels to open can be evaluated.

It is important to note that the foregoing measurements can be performed automatically using an optical detection system, for example, by aiming a light beam at the pulsating blood vessel. The cessation of pulsation can be optically recognized and the pressure recorded. An attenuation of pulsations can also be used as the end point and can be optically detected. The apparatus also allows direct visualization of the papilla of the optic nerve while an increased intraocular pressure is produced. Thus, physical and chemical changes occurring inside the eye due to the artificial increase in intraocular pressure may be evaluated at the same time that pressure is measured.

Advantageously, the foregoing, test can be performed on patients with media opacities that prevent visualization of the back of the eye. In particular, the aforementioned procedure wherein the patient indicates when vision ceases is particular useful in patients with media opacities. The fading of the peripheral vision corresponds to the diastolic pressure and fading of the central vision corresponds to the systolic pressure.

The present invention, by elevating the intraocular pressure, as indicated above and by allowing direct visualization of blood vessels in the back of the eye, may be used for tamponade (blockade of bleeding by indirect application of pressure) of hemorrhagic processes such as those which occur, for example, in diabetes and macular degeneration. The elevation of intraocular pressure may also be beneficial in the treatment of retinal detachments.

As yet another use of the present invention, the aforementioned apparatus also can be used to measure outflow pressure of the eye fluid. In order to measure outflow pressure in the eye fluid, the contact device is placed on the cornea and a measurable pressure is applied to the cornea. The pressure causes the aqueous vein to increase in diameter when the pressure in the cornea equals the outflow pressure. The pressure on the cornea is proportional to the outflow pressure. The flow of eye fluid out of the eye is regulated according to Poiseuille's Law for laminar currents. If resistance is inserted into the formula, the result is a formula similar to Ohm's Law. Using these known formulas, the rate of flow (volume per time) can be determined. The change in the diameter of the vessel which is the reference point can be detected manually by direct observation and visualization of the change in diameter or can be done automatically using an optical detection system capable of detecting a change in reflectivity due to the amount of fluid in the vein and the change in the surface area. The actual cross-section of the vein can be detected using an optical detection system.

The eye and the brain are hemodynamically linked by the carotid artery and the autonomic nervous system. Pathological changes in the carotid, brain, heart, and the sympathetic nervous system can secondarily affect the blood flow to the eye. The eye and the brain are low vascular resistance systems with high reactivity. The arterial flow to the brain is provided by the carotid artery. The ophthalmic artery branches off of the carotid at a 90 degree angle and measures approximately 0.5 mm in diameter in comparison to the carotid which measures 5 mm in diameter. Thus, most processes that affect the flow to the brain will have a profound effect on the eye. Moreover, the pulsation of the central retinal artery may be used to determine the systolic pressure in the ophthalmic artery, and due to its anatomic relationship with the cerebral circulatory system, the pressure in the brain's vessels can be estimated. Total or partial occlusion of the vascular system to the brain can be determined by evaluating the ocular blood flow. There are numerous vascular and nervous system lesions that alter the ocular pulse amplitude and/or the intraocular pressure curve of the eye. These pathological situations may produce asymmetry of measurements between the two eyes and/or a decrease of the central retinal artery pressure, decrease of pulsatile blood flow and alter the pulse amplitude.

An obstruction in the flow in the carotid (cerebral circulation) can be evaluated by analyzing the ocular pulse amplitude and area, pulse delay and pulse width, form of the wave and by harmonic analysis of the ocular pulse.

The eye pulsation can be recorded optically according to the change in reflection of the light beam projected to the cornea. The same system used to record distance traveled by the movable central piece during indentation can be used on the bare cornea to detect the changes in volume that occurs with each pulsation. The optical detection system records the variations in distance from the surface of the cornea that occurs with each heart beat. These changes in the position of the cornea are induced by the volume changes in the eye. From the pulsatile character of these changes, the blood flow to the eye can be calculated.

With the aforementioned technique of artificial elevation of pressure, it is possible to measure the time necessary for the eye to recover to its baseline and this recovery time is an indicator of the presence of glaucoma and of the coefficient of outflow facility.

Figure 23:
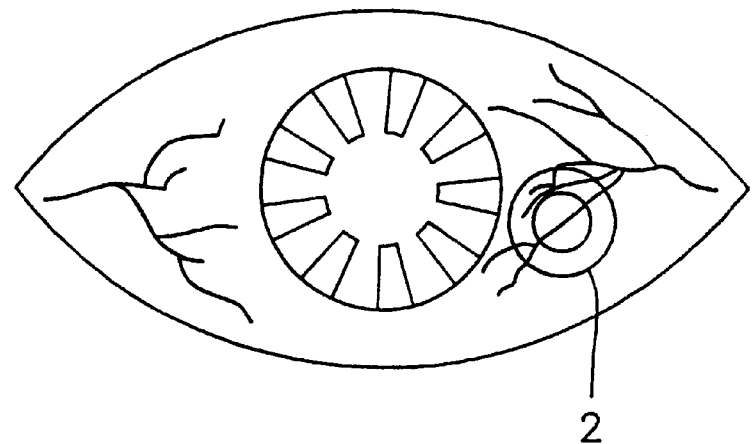
FIG. 23 is a plan view of an alternative contact device which may be used to measure episcleral venous pressure in accordance with the present invention.

The present invention may also be used to measure pressure in the vessels on the surface of the eye, in particular the pressure in the episcleral veins. The external pressure necessary to collapse a vein is utilized in this measurement. The method involves applying a variable force over a constant area of conjunctive overlying the episcleral vein until a desired end point is obtained. The pressure is applied directly onto the vessel itself and the preferred end point is when the vessel collapses. However, different end points may be used, such as blanching of the vessel which occurs prior to the collapse. The pressure of the end point is determined by dividing the force applied by the area of the applanating central piece in a similar way as is used for tonometry. The vessel may be observed through a transparent applanating movable central piece using a slit-lamp biomicroscope. The embodiment for this technique preferably includes a modified contact device which fits on the sclera (FIG. 23). The preferred size of the tip ranges from 250 micrometers to 500 micrometers. Detection of the end point can be achieved either manually or automatically.

According to the manual arrangement, the actuation apparatus is configured for direct visualization of the vessel through a transparent back window of the actuation apparatus, and the time of collapse is manually controlled and recorded. According to an automatic arrangement, an optical detection system is configured so that, when the blood stream is no longer visible, there is a change in a reflected light beam in the same way as described above for tonometry, and consequently, the pressure for collapse is identifiable automatically. The end point marking in both situations is the disappearance of the blood stream, one detected by the operator's vision and the other detected by an optical detection system. Preferably, in both cases, the contact device is designed in a way to fit the average curvature of the sclera and the movable central piece, which can be a rigid or flexible material, is used to compress the vessel.

The present invention may also be used to provide real-time recording of intraocular pressure. A built-in single chip microprocessor can be made responsive to the intraocular pressure measurements over time and can be programmed to create and display a curve relating pressure to time. The relative position of the movable central piece can be detected, as indicated above, using an optical detection system and the detected position in combination with information regarding the amount of current flowing through the coil of the actuation apparatus can be rapidly collected and analyzed by the microprocessor to create the aforementioned curve.

It is understood that the use of a microprocessor is not limited to the arrangement wherein curves are created. In fact, microprocessor technology may be used to create at least the aforementioned calculation unit 10 of the present invention. A microprocessor preferably evaluates the signals and the force that is applied. The resulting measurements can be recorded or stored electronically in a number of ways. The changes in current over time, for example, can be recorded on a strip-chart recorder. Other methods of recording and storing the data can be employed. Logic microprocessor control technology can also be used in order to better evaluate the data.

Still other uses of the present invention relate to evaluation of pressure in deformable materials in industry and medicine. One such example is the use of the present invention to evaluate soft tissue, such as organs removed from cadavers. Cadaver dissection is a fundamental method of learning and studying the human body. The deformability of tissues such as the brain, liver, spleen, and the like, can be measured using the present invention and the depth of indentation can be evaluated. In this regard, the contact device of the present invention can be modified to fit over the curvature of an organ. When the movable central piece rests upon a surface, it can be actuated to project into the surface a distance which is inversely proportional to the tension of the surface and rigidity of the surface to deformation. The present invention can also be used to evaluate and quantify the amount of cicatrization, especially in burn scar therapy. The present invention can be used to evaluate the firmness of the scar in comparison to normal skin areas. The scar skin tension is compared to the value of normal skin tension. This technique can be used to monitor the therapy of patients with burn scars allowing a numerical quantification of the course of cicatrization. This technique can also be used as an early indicator for the development of hypertrophic (thick and elevated) scarring. The evaluation of the tissue pressure and deformability in a variety of conditions such as: a) lymphoedema b) post-surgical effects, such as with breast surgery, and c) endoluminal pressures of hollow organs, is also possible with the apparatus. In the above cases, the piston-like arrangement provided by the contact device does not have to be placed in an element that is shaped like a contact lens. To the contrary, any shape and size can be used, with the bottom surface preferably being flat and not curved like a contact lens.

Yet another use of the present invention relates to providing a bandage lens which can be used for extended periods of time. Glaucoma and increased intraocular pressure are leading causes for rejection of corneal transplants. Many conventional tonometers in the market are unable to accurately measure intraocular pressure in patients with corneal disease. For patients with corneal disease and who have recently undergone corneal transplant, a thinner and larger contact device is utilized and this contact device can be used for a longer period of time. The device also facilitates measurement of intraocular pressure in patients with corneal disease which require wearing of contact lenses as part of their treatment.

The present invention may also be modified to non-invasively measure infant intracranial pressure, or to provide instantaneous and continuous monitoring of blood pressure through an intact wall of a blood vessel. The present invention may also be used in conjunction with a digital pulse meter to provide synchronization with the cardiac cycle. Also, by providing a contact microphone, arterial pressure can be measured. The present invention may also be used to create a dual tonometer arrangement in one eye. A first tonometer can be defined by the contact device of the present invention applied over the cornea, as described above. The second tonometer can be defined by the previously mentioned contact device which is modified for placement on the temporal sclera. In using the dual tonometer arrangement, it is desirable to permit looking into the eye at the fundus while the contact devices are being actuated. Accordingly, at least the movable central piece of the contact device placed over the cornea is preferably transparent so that the fundus can be observed with a microscope.

Although the foregoing illustrated embodiments of the contact device generally show only one movable central piece 16 in each contact device 2, it is understood that more than one movable central piece 16 can be provided without departing from the scope and spirit of the present invention. Preferably, the multiple movable central pieces 16 would be concentrically arranged in the contact device 2, with at least one of the flexible membranes 14 interconnecting the concentrically arranged movable central pieces 16. This arrangement of multiple movable central pieces 16 can be combined with any of the aforementioned features to achieve a desired overall combination.

Although the foregoing preferred embodiments include at least one magnetically actuated movable central piece 16, it is understood that there are many other techniques for actuating the movable central piece 16. Sound or ultrasound generation techniques, for example, can be used to actuate the movable central piece. In particular, the sonic or ultrasonic energy can be directed to a completely transparent version of the movable central piece which, in turn, moves in toward the cornea in response to the application of such energy.

Similarly, the movable central piece may be provided with means for retaining a static electrical charge. In order to actuate such a movable central piece, an actuation mechanism associated therewith would create an electric field of like polarity, thereby causing repulsion of the movable central piece away from the source of the electric field.

Other actuation techniques, for example, include the discharge of fluid or gas toward the movable central piece, and according to a less desirable arrangement, physically connecting the movable central piece to a mechanical actuation device which, for example, may be motor driven and may utilize a strain gauge.

Alternatively, the contact device may be eliminated in favor of a movable central piece in an actuation apparatus. According to this arrangement, the movable central piece of the actuation apparatus may be connected to a slidable shaft in the actuation apparatus, which shaft is actuated by a magnetic field or other actuation means. Preferably, a physician applies the movable central piece of the actuation apparatus to the eye and presses a button which generates the magnetic field. This, in turn, actuates the shaft and the movable central piece against the eye. Preferably, the actuation apparatus, the shaft, and the movable central piece of the actuation apparatus are appropriately arranged with transparent portions so that the inside of the patient's eye remains visible during actuation.

Any of the above described detection techniques, including the optical detection technique, can be used with the alternative actuation techniques.

Also, the movable central piece 16 may be replaced by an inflatable bladder (not shown) disposed of the substantially rigid annular member 12. When inflated, the bladder extends out of the hole in the substantially rigid annular member 12 and toward the cornea.

Similarly, although some of the foregoing preferred embodiments utilize an optical arrangement for determining when the predetermined amount of applanation has been achieved, it is understood that there are many other techniques for determining when applanation occurs. The contact device, for example, may include an electrical contact arranged so as to make or break an electrical circuit when the movable central piece moves a distance corresponding to that which is necessary to produce applanation. The making or breaking of the electrical circuit is then used to signify the occurrence of applanation.

It is also understood that, after applanation has occurred, the time which it takes for the movable central piece 16 to return to the starting position after termination of the actuating force will be indicative of the intraocular pressure, when the intraocular pressure is high, the movable central piece 16 returns more quickly to the starting position. Similarly, for lower intraocular pressures, it takes longer for the movable central piece 16 to return to its starting position. Therefore, the present invention can be configured to also consider the return time of the movable central piece 16 in determining the measured intraocular pressure.

As indicated above, the present invention may be formed with a transparent central portion in the contact device. This transparent central portion advantageously permits visualization of the inside of the eye (for example, the optic nerve) while the intraocular pressure is artificially increased using the movable central piece. Some of the effects of increased intraocular pressure on the optic nerve, retina, and vitreous are therefore readily observable through the present invention, while intraocular pressure is measured simultaneously.

With reference to FIGS. 21 and 22, although the foregoing examples describe placement of the contact device 2 on the cornea, it is understood that the contact device 2 of the present invention may be configured with a quasi-triangular shape (defined by the substantially rigid annular member) to facilitate placement of the contact device 2 on the sclera of the eye.

Figure 24:
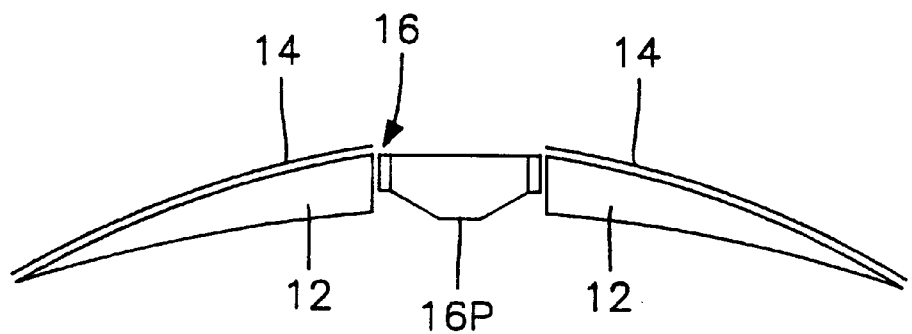
FIG. 24 is a cross-sectional view of the alternative contact device which may be used to measure episcleral venous pressure in accordance with the present invention.
Figure 27:
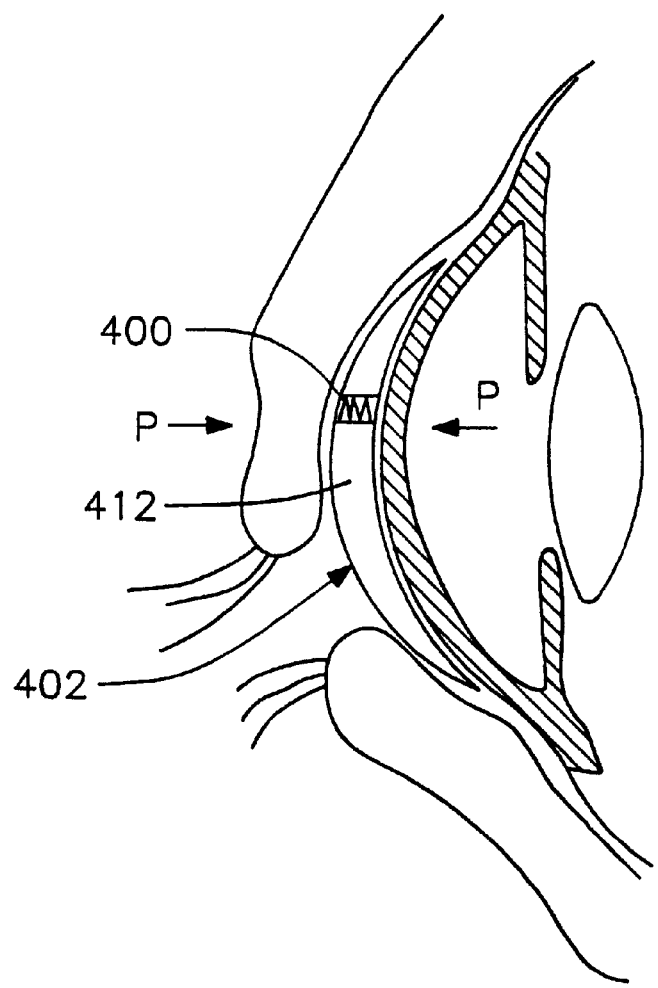
FIG. 27 schematically illustrates the alternative embodiment of FIG. 25 when located in a patient's eye.
Figure 25A:
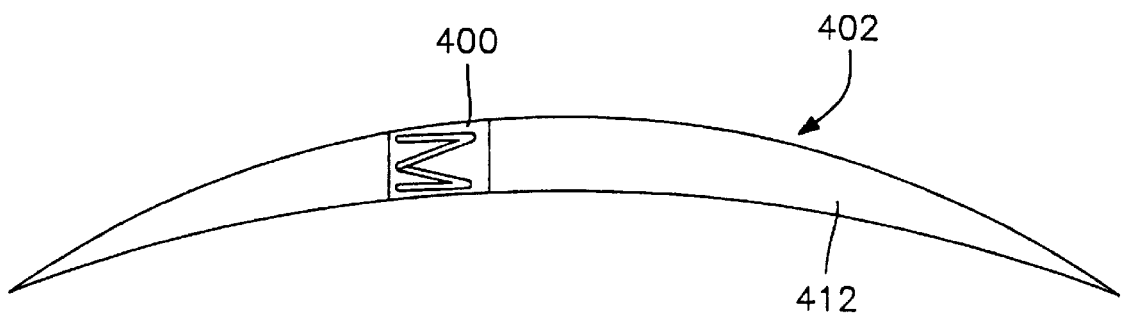
FIG. 25A is a cross-sectional view of the alternative embodiment illustrated in FIG. 25.
Figure 25:
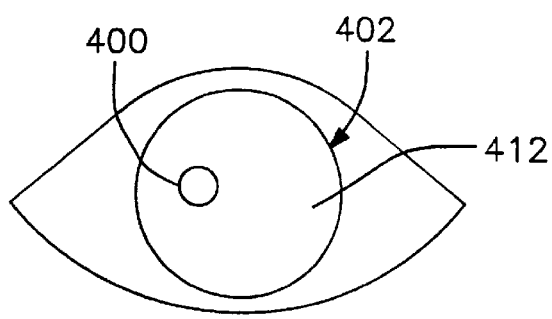
FIG. 25 schematically illustrates an alternative embodiment of the present invention, which includes a contact device with a pressure transducer mounted therein.

With reference to FIGS. 23 and 24, the contact device 2 of the present invention may be used to measure episcleral venous pressure. Preferably, when episcleral venous pressure is to be measured, the movable central piece 6 has a transparent centrally disposed frustoconical projection 16P. The embodiment illustrated FIG. 24 advantageously permits visualization of the subject in through at least the transparent central portion of the movable central piece 16.

Furthermore, as indicated above, the present invention may also be used to measure pressure in other parts of the body (for example, scar pressure in the context of plastic surgery) or on surfaces of various objects. The contact device of the present invention, therefore, is not limited to the corneal-conforming curved shape illustrated in connection with the exemplary embodiments, but rather may have various other shapes including a generally flat configuration.

ALTERNATIVE EMBODIMENT ACTUATED BY CLOSURE OF THE EYE LID

With reference to FIGS. 25–31, an alternative embodiment of the system will now be described. The alternative apparatus and method uses the force and motion generated by the eye lid during blinking and/or closure of the eyes to act as the actuation apparatus and activate at least one transducer 400 mounted in the contact device 402 when the contact device 402 is on the cornea. The method and device facilitate the remote monitoring of pressure and other physiological events by transmitting the information through the eye lid tissue, preferably via electromagnetic waves. The information transmitted is recovered at a receiver 404 remotely placed with respect to the contact device 402, which receiver 404 is preferably mounted in the frame 408 of a pair of eye glasses. This alternative embodiment also facilitates utilization of forceful eye lid closure to measure outflow facility. The transducer is preferably a microminiature pressure-sensitive transducer 400 that alters a radio frequency signal in a manner indicative of physical pressure exerted on the transducer 400.

Although the signal response from the transducer 400 can be communicated by cable, it is preferably actively or passively transmitted in a wireless manner to the receiver 404 which is remotely located with respect to the contact device 402. The data represented by the signal response of the transducer 400 can then be stored and analyzed. Information derived from this data can also be communicated by telephone using conventional means.

According to the alternative embodiment, the apparatus comprises at least one pressure-sensitive transducer 400 which is preferably activated by eye lid closure and is mounted in the contact device 402. The contact device 402, in turn, is located on the eye. In order to calibrate the system, the amount of motion and squeezing of the contact device 402 during eye lid motion/closure is evaluated and calculated. As the upper eyelid descends during blinking, it pushes down and squeezes the contact device 402, thereby forcing the contact device 402 to undergo a combined sliding and squeezing motion.

Since normal individuals involuntarily blink approximately every 2 to 10 seconds, this alternative embodiment of the present invention provides frequent actuation of the transducer 400. In fact, normal individuals wearing a contact device 402 of this type will experience an increase in the number of involuntary blinks, and this, in turn, tends to provide quasi-continuous measurements. During sleep or with eyes closed, since there is uninterrupted pressure by the eye lid, the measurements can be taken continuously.

As indicated above, during closure of the eye, the contact device 402 undergoes a combined squeezing and sliding motion caused by the eye lid during its closing phase.

Initially the upper eye lid descends from the open position until it meets the upper edge of the contact device 402, which is then pushed downward by approximately 0.5 mm to 2 mm. This distance depends on the type of material used to make the structure 412 of the contact device 402 and also depends on the diameter thereof.

When a rigid structure 412 is used, there is little initial overlap between the lid and the contact device 402. When a soft structure 412 is used, there is a significant overlap even during this initial phase of eye lid motion. After making this initial small excursion the contact device 402 comes to rest, and the eye lid then slides over the outer surface of the contact device 402 squeezing and covering it. It is important to note that if the diameter of the structure 412 is greater than the lid aperture or greater than the corneal diameter, the upper lid may not strike the upper edge of the contact device 402 at the beginning of a blink.

The movement of the contact device 402 terminates approximately at the corneo-scleral junction due to a slope change of about 13 degrees in the area of intersection between cornea (radius of 9 mm) and sclera (radius of 11.5 mm). At this point the contact device 402, either with a rigid or soft structure 412, remains immobile and steady while the eye lid proceeds to cover it entirely.

When a rigid structure 412 is used, the contact device 402 is usually pushed down 0.5 mm to 2 mm before it comes to rest. When a soft structure 412 is used, the contact device 402 is typically pushed down 0.5 mm or less before it comes to rest. The larger the diameter of the contact device 402, the smaller the motion, and when the diameter is large enough there may be zero vertical motion. Despite these differences in motion, the squeezing effect is always present, thereby allowing accurate measurements to be taken regardless of the size of the structure 412. Use of a thicker structure 412 or one with a flatter surface results in an increased squeezing force on the contact device 402.

The eye lid margin makes a re-entrant angle of about 35 degrees with respect to the cornea. A combination of forces, possibly caused by the contraction of the muscle of Riolan near the rim of the eye lid and of the orbicularis muscle, are applied to the contact device 402 by the eye lid. A horizontal force (normal force component) of approximately 20,000 to 25,000 dynes and a vertical force (tangential force component) of about 40 to 50 dynes is applied on the contact device 402 by the upper eye lid. In response to these forces, the contact device 402 moves both toward the eye and tangentially with respect thereto. At the moment of maximum closure of the eye, the tangential motion and force are zero and the normal force and motion are at a maximum.

The horizontal lid force of 20,000 to 25,000 dynes pressing the contact device 402 against the eye generates enough motion to activate the transducer 400 mounted in the contact device 402 and to permit measurements to be performed. This eye lid force and motion toward the surface of the eye are also capable of sufficiently deforming many types of transducers or electrodes which can be mounted in the contact device 402. During blinking, the eye lids are in full contact with the contact device 402 and the surface of each transducer 400 is in contact with the cornea/tear film and/or inner surface of the eye lid.

The microminiature pressure-sensitive radio frequency transducer 400 preferably consists of an endoradiosonde mounted in the contact device 402 which, in turn, is preferably placed on the cornea and is activated by eye lid motion and/or closure. The force exerted by the eye lid on the contact device 402, as indicated above, presses it against the cornea.

Figure 26:
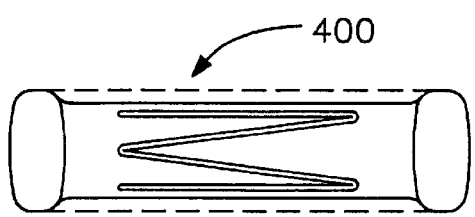
FIG. 26 is a cross-sectional view illustrating the pressure transducer of FIG. 25.

According to a preferred alternative embodiment illustrated in FIG. 26, the endoradiosonde includes two opposed matched coils which are placed within a small pellet. The flat walls of the pellet act as diaphragms and are attached one to each coil such that compression of the diaphragm by the eye lid brings the coils closer to one another. Since the coils are very close to each other, minimal changes in their separation affect their resonant frequency.

A remote grid-dip oscillator 414 may be mounted at any convenient location near the contact device 402, for example, on a hat or cap worn by the patient. The remote grid-dip oscillator 414 is used to induce oscillations in the transducer 400. The resonant frequency of these oscillations is indicative of intraocular pressure.

Briefly, the contact of the eye lid with the diaphragms forces a pair of parallel coaxial archimedean-spiral coils in the transducer 400 to move closer together. The coils constitute a high-capacitance distributed resonant circuit having a resonant frequency that varies according to relative coil spacing. When the coils approach one another, there is an increase in the capacitance and mutual inductance, thereby lowering the resonant frequency of the configuration. By repeatedly scanning the frequency of an external inductively coupled oscillating detector of the grid-dip type, the electromagnetic energy which is absorbed by the transducer 400 at its resonance is sensed through the intervening eye lid tissue.

Pressure information from the transducer 400 is preferably transmitted by radio link telemetry. Telemetry is a preferred method since it can reduce electrical noise pickup and eliminates electric shock hazards. FM (frequency modulation) methods of transmission are preferred since FM transmission is less noisy and requires less gain in the modulation amplifier, thus requiring less power for a given transmission strength. FM is also less sensitive to variations in amplitude of the transmitted signal.

Several other means and transducers can be used to acquire a signal indicative of intraocular pressure from the contact device 402. For example, active telemetry using transducers which are energized by batteries or using cells that can be recharged in the eye by an external oscillator, and active transmitters which can be powered from a biologic source can also be used.

The preferred method to acquire the signal, however, involves at least one of the aforementioned passive pressure sensitive transducers 400 which contain no internal power source and operate using energy supplied from an external source to modify the frequency emitted by the external source. Signals indicative of intraocular ocular pressure are based on the frequency modification and are transmitted to remote extra-ocular radio frequency monitors. The resonant frequency of the circuit can be remotely sensed, for example, by a grid-dip meter.

In particular, the grip-dip meter includes the aforementioned receiver 404 in which the resonant frequency of the transducer 400 can be measured after being detected by external induction coils 415 mounted near the eye, for example, in the eyeglass frames near the receiver or in the portion of the eyeglass frames which surround the eye. The use of eyeglass frames is especially practical in that the distance between the external induction coils 415 and the radiosonde is within the typical working limits thereof. It is understood, however, that the external induction coils 415, which essentially serve as a receiving antenna for the receiver 404 can be located any place that minimizes signal attenuation. The signal from the external induction coils 415

(or receiving antenna) is then received by the receiver 404 for amplification and analysis.

When under water, the signal may be transmitted using modulated sound signals because sound is less attenuated by water than are radio waves. The sonic resonators can be made responsive to changes in temperature and voltage.

Although the foregoing description includes some preferred methods and devices in accordance with the alternative embodiment of the present invention, it is understood that the invention is not limited to these preferred devices and methods. For example, many other types of miniature pressure sensitive radio transmitters can be used and mounted in the contact device, and any microminiature pressure sensor that modulates a signal from a radio transmitter and sends the modulated signal to a nearby radio receiver can be used.

Other devices such as strain gauges, preferably piezoelectric pressure transducers, can also be used on the cornea and are preferably activated by eye lid closure and blinking. Any displacement transducer contained in a distensible case also can be mounted in the contact device. In fact, many types of pressure transducers can be mounted in and used by the contact device. Naturally, virtually any transducer that can translate the mechanical deformation into electric signals is usable.

Since the eye changes its temperature in response to changes in pressure, a pressure-sensitive transducer which does not require motion of the parts can also be used, such as a thermistor. Alternatively, the dielectric constant of the eye, which also changes in response to pressure changes, can be evaluated to determine intraocular pressure. In this case, a pressure-sensitive capacitor can be used. Piezoelectric and piezo-resistive transducers, silicon strain gauges, semiconductor devices and the like can also be mounted and activated by blinking and/or closure of the eyes.

In addition to providing a novel method for performing single measurements, continuous measurements, and self-measurement of intraocular pressure during blinking or with the eyes closed, the apparatus can also be used to measure outflow facility and other physiological parameters. The inventive method and device offer a unique approach to measuring outflow facility in a physiological manner and undisturbed by the placement of an external weight on the eye.

In order to determine outflow facility in this fashion, it is necessary for the eye lid to create the excess force necessary to squeeze fluid out of the eye. Because the present invention permits measurement of pressure with the patient's eyes closed, the eye lids can remain closed throughout the procedure and measurements can be taken concomitantly. In particular, this is accomplished by forcefully squeezing the eye lids shut. Pressures of about 60 mm Hg will occur, which is enough to squeeze fluid out of the eye and thus evaluate outflow facility. The intraocular pressure will decrease over time and the decay in pressure with respect to time correlates to the outflow facility. In normal individuals, the intraocular fluid is forced out of the eye with the forceful closure of the eye lid and the pressure will decrease accordingly; however, in patients with glaucoma, the outflow is compromised and the eye pressure therefore does not decrease at the same rate in response to the forceful closure of the eye lids. The present system allows real time and continuous measurement of eye pressure and, since the signal can be transmitted through the eye lid to an external receiver, the eyes can remain closed throughout the procedure.

Telemetry systems for measuring pressure, electrical changes, dimensions, acceleration, flow, temperature, bioelectric activity, chemical reactions, and other important physiological parameters and power switches to externally control the system can be used in the apparatus of the invention. The use of integrated circuits and technical advances occurring in transducer, power source, and signal processing technology allow for extreme miniaturization of the components which, in turn, permits several sensors to be mounted in one contact device, as illustrated for example in FIG. 28.

Figure 31:
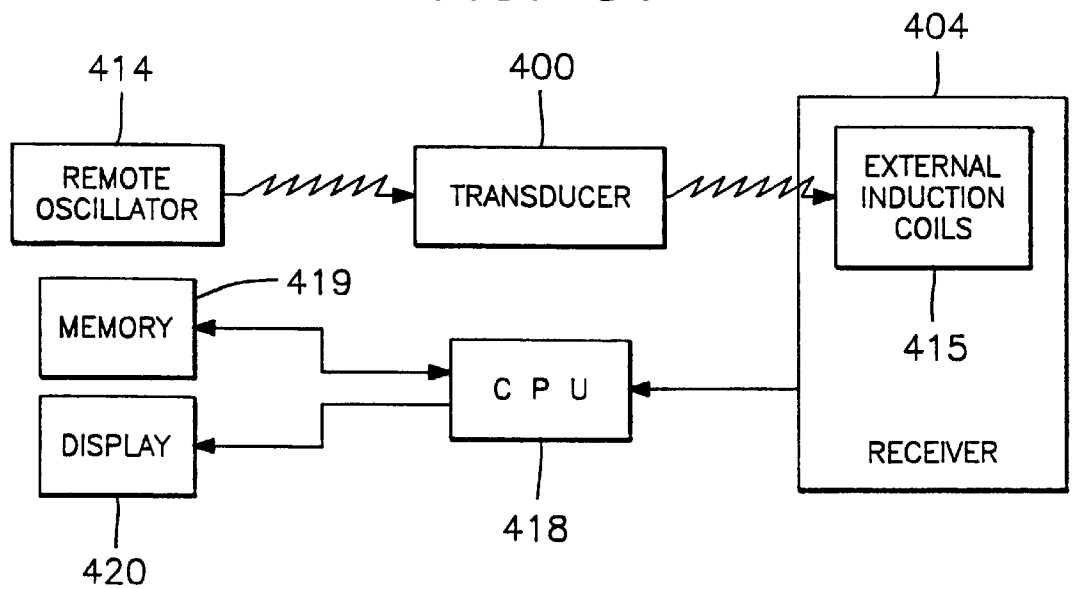
FIG. 31 is a block diagram of a preferred circuit defined by the alternative embodiment illustrated in FIG. 25.

Modern resolutions of integrated circuits are in the order of a few microns and facilitate the creation of very high density circuit arrangements. Preferably, the modern techniques of manufacturing integrated circuits are exploited in order to make electronic components small enough for placement on the eyeglass frame 408. The receiver 404, for example, may be connected to various miniature electronic components 418, 419, 420, as schematically illustrated in FIG. 31, capable of processing, storing, and even displaying the information derived from the transducer 400.

Radio frequency and ultrasonic micro-circuits are available and can be mounted in the contact device for use thereby. A number of different ultrasonic and pressure transducers are also available and can be used and mounted in the contact device. It is understood that further technological advances will occur which will permit further applications of the apparatus of the invention.

The system may further comprise a contact device for placement on the cornea and having a transducer capable of detecting chemical changes in the tear film. The system may further include a contact device for placement on the cornea and having a microminiature gas-sensitive radio frequency transducer (e.g., oxygen-sensitive). A contact device having a microminiature blood velocity-sensitive radio frequency transducer may also be used for mounting on the conjunctiva and is preferably activated by eye lid motion and/or closure of the eye lid.

The system also may comprise a contact device in which a radio frequency transducer capable or measuring the negative resistance of nerve fibers is mounted in the contact device which, in turn, is placed on the cornea and is preferably activated by eye lid motion and/or closure of the eye lid. By measuring the electrical resistance, the effects of microorganisms, drugs, poisons and anesthetics can be evaluated.

The system of the present invention may also include a contact device in which a microminiature radiation-sensitive radio frequency transducer is mounted in the contact device which, in turn, is placed on the cornea and is preferably activated by eye lid motion and/or closure of the eye lid.

In any of the foregoing embodiments having a transducer mounted in the contact device, a grid-dip meter can be used to measure the frequency characteristics of the tuned circuit defined by the transducer.

Besides using passive telemetry techniques as illustrated by the use of the above transducers, active telemetry with active transmitters and a microminiature battery mounted in the contact device can also be used.

The contact device preferably includes a rigid or flexible transparent structure 412 in which at least one of the transducers 400 is mounted in hole(s) formed in the transparent structure 412. Preferably, the transducers 400 is/are positioned so as to allow the passage of light through the visual axis. The structure 412 preferably includes an inner concave surface shaped to match an outer surface of the cornea.

Figure 29:
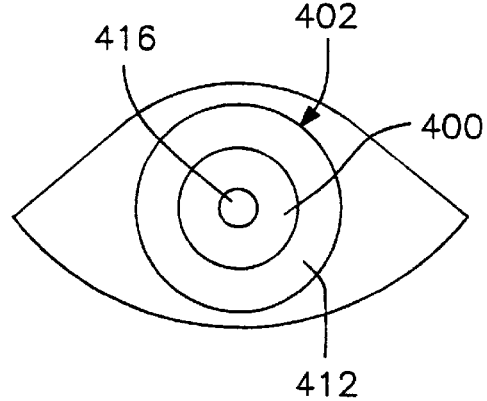
FIG. 29 illustrates an alternative embodiment utilizing a centrally disposed pressure transducer.
Figure 30:
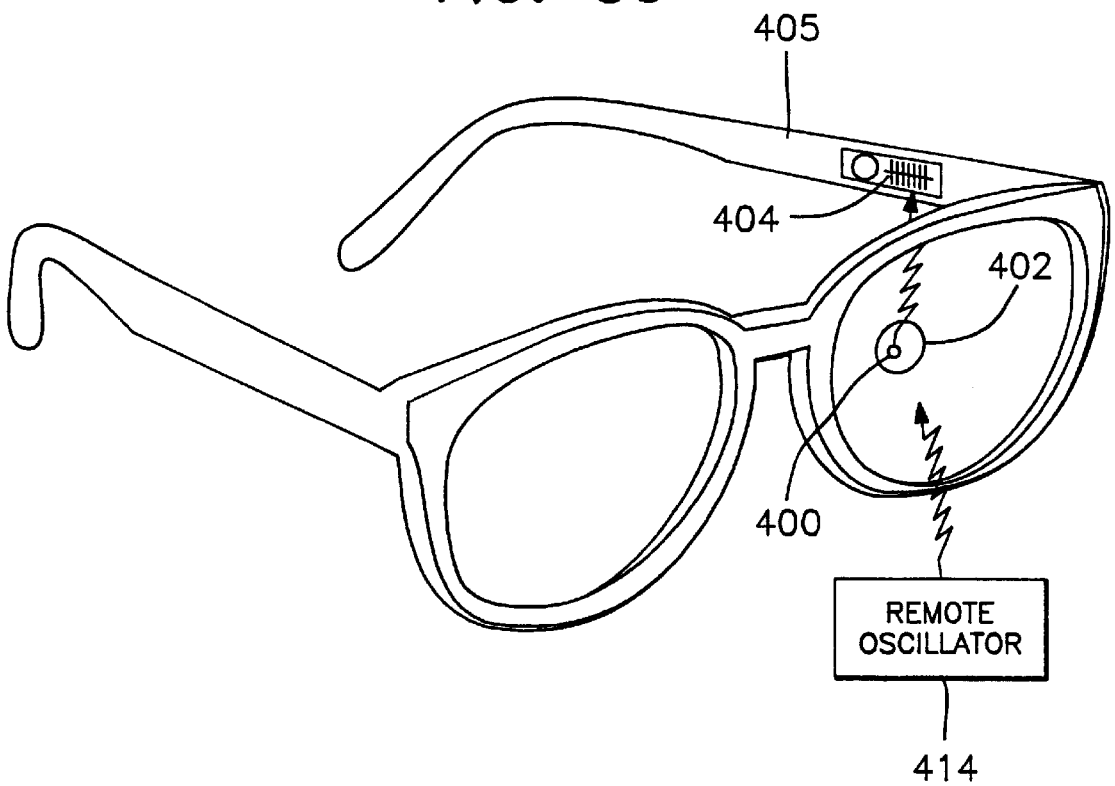
FIG. 30 illustrates a preferred mounting of the alternative embodiment to eye glass frames.

As illustrated in FIG. 29, a larger transducer 400 can be centrally arranged in the contact device 402, with a transparent portion 416 therein preserving the visual axis of the contact device 402.

The structure 412 preferably has a maximum thickness at the center and a progressively decreasing thickness toward a periphery of the structure 412. The transducers is/are preferably secured to the structure 412 so that the anterior side of each transducer 400 is in contact with the inner surface of the eye lid during blinking and so that the posterior side of each transducer 400 is in contact with the cornea, thus allowing eye lid motion to squeeze the contact device 402 and its associated transducers 400 against the cornea.

Preferably, each transducer 400 is fixed to the structure 412 in such a way that only the diaphragms of the transducers experience motion in response to pressure changes. The transducers 400 may also have any suitable thickness, including matching or going beyond the surface of the structure 412.

The transducers 400 may also be positioned so as to bear against only the cornea or alternatively only against the inner surface of the eye lid. The transducers 400 may also be positioned in a protruding way toward the cornea in such a way that the posterior part flattens a portion of the cornea upon eye lid closure. Similarly, the transducers 400 may also be positioned in a protruding way toward the inner surface of the eye lid so that the anterior part of the transducer 400 is pressed by the eye lid, with the posterior part being covered by a flexible membrane allowing interaction with the cornea upon eye lid closure.

Figure 28:
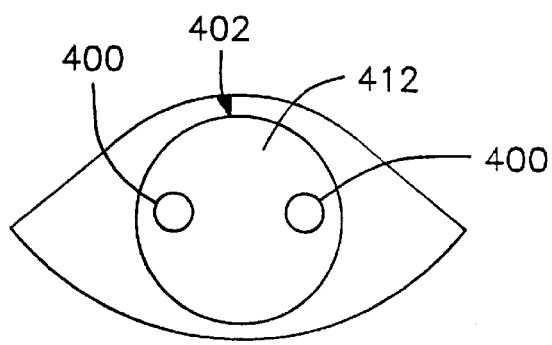
FIG. 28 illustrates an alternative embodiment wherein two pressure transducers are utilized.

A flexible membrane of the type used in flexible or hydrogel lenses may encase the contact device 402 for comfort as long as it does not interfere with signal acquisition and transmission. Although the transducers 400 can be positioned in a manner to counterbalance each other, as illustrated in FIG. 28, it is understood that a counter weight can be used to maintain proper balance.

Figure 32:
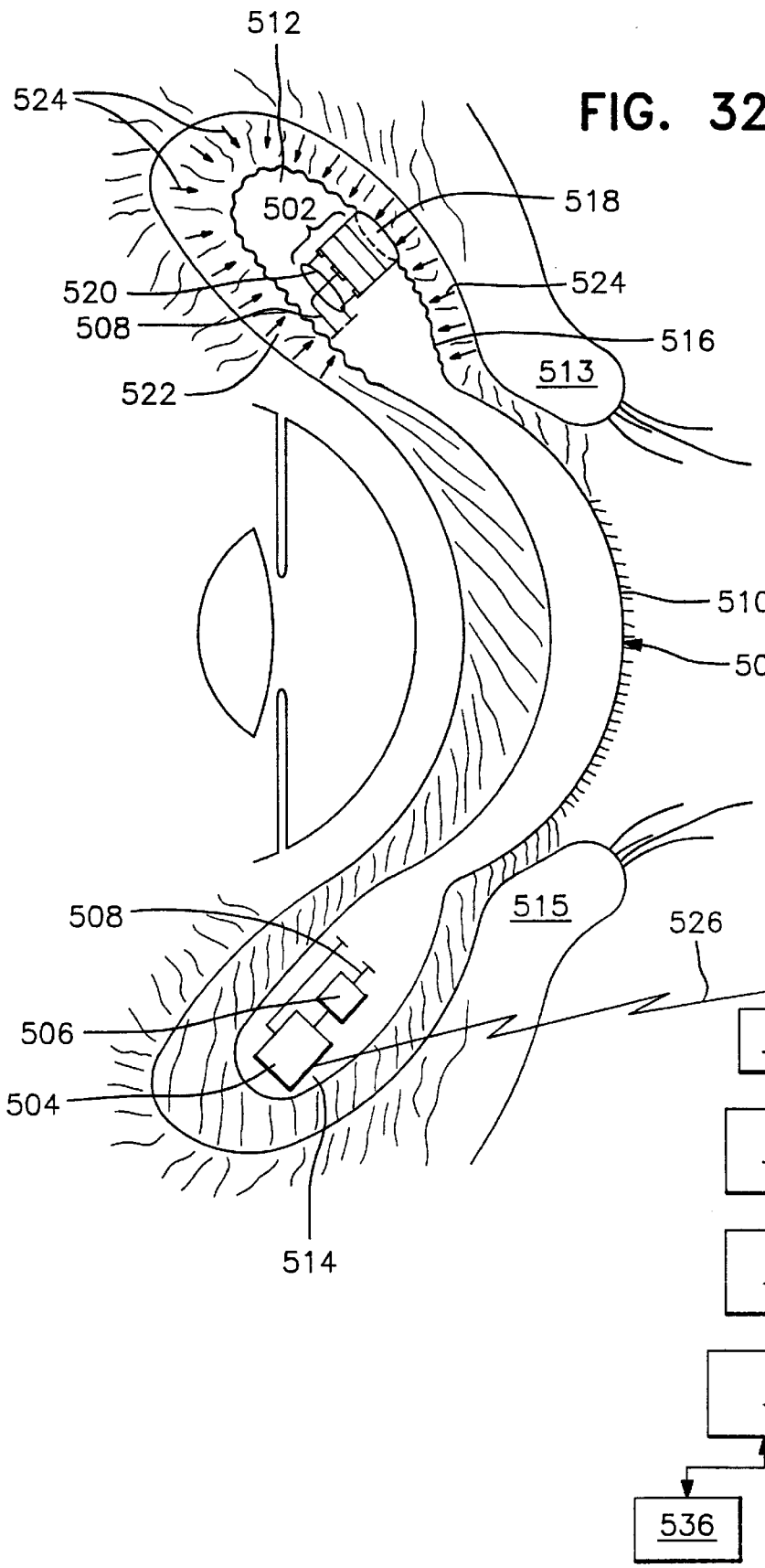
FIG. 32 is a schematic representation of a contact device situated on the cornea of an eye with lateral extensions of the contact device extending into the sclera sack below the upper and lower eye lids and illustrating schematically the reception of a signal transmitted from a transmitter to a receiver and the processes performed on the transmitted signal.

FIG. 32 illustrates the contact device 500 placed on the surface of the eye with mounted sensor 502, transmitter 504, and power source 506 which are connected by fine wire 508 (shown only partially extending from sensor 502 and from transmitter 504), encased in the contact device. The contact device shown measures approximately 24 mm in its largest diameter with its corneal portion 510 measuring approximately 11 mm in diameter with the remaining 13 mm subdivided between 8 mm of a portion 512 under the upper eyelid 513 and 5 mm of a portion 514 under the lower eyelid 515. The contact device in FIG. 32 has microprotuberances 516 in its surface which increases friction and adhesion to the conjunctiva allowing diffusion of tissue fluid from the blood vessels into the sensor selective membrane surface 518. The tissue fluid goes through membranes in the sensor and reaches an electrode 520 with generation of current proportional to the amount of analyte found in the tear fluid 522 moving in the direction of arrows 524. A transmitter 504 transmitting a modulated signal 526 to a receiver 528 with the signal 526 being amplified and filtered in amplifier and filter 529, decoded in demultiplexer 530, processed in CPU 532, displayed at monitor 534, and stored in memory 536.

Figure 33C:
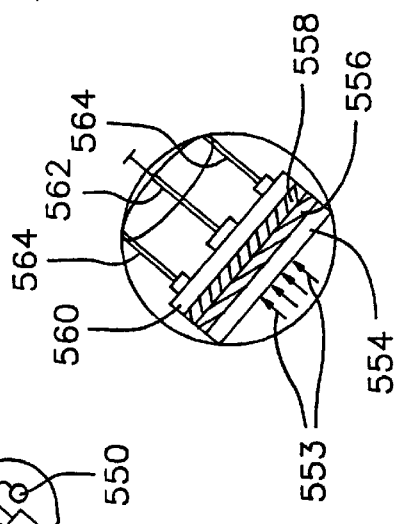
FIG. 33A is an enlarged view of the contact device shown in FIG. 32 with further enlarged portions of the contact device encircled in FIG. 33A being shown in further detail in FIGS. 33B and 33C.
Figure 33A:
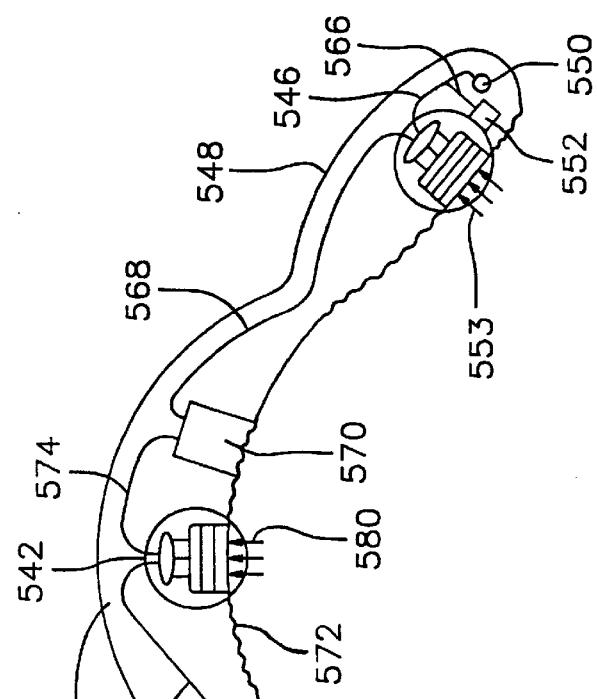

The contact device 540 shown in FIG. 33A includes two sensors, one sensor 542 for detection of glucose located in the main body 544 of the contact device and a cholesterol sensor 546 located on a myoflange 548 of the contact device 540. Forming part of the contact device is a heating electrode 550 and a power source 552 next to the cholesterol sensor 546 with the heating electrode 550 increasing the local temperature with subsequent transudation of fluid in the direction of arrows 553 toward the cholesterol sensor 546.

In one embodiment the cholesterol sensor shown in FIG. 33C includes an outer selectively permeable membrane 554, and mid-membranes 556, 558 with immobilized cholesterol esterase and cholesterol oxidase enzymes and an inner membrane 560 permeable to hydrogen peroxide. The external membrane 554 surface has an area preferably no greater than 300 square micrometers and an overall thickness of the multiple membrane layers is in the order of 30–40 micrometers. Covered by the inner membrane are a platinum electrode 562 and two silver electrodes 564 measuring 0.4 mm (platinum wire) and 0.15 mm (silver wire). Fine wires 566, 568 connect the cholesterol sensor 546 to the power source 552 and transmitter 570. The glucose sensor 542 includes a surrounding irregular external surface 572 to increase friction with the sensor connected by fine wires 574, 576 to the power source 578 and transmitter 570. The power source 578 is connected to the sensor in order to power the sensor 542 for operation.

The transmitter includes integrated circuits for receiving and transmitting the data with the transmitters being of ultra dense integrated hybrid circuits measuring approximately 500 microns in its largest dimension. The corneal tissue fluid diffuses in the direction of arrows 580 toward the glucose sensor 542 and reaches an outer membrane 582 permeable to glucose and oxygen followed by an immobilized glucose oxidase membrane 584 and an inner membrane 586 permeable to hydrogen peroxide. The tissue fluid then reaches the one platinum 588 and two silver 590 electrodes generating a current proportional to the concentration of glucose. The dimensions of the glucose sensor are similar to the dimensions of the cholesterol sensor.

Figure 33B:
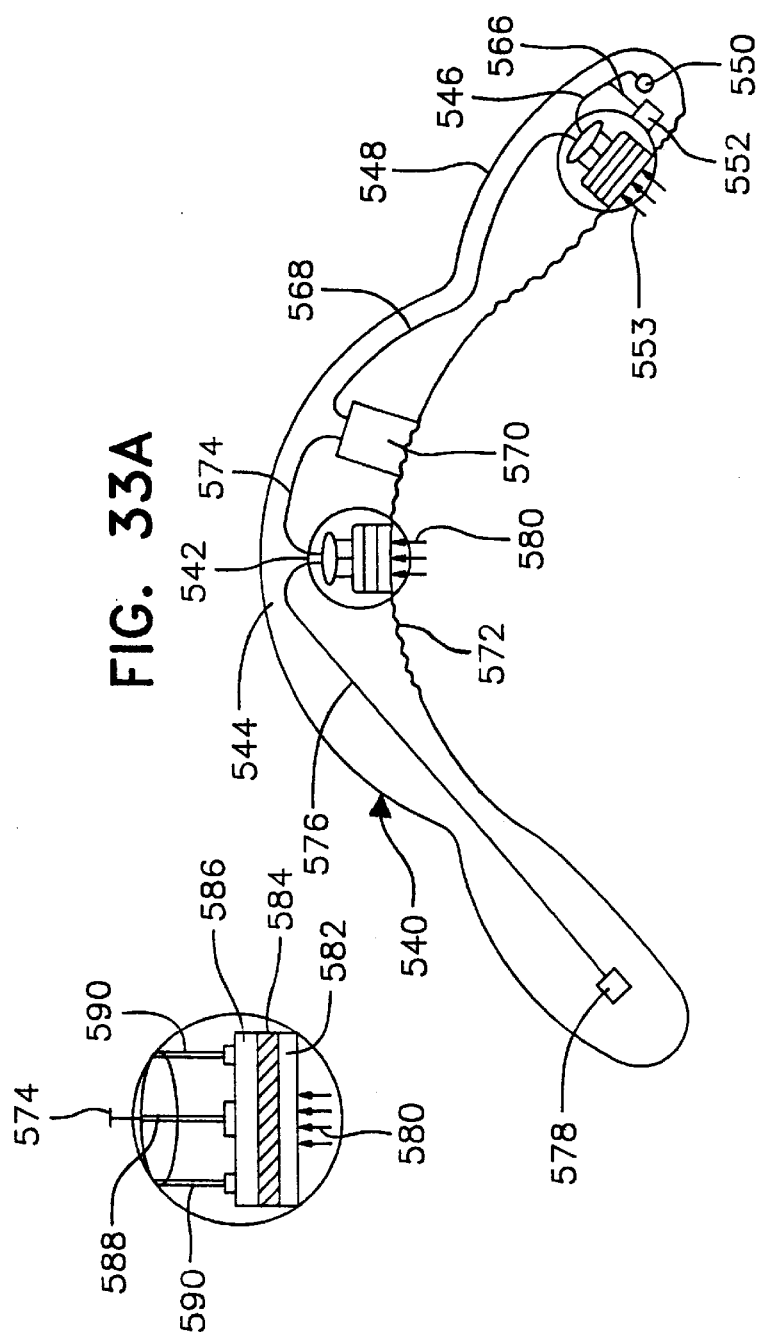
Figure 34:
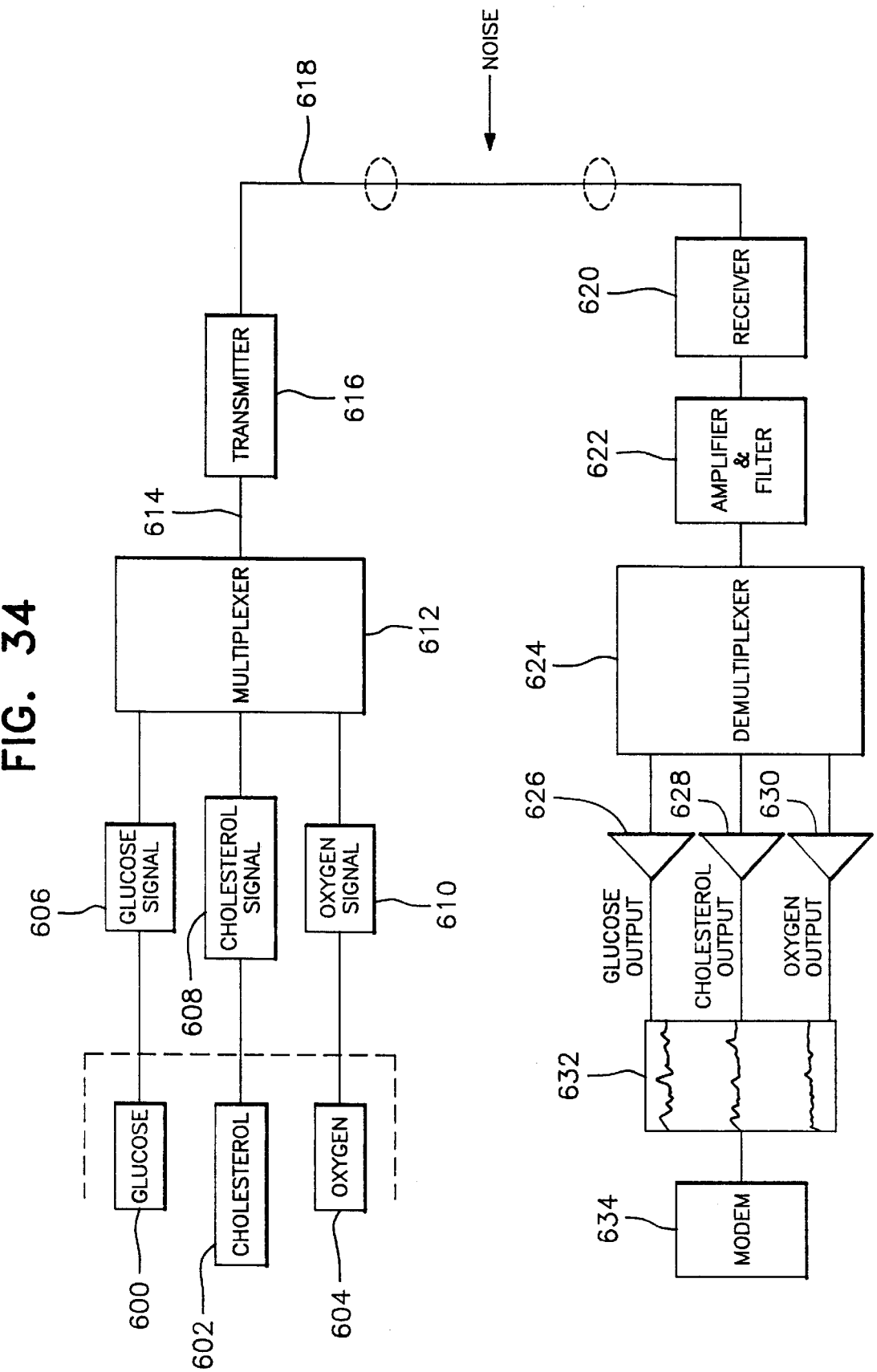
FIG. 34 is a schematic block diagram of a system of obtaining sample signal measurements and transmitting and interpreting the results of the sample signals.

FIG. 34 illustrates by, a block diagram, examples of signals obtained for measuring various biological variables such as glucose 600, cholesterol 602 and oxygen 604 in the manner as exemplified in FIGS. 33A–33C. A glucose signal 606, a cholesterol signal 608 and an oxygen signal 610 are generated by transducers or sensors as shown in FIGS. 33B and 33C. The signals are transmitted to a multiplexer 612 which transmits the signals as a coded signal by wire 614 to a transmitter 616. A coded and modulated signal is transmitted, as represented by line 618, by radio, light, sound, wire telephone or the like with noise suppression to a receiver 620. The signal is then amplified and filtered at amplifier and filter 622. The signal passes through a demultiplexer 624 and the separated signals are amplified at 626, 628, 630, respectively and transmitted and displayed at display 632 of a CPU and recorded for transmission by modem 634 to a hospital network, for example.

Figure 35A:
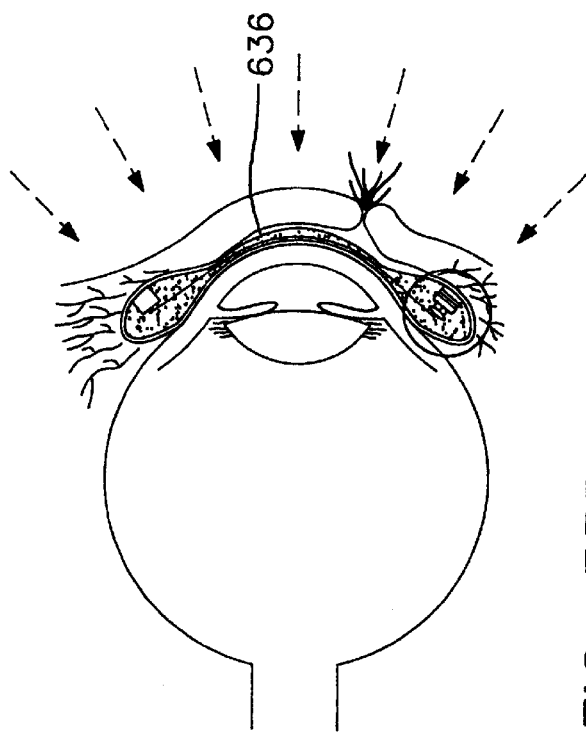
FIGS. 35A and 35C schematically represent the actuation of the contact device of the present invention by the opening and closing of the eye lids.
Figure 35B:
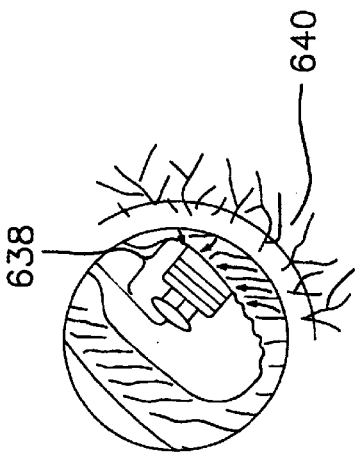
FIG. 35B is an enlarged detail view of an area encircled in FIG. 35A.
Figure 35C:
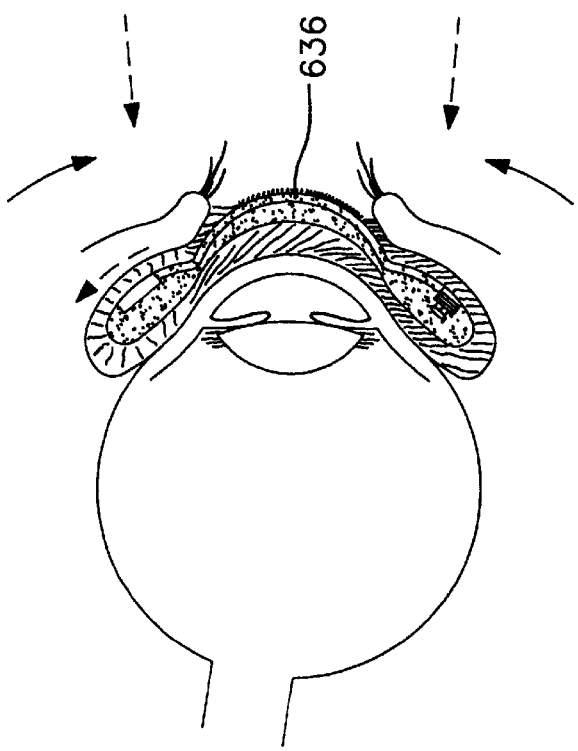

FIGS. 35A–35C illustrate an intelligent contact lens being activated by closure of the eyelids with subsequent increased diffusion of blood components to the sensor. During movement of the eye lids from the position shown in FIG. 35C to the position shown in FIG. 35A by blinking and/or closure of the eye, a combination of forces are applied to the contact device 636 by the eyelid with a horizontal force (normal force component) of approximately 25,000 dynes which causes an intimate interaction between the contact device and the surface of the eye with a disruption of the lipid layer of the tear film allowing direct interaction of the outer surface of the contact device with the palpebral conjunctiva as well as a direct interaction of the inner surface of the contact device with the aqueous layer of the tear film and the epithelial surface of the cornea and bulbar conjunctiva. Blinking promotes a pump system which extracts fluid from the supero-temporal corner of the eye and delivery of fluid to the puncta in the infero-medial corner of the eye creating a continuous flow which bathes the contact device. During blinking, the close interaction with the palpebral conjunctiva, bulbar conjunctiva, and cornea, the slightly rugged surface of the contact device creates microdisruption of the blood barrier and of the epithelial surface with transudation and increased flow of tissue fluid toward the surface of the contact device. The tear fluid then diffuses through the selectively permeable membranes located on the surface of the contact device 636 and subsequently reaching the electrodes of the sensor 638 mounted in the contact device. In the preferred embodiment for glucose measurement, glucose and oxygen flow from the capillary vessels 640 toward a selectively permeable outer membrane and subsequently reach a mid-membrane with immobilized glucose oxidase enzyme. At this layer of immobilized glucose oxidase enzyme, an enzymatic oxidation of glucose in the presence of the enzyzme oxidase and oxygen takes place with the formation of hydrogen peroxide and gluconic acid. The hydrogen peroxide then diffuses through an inner membrane and reaches the surface of a platinum electrode and it is oxidized on the surface of the working electrode creating a measurable electrical current. The intensity of the current generated is proportional to the concentration of hydrogen peroxide which is proportional to the concentration of glucose. The electrical current is subsequently converted to a frequency audio signal by a transmitter mounted in the contact device with signals being transmitted to a remote receiver using preferably electromagnetic energy for subsequent amplification, decoding, processing, analysis, and display.

In FIGS. 36A through 36J, various shapes of contact devices are shown for use in different situations. In FIG. 36A, a contact device 642 is shown of an elliptical, banana or half moon shape for placement under the upper or lower eye lid. FIGS. 36B and 36C show a contact device 644 having, in side view a wide base portion 646 as compared to an upper portion 648. FIG. 36D shows a contact device 650 having a truncated lens portion 652.

In FIGS. 36E and 36F, the contact device 654 is shown in side view in FIG. 36E and includes a widened base portion 656 which as shown in FIG. 36F is of a semi-truncated configuration.

FIG. 36G shows a contact device 658, having a corneal portion 650 and a scleral portion 652. In FIG. 36H, an oversized contact device 664, includes a corneal portion 666 and a scleral portion 668.

A more circular shaped contact device 670 is shown in FIG. 36I having a corneal-scleral lens 672.

The contact device 674 shown in FIG. 36J is similar to the ones shown in FIGS. 32, 33A, 35A and 35C. The contact device includes a main body portion 676 with upper myoflange or minus carrier 678 and lower myoflange or minus carrier 680.

Figure 37B:
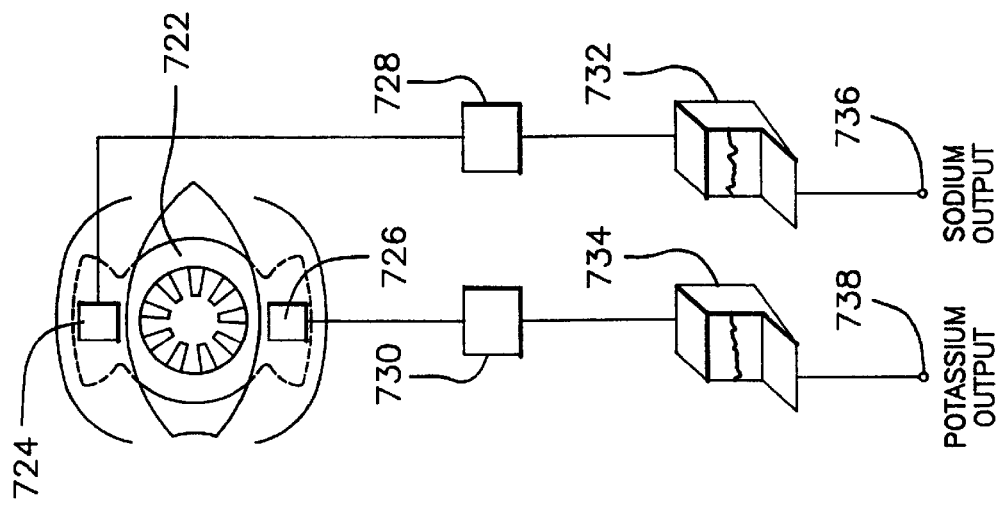
FIGS. 37A and 37B schematically illustrate interpretation of signals generated from the contact device of the present invention and the analysis of the signals to provide different test measurements and transmission of this data to remote locations, such as an intensive care unit setting.
Figure 37A:
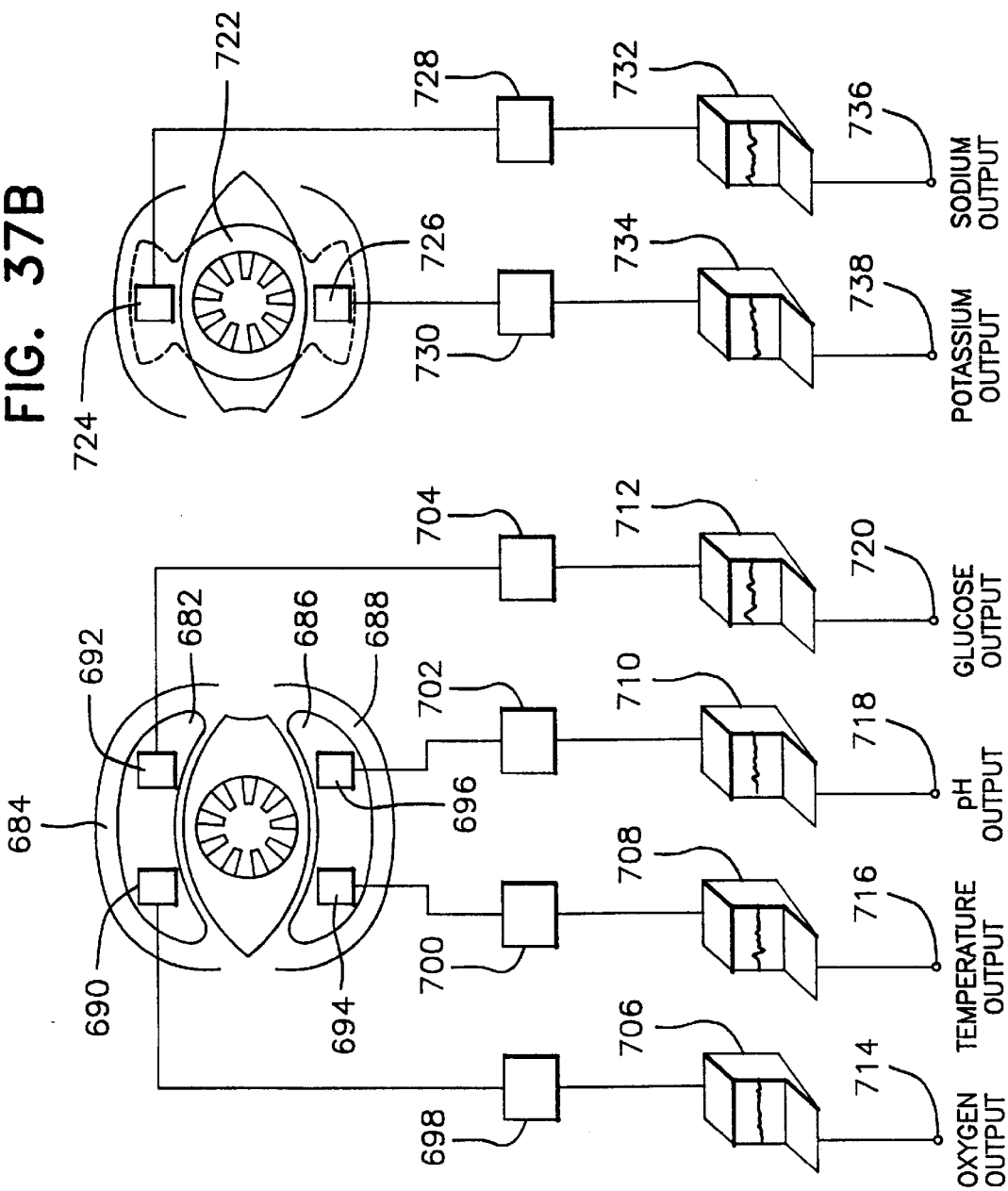

In FIG. 37A, an upper contact device 682 is placed under an upper eye lid 684. Similarly, a lower contact device 686 is placed underneath a lower eye lid 688. Upper contact device 682 includes an oxygen sensor/transmitter 690 and a glucose transmitter 692. Similarly, the lower contact device includes a temperature sensor transmitter 694 and a pH sensor/transmitter 696.

Each of these four sensors outputs a signal to respective receivers 698, 700, 702 and 704, for subsequent display in CPU displays 706, 708, 710, 712, respectively. The CPUs display an indication of a sensed oxygen output 714, temperature output 716, pH output 718 and glucose output 720.

In FIG. 37B, a single contact device 722, in an hour glass shape, includes an upper sodium sensor/transmitter 724 and a lower potassium sensor/transmitter 726. The two sensors send respective signals to receivers 728 and 730 for display in CPUs 732, 734 for providing a sodium output indicator 736 and a potassium output indicator 738.

Figure 38A:
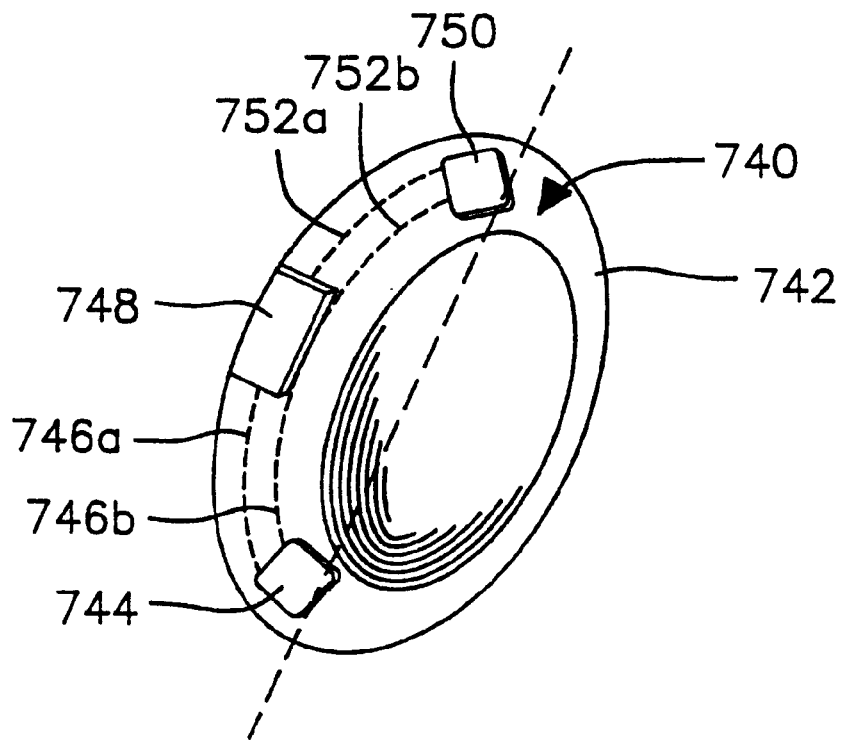
FIG. 38A schematically illustrates a contact device of the present invention with FIG. 38B being a sectional view taken along the section line shown in FIG. 38A.
Figure 38B:
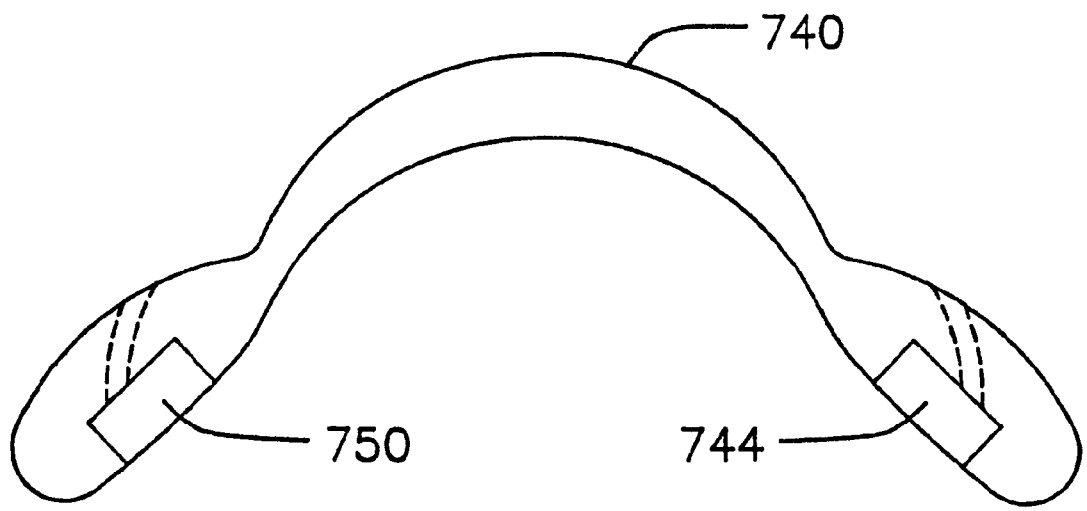

In FIG. 38A, a contact device 740 is shown which may be formed of an annular band 742 so as to have a central opening with the opening overlying a corneal portion or if the contact device includes a corneal portion, the corneal portion lays on the surface of the cornea. Limited to annular band 742 is a sensor 744 positioned on the scleral portion of the contact device so as to be positioned under an eye lid. The sensor is connected by wires 746a, 746b to transmitter 748 which is in communication with the power source 750 by wires 752a, 752b. The intelligent contact lens device 740 is shown in section in FIG. 38B with the power source 750 and sensor 744 located on opposite ends of the contact device on the scleral portion of the contact device.

FIG. 39A schematically illustrates the flow of tear fluid as illustrated by arrows 754 from the right lacrimal gland 756 across the eye to the lacrimal punctum 758a and 758. Taking advantage of the flow of tear fluid, in FIG. 39B, a contact device 760 is positioned in the lower cul-de-sac 762 beneath the lower eye lid 764 so that a plurality of sensors 764a, 764b and 764c in wire communication with a power source 766 and transducer 768 can be connected by a wire 770 to an external device. The flow of tear fluid from the left lacrimal gland 762 to the lacrimal punctum 764a and 764b is taken advantage of to produce a reading indicative of the properties to be detected by the sensors.

Figure 40A:
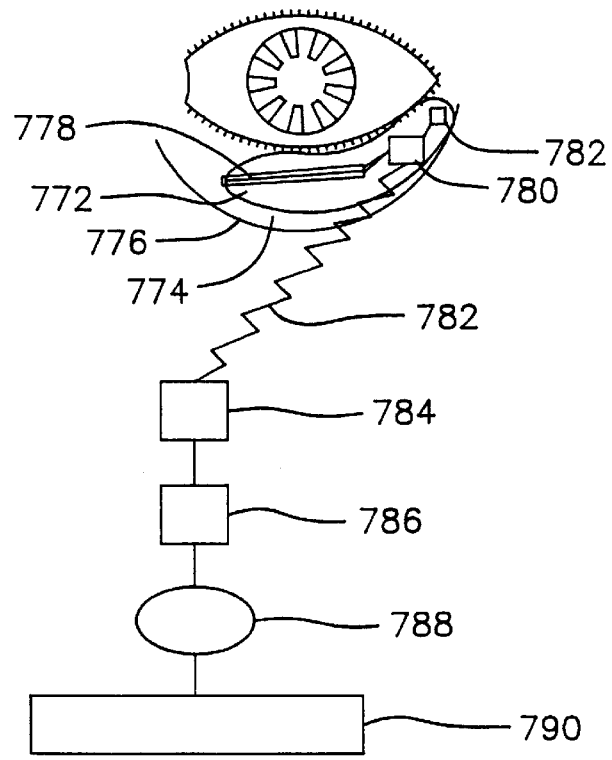
FIG. 40A schematically illustrates an alternative embodiment of the present invention, used under the eye lid to produce signals indicative of sensed glucose levels which are radio transmitted to a remote station followed by communication through a publically available network.

In FIG. 40A, a contact device 772 is positioned in the cul-de-sac 774 of the lower eye lid 776. The contact device includes a needle-type glucose sensor 778 in communication with a transmitter 780 and a power source 782. A signal 782 is transmitted to a receiver, demultiplexer and amplifier 784 for transmission to a CPU and modem 786 and subsequent transmission over a public communication network 788 for receipt and appropriate action at an interface 790 of a hospital network.

Figure 40B:
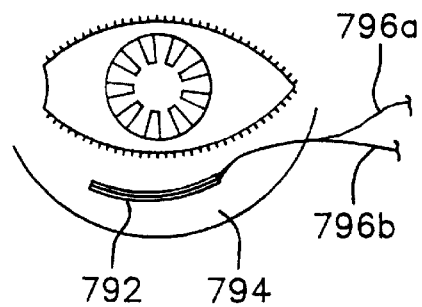
FIG. 40B schematically illustrates an alternative embodiment of the glucose sensor to be used under the eyelid with signals transmitted through wires.

In FIG. 40B, a similar arrangement to that shown in FIG. 40A is used except the glucose sensor 792 is a needle type sensor with a curved shape so as to be placed directly against the eye lid. The sensor 792 is silicone coated or encased by coating with silicone for comfortable wear under the eye lid 794. Wires 796a and 796b extend from under the eye lid and are connected to an external device. The sensor 792 is placed in direct contact with the conjunctiva with signals and power source connected by wires to external devices.

Figure 41:
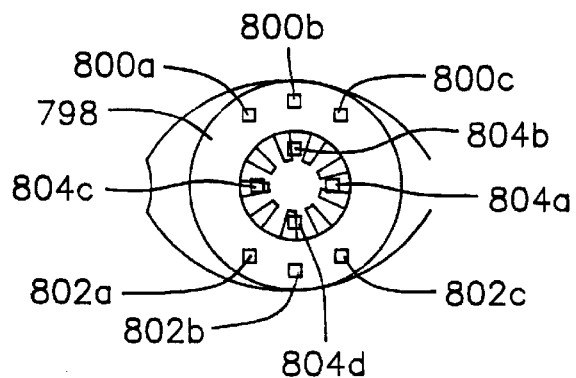
FIG. 41 illustrates an oversized contact device including a plurality of sensors.

FIG. 41 shows an oversized contact device 798 including sensors 800a, 800b, 800c and the scleral portion of the contact device to be positioned under the upper eye lid. In addition, sensors 802a, 802b, 802c are to be positioned under the lower eye lid in contact with the bulbar and/or palpebral conjunctiva. In addition, sensors 804a–d are located in the corneal portion in contact with the tear film over the cornea.

FIG. 42A shows a contact device 806 having a sensor 808 and a transmitter 810 in position, at rest, with the eye lids open. However, in FIG. 42B, when the eye lids move towards a closed position, and the individual is approaching a state of sleep, the Bell phenomenon will move the eye and therefore the contact device upward in the direction of arrows 812. The pressure produced from the eye lid as the contact device moves up, will produce a signal 814 from the sensor 808 which is transmitted to a receive 816. The signal passes through an amplifier and filter 818 to a demultiplexer 820 for activation of an alarm circuit 822 and display of data at 824. The alarm should be sufficient to wake a dozing driver or operator of other machinery to alert the user of signs of somnolence.

In FIG. 43, a heat stimulation transmission device 825 for external placement on the surface of the eye is shown for placement on the scleral and corneal portions of the eye. The device 825 includes a plurality of sensors 826 spaced across the device 825. With reference to FIG. 44, the device 825 includes heating elements 828*a–c*, a thermistor 830, an oxygen sensor 832, and a preferably inductively activated power source 834. Signals generated by the sensors are transmitted by transmitter 836 to hardware 838 which provides an output representative of a condition detected by the sensors.

In FIG. 46, an annular band 840 includes a plurality of devices 842*a–e*. The annular band shaped heat stimulation transmission device 840 can be used externally or internally by surgical implication in any part of the body promoting increase of oxygen from a remotely situated stimulating source. Another surgically implantable device 844 is shown in FIG. 46. In this example, the heat stimulation transmission device 844 is implanted between eye muscles 846, 848. Another example of a surgically implantable heat stimulation transmission device 850 is shown in FIG. 47, having four heating elements 852, a temperature sensor 854 and an oxygen sensor 856, with a power source 858 and a transmitter 860 for transmitting signal 852.

Figure 48:
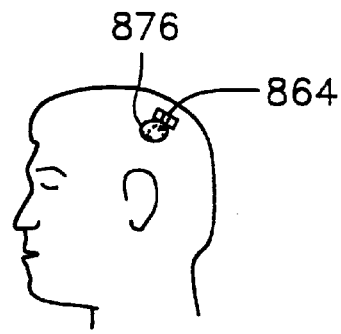
FIG. 48 schematically illustrates the surgical implantation of an overheating transmission device adjacent to a brain tumor.
Figure 49:
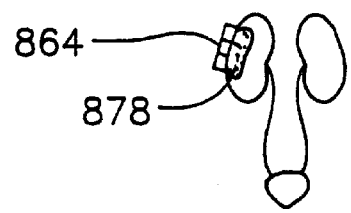
FIG. 49 illustrates the surgical implantation of an overheating transmission device adjacent to a kidney tumor.
Figure 50:
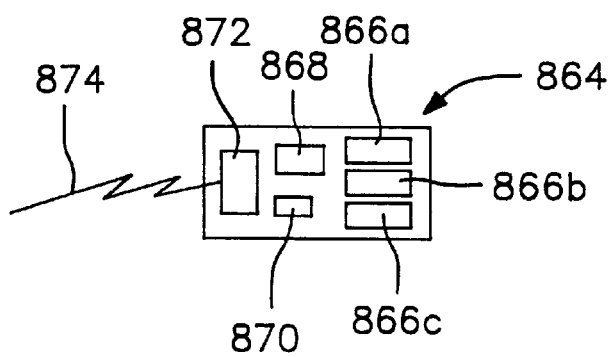
FIG. 50 illustrates an overheating transmission device and its various components.

FIGS. 48, 49 and 51 through 53 illustrate the use of an overheating transmission device, as shown in FIG. 50, for the destruction of tumor cells after the implantation of the overheating transmission device by surgery. As shown in FIG. 50, the overheating transmission device 864 includes a plurality of heating elements 866*a*, 866*b*, 866*c*, a temperature sensor 868, a power source 870 which is inductively activated and a transmitter 872 for transmitting a signal 874. By activation of the device 864, an increase in temperature results in the immediately adjacent area. This can cause the destruction of tumor cells from a remote location.

In FIG. 48, the device 864 is located adjacent to a brain tumor 876. In FIG. 49, the device 864 is located adjacent to a kidney tumor 878.

Figure 51:
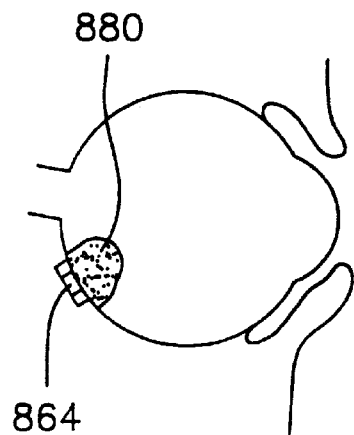
FIG. 51 illustrates the surgical implantation of an overheating transmission devices adjacent to an intraocular tumor.
Figure 52:
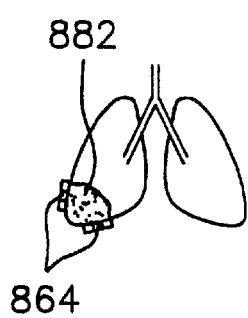
FIG. 52 schematically illustrates the surgical implantation of an overheating transmission device adjacent to a lung tumor.
Figure 53:
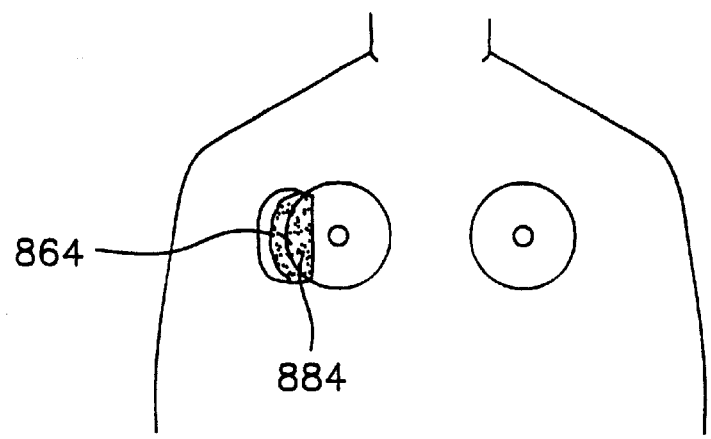
FIG. 53 schematically illustrates the positioning of an overheating transmission device adjacent to a breast tumor.

In FIG. 51, the device 864 is located adjacent to an intraocular tumor 880. In FIG. 52, a plurality of devices 864 are located adjacent to a lung tumor 882. In FIG. 53, a device 864 is located externally on the breast, adjacent to a breast tumor 884.

Figure 54A:
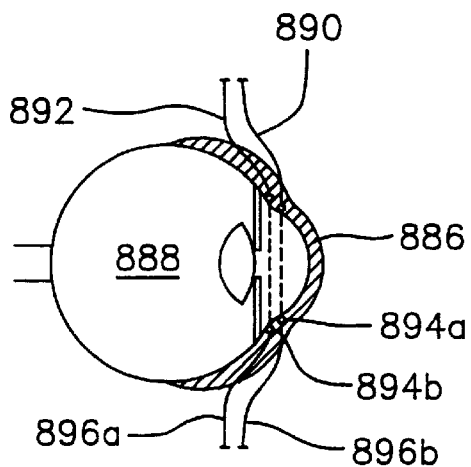
FIG. 54A is a side sectional view and FIG. 54B is a front view of a contact device used to detect chemical compounds in the aqueous humor located on the eye, with FIG. 54C being a side view thereof.
Figure 54B:
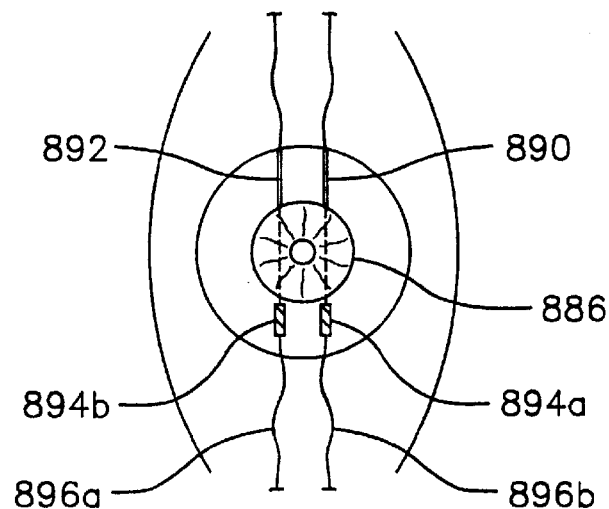

In FIGS. 54A and 54B, a contact device 886 is located on the eye 888. The contact device is used to detect glucose in the aqueous humor by emitting light from light emitting optical fiber 890, which is sensitive to glucose, as compared to a reference optical fiber light source 892, which is not sensitive to glucose. Two photo detectors 894*a*, 894*b* measure the amount of light passing from the reference optical fiber 892 and the emitting optical fiber 890 sensitive to glucose and transmit the received signals by wires 896*a*, 896*b* for analysis.

Figure 54C:
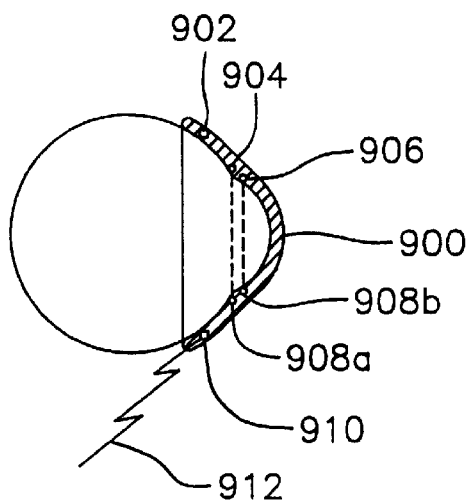

In FIG. 54C, a glucose detecting contact device 900 is used having a power source 902, an emitting light source 904 sensitive to glucose and a reference light source 906, non-sensitive to glucose. Two photo detectors 908*a* and 908*b*, provide a signal to a transmitter 910 for transmission of a signal 912 to a remote location for analysis and storage.

Figure 55A:
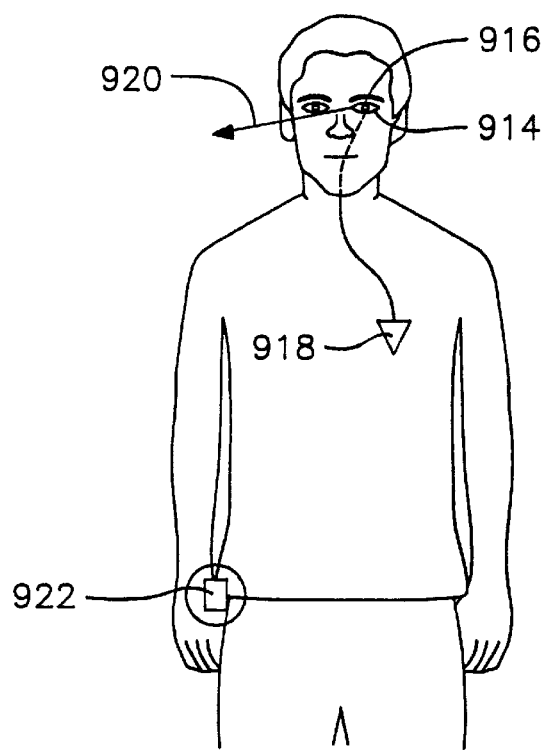
FIG. 55A schematically illustrates a microphone or motion sensor mounted on a contact device sensor positioned over the eye for detection of heart pulsations or sound and transmission of a signal representative of heart pulsations or sound to a remote alarm device with FIG. 55B being an enlarged view of the alarm device encircled in FIG. 55A.
Figure 55B:
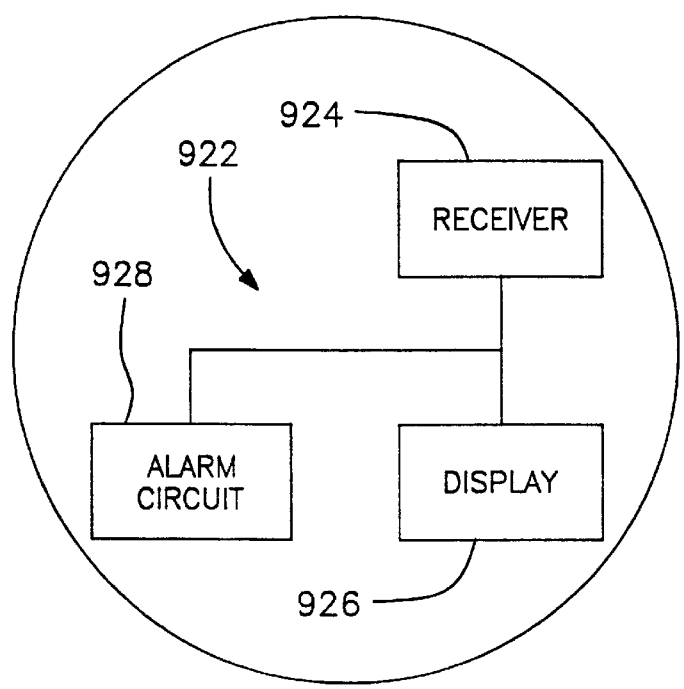

In FIG. 55A, a contact device 914 is positioned on an eye 916 for detection of heart pulsations or heart sounds as transmitted to eye 916 by the heart 918 as a normal bodily function. A transmitter provides a signal 920 indicative of the results of the heart pulsations or heart sound. A remote alarm device 922 may be worn by the individual. The details of the alarm device are shown in FIG. 55B where the receiver 924 receives the transmitted signal 920 and conveys the signal to a display device 926 as well as to an alarm circuit 928 for activation of an alarm if predetermined parameters are exceeded.

Figure 56:
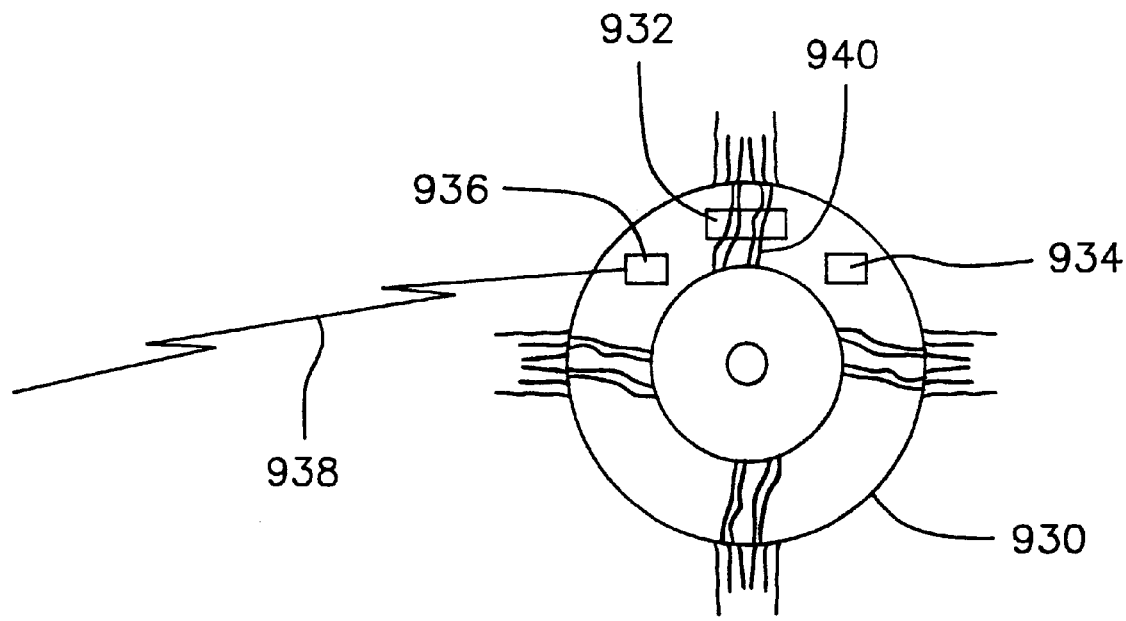
FIG. 56 illustrates a contact device with an ultrasonic dipolar sensor, power source and transmitter with the sensor located on the blood vessels of the eye.

In FIG. 56, a contact device 930 is shown. The contact device includes an ultra sound sensor 932, a power source 934 and a transmitter 936 for conveying a signal 938. The ultra sound sensor 932 is placed on a blood vessel 940 for measurement of blood flow and blood velocity. The result of this analysis is transmitted by signal 938 to a remote receiver for analysis and storage.

Figure 57:
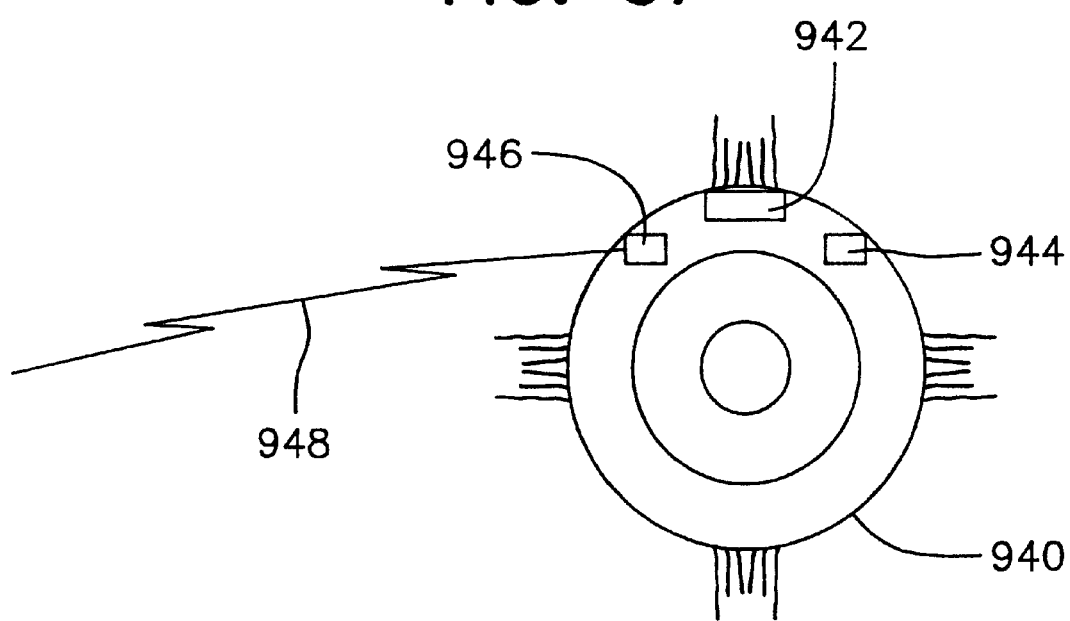
FIG. 57 schematically illustrates the location of a contact device with a sensor placed near an extraocular muscle.

In FIG. 57, an oversized contact device 940 includes a sensor 942, a power source 944 and a transmitter 946 for transmitting a signal 948. The sensor 942 is positioned on the superior rectus muscle for measurement of eye muscle potential. The measured potential is transmitted by signal 948 to a remote receiver for analysis and storage.

Figure 58A:
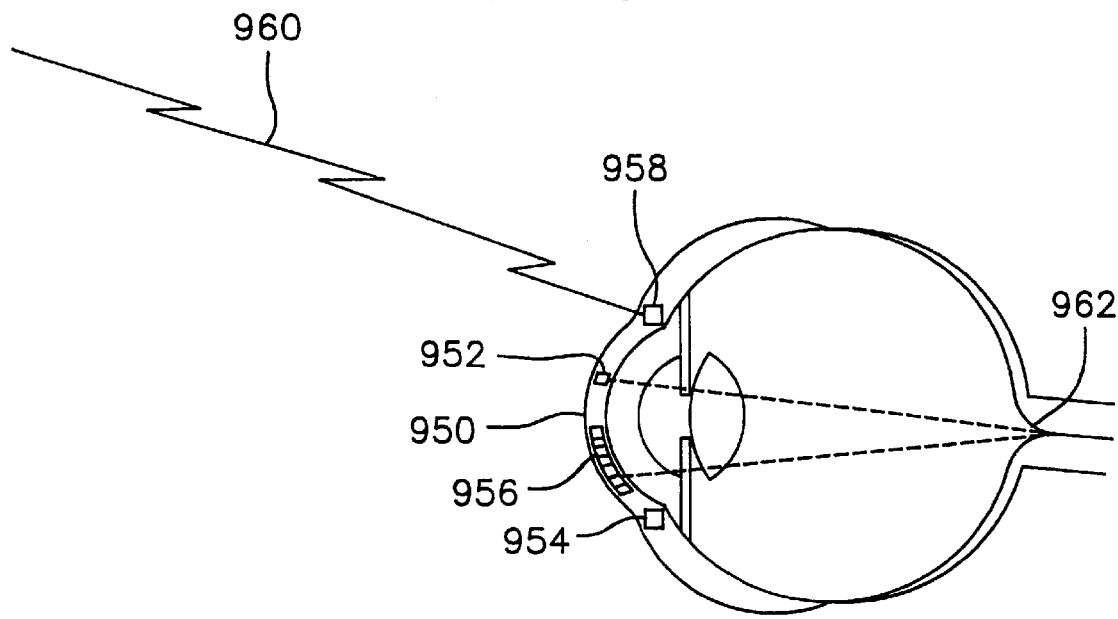
FIG. 58A is a side sectional view illustrating a contact device having a light source for illumination of the back of the eye.

In FIG. 58A, a contact device 950 includes a light source 952, a power source 954, multioptical filter system 956 and a transmitter 958 for transmission of a signal 960. The light source 952 emits a beam of light to the optic nerve head 962. The beam of light is reflected on to the multioptical filter system 956 for determination of the angle of reflection.

Figure 58B:
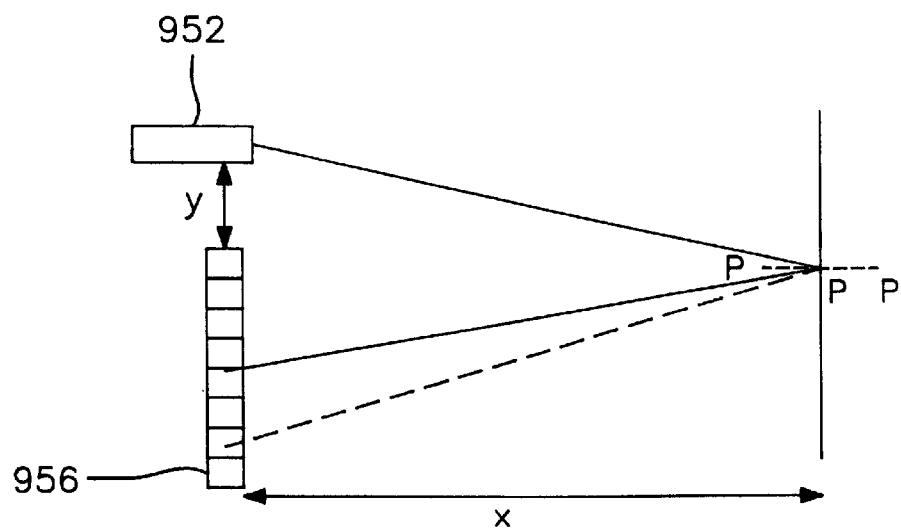
FIG. 58B illustrates schematically the transmission of light from a light source for reflection off a blood vessel at the cup of the optic nerve and for receipt of the reflected light by a multioptical filter system separated from the reflecting surface by a predetermined distance and separated from the light source by a predetermined distance for interpretation of the measurement of the reflected light.

As shown in FIG. 58B, since the distance X of separation between the multioptical filter system and the head of the optic nerve 962 remains constant as does the separation distance Y between the light source 952 and the multoptical filter system 956, a change in the point P which is representative of the head of the optic nerve will cause a consequent change in the angle of reflection so that the reflected light will reach a different point on the multioptical filter system 956. The change of the reflection point on multioptical filter system 956 will create a corresponding voltage change based on the reflection angle. The voltage signal is transmitted as an audio frequency signal 960 to a remote location for analysis and storage.

Figure 59A:
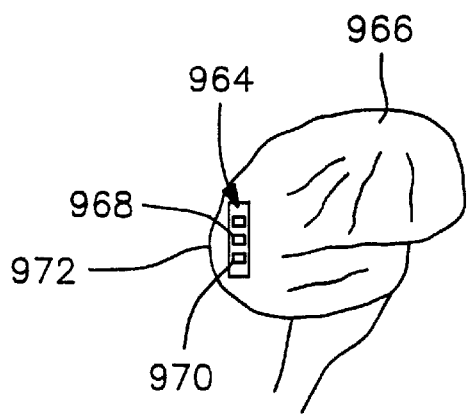
FIGS. 59A through 59C illustrate positioning of contact devices for neurostimulation of tissues in the eye and brain.
Figure 59B:
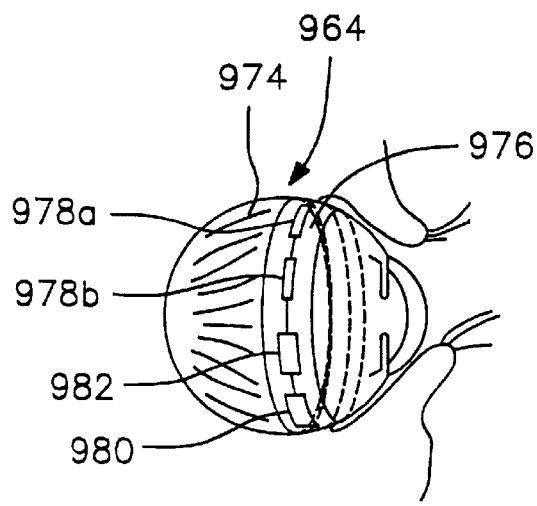
Figure 59C:
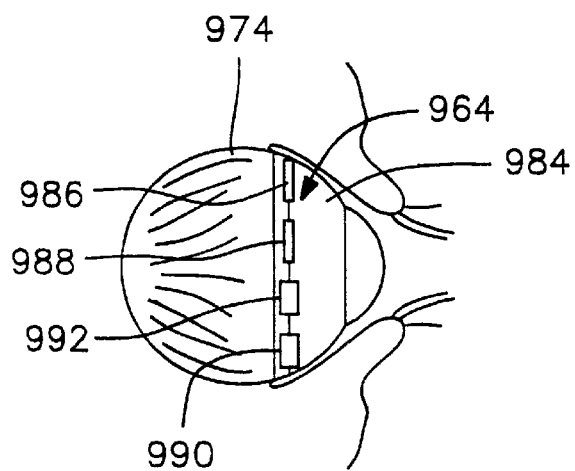

In FIGS. 59A through 59C, a neuro stimulation transmission device 964 is shown. In FIG. 59A, the device 964 is surgically implanted in the brain 966. The device 964 includes microphotodiodes or electrodes 968 and a power source/transmitter 970. The device is implanted adjacent to the occipital cortex 972.

In FIG. 59B, the device 964 is surgically implanted in the eye 974 on a band 976 including microphotodiodes 978*a*, 978*b* with a power source 980 and a transmitter 982.

In FIG. 59C, the device 964 is externally placed on the eye 974 using an oversized contact device 984 as a corneal scleral lens. The device includes an electrode 986 producing a microcurrent, a microphotodiode or electrode 988, a power source 990 and a transmitter 992 for transmission of a signal to a remote location for analysis and storage.

Figure 60:
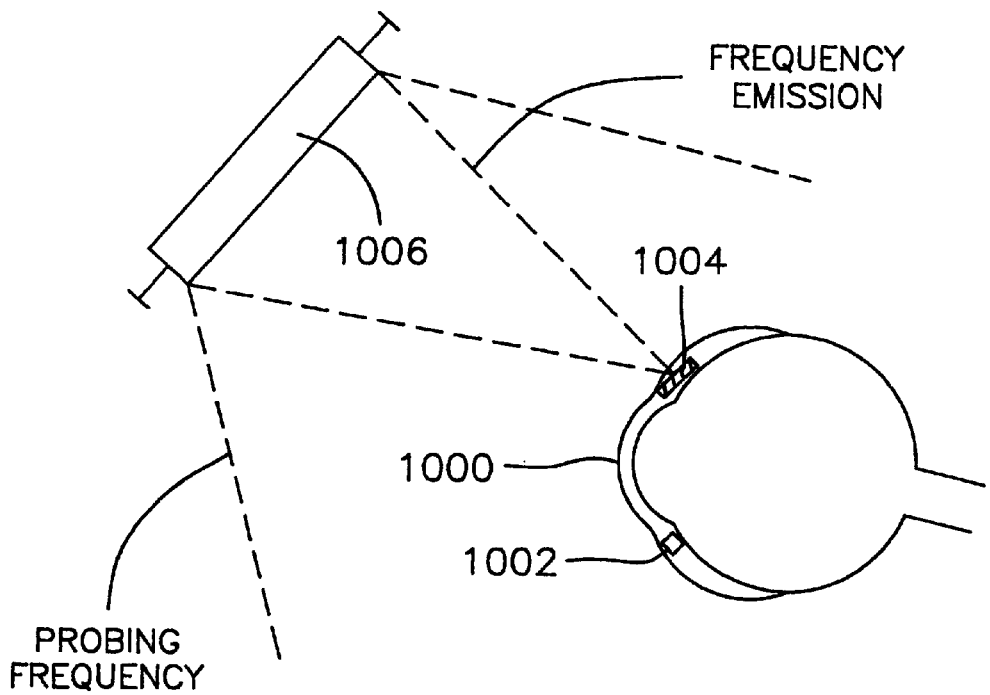
FIG. 60 is a schematic illustration of a contact device having a fixed frequency transmitter and power source for being tracked by an orbiting satellite.

In FIG. 60, a contact device 1000 includes a power source 1002 and a fixed frequency transmitter 1004. The transmitter 1004 emits a frequency which is received by an orbiting satellite 1006. Upon detection of the frequency of the signal transmitted by the transmitter 1004, the satellite can transmit a signal for remote reception indicative of the location of the transmitter 1004 and accordingly the exact location of the individual wearing the contact device 1000. This would be useful in military operations to constantly monitor the location of all personal.

Figure 61:
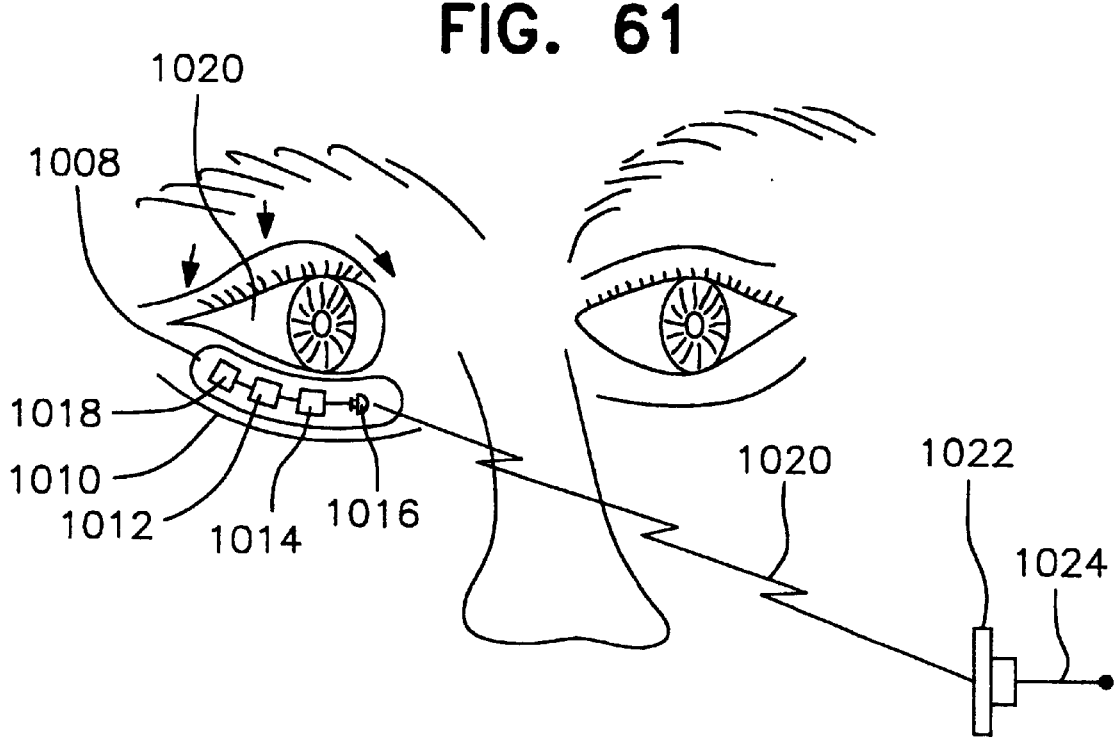
FIG. 61 illustrates a contact device under an eyelid including a pressure sensor incorporated in a circuit having a power source, an LED drive and an LED for production of an LED signal for remote activation of a device having a photodiode or optical receiver on a receptor screen.

In FIG. 61, a contact device 1008 is located below the lower eye lid 1010. The contact device includes a pressure sensor, an integrated circuit 1012, connected to an LED drive 1014 and an LED 1016. A power source 1018 is associated with the device located in the contact device 1008.

By closure of the eye 1020 by the eye lids, the pressure sensor 1012 would be activated to energize the LED drive and therefore the LED for transmission of a signal 1020 to a remote photodiode or optical receiver 1022 located on a receptor system. The photodiode or optical receiver 1022, upon receipt of the signal 1020, can transmit a signal 1024 for turning on or off a circuit. This application has may uses for those individuals limited in their body movement to only their eyes.

Figure 62:
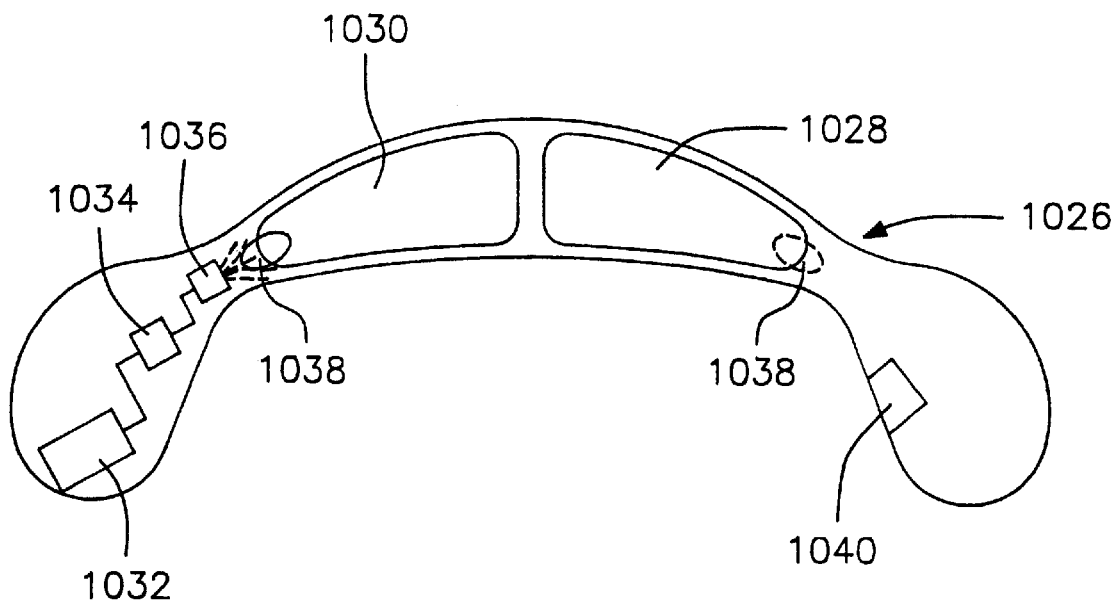
FIG. 62 is a cross-sectional view of a contact device having a drug delivery system incorporated therein.

In FIG. 62, a contact device 1026 includes compartments 1028, 1030 which include a chemical or drug which can be dispensed at the location of the contact device 1026. The sensor 1032 provides an signal indicative of a specific condition or parameter to be measured. Based upon the results of the analysis of this signal, when warranted, by logic circuit 1034, a heater device 1036 can be activated to melt a thread or other closure member 1038 sealing the compartments 1028, 1030 so as to allow release of the chemical or drug contained in the compartments 1028, 1030. The system is powered by power source 1040 based upon the biological variable signal generated as a result of measurement by sensor 1032.

Figure 63:
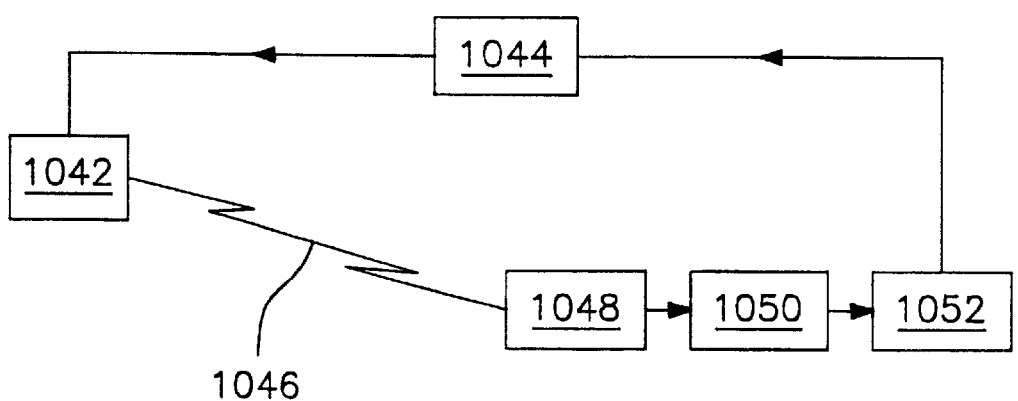
FIG. 63 schematically illustrates a block diagram of an artificial pancreas system.

According to the system shown in FIG. 63, a glucose sensor 1042, positioned on the eye 1044, can generate a glucose level signal 1046 to a receiver 1048 associated with an insulin pump 1050 for release of insulin into the blood stream 1052. The associated increase in insulin will again be measured on the eye 1044 by the sensor 1042 so as to control the amount of insulin released by the insulin pump 1050. A constant monitoring system is thereby established While the present invention has been described with reference to preferred embodiments thereof, it is understood that the present invention is not limited to those embodiments, and by the scope of the appended claims.

I claim:

1. A contact device for placement in contact with an eye, said contact device comprising:
   a contact surface for engagement with a surface of the eye,
   a sensor mounted on said contact surface, said contact surface being positionable so that eye fluids encounter said sensor, said sensor generating a signal indicative of chemical parameters of a body and the eye based upon eye fluids encountered by the sensor, said signal being transmitted externally of the eye for analysis of the signal and indication of a status of certain bodily functions,
   a signal transmitter mounted on said contact surface for transmitting said signal, and
   an energy source for powering said signal transmitter.

2. A contact device as claimed in claim 1, wherein the signal is transmitted through the air by said signal transmitter for receipt at a remote location.

3. A contact device as claimed in claim 1, wherein said sensor detects glucose levels in the eye fluid.

4. A contact device as claimed in claim 1, wherein said sensor detects cholesterol levels in the eye fluid.

5. A contact device as claimed in claim 1, wherein said sensor detects oxygen levels in the eye fluid.

6. A contact device as claimed in claim 1, wherein said sensor detects pH levels in the eye fluid.

7. A contact device as claimed in claim 1, wherein said sensor detects potassium levels in the eye fluid.

8. A contact device as claimed in claim 1, wherein said sensor detects sodium levels in the eye fluid.

9. A contact device for placement in contact with an eye, said contact device comprising:
   a contact surface for engaging a surface of the eye, and
   a sensor mounted on said contact surface, said sensor being positionable under an eye lid of the eyes,
   said sensor being a pressure sensor responsive to pressure intentionally imposed on said sensor by closing the eye lids for a predetermined period of time necessary to activate an electrical circuit for performing a function.

10. A contact device as claimed in claim 9, wherein a light emitting diode mounted on said contact surface is activated by intentional closure of the eye lids for a predetermined period of time.

11. A contact device for placement in contact with an eye, said contact device comprising:
   a contact surface for engaging a surface of the eye,
   a sensor mounted on said contact surface, said sensor producing a signal indicative of a bodily function, said signal being transmitted away from the eye for analysis and indication of a status of the bodily function, and
   a heater and a storage compartment mounted on said contact surface, said storage compartment including chemicals or drugs for release upon activation of said heater based upon said signal produced by said sensor.

12. A contact device as claimed in claim 11, wherein a light source is mounted on said contact surface, and said sensor detects light emitted from the light source.

13. A contact device for placement in contact with an eye, said contact device comprising:
   a contact surface for engagement with a portion of the eye, and
   a sensor mounted on said contact surface, said contact surface being positionable so that bodily fluids encounter said sensor, said sensor generating a signal indicative of a property of the encountered bodily fluids, said signal being transmitted externally of the live body for analysis of the signal and indication of a status of certain bodily functions, said sensor being responsive to the eye lid when the eyelids are moved into a position caused by sleeping of the individual wearing the contact device, a signal being generated by said sensor when closing eye lids indicative of sleep, said signal being transmitted to an alarm circuit for alerting the individual of the transition of the individual to a sleep state.

14. A contact device for placement in contact with an eye, said contact device comprising:
   a contact surface for engaging a surface of the eye,
   a sensor mounted on said contact surface, said sensor producing a signal indicative of a bodily function, said signal being transmitted away from the eye for analysis and indication of a status of the bodily function, and
   a pump for injecting an individual with medication based upon the signal generated by said sensor.

15. A contact device for placement in contact with an eye and eyelids, said contact device comprising:
   opposed contact surfaces for engagement with a portion of the eye and the eyelids,
   a sensor mounted on one of said contact surfaces,
   a sensor selective membrane surface of said sensor for passage therethrough of fluid from the eye,
   an electrode of said sensor positioned internally of said sensor selective membrane between said opposed contact surfaces, a signal generated by said electrode indicative of a property of the fluid from the eye, a transmitter located between said contact surfaces for transmitting said signal externally of the eye and the eye lids for analysis of the signal and indication of a status of certain bodily functions.

16. A contact device as claimed in claim 15, wherein said sensor detects glucose levels in the fluid from of the eye.

17. A contact device as claimed in claim 15, wherein said sensor detects cholesterol levels in the fluid from the eye.

18. A contact device as claimed in claim 15, wherein said sensor detects oxygen levels in the fluid from the eye.

19. A contact device as claimed in claim 15, wherein said sensor detects a temperature level in the fluid from the eye.

20. A contact device as claimed in claim 15, wherein said sensor detects potassium levels in the fluid from the eye.

21. A contact device as claimed in claim 15, wherein said sensor detects sodium levels in the fluid from the eye.

22. A contact device as claimed in claim 15, wherein the signal is transmitted through the air by said transmitter for receipt at a remote location.

* * * * *